(12) United States Patent
Bruchez et al.

(10) Patent No.: US 8,993,349 B2
(45) Date of Patent: Mar. 31, 2015

(54) METHOD FOR ENHANCING TRANSPORT OF SEMICONDUCTOR NANOCRYSTALS ACROSS BIOLOGICAL MEMBRANES

(75) Inventors: Marcel P. Bruchez, Pittsburgh, PA (US); R. Hugh Daniels, Palo Alto, CA (US); Jennifer Dias, Dublin, CA (US); Larry C. Mattheakis, Cupertino, CA (US); Hongjian Liu, Cupertino, CA (US); Aquanette M. Burt, San Francisco, CA (US); Berndt Christoffer Lagerholm, Chapel Hill, NC (US); Danith H. Ly, Pittsburgh, PA (US)

(73) Assignee: Life Technologies Corporation, Carlsbad, CA (US)

( * ) Notice: Subject to any disclaimer, the term of this patent is extended or adjusted under 35 U.S.C. 154(b) by 137 days.

(21) Appl. No.: 12/905,950

(22) Filed: Oct. 15, 2010

(65) Prior Publication Data
US 2011/0136139 A1 Jun. 9, 2011

Related U.S. Application Data

(63) Continuation of application No. 10/735,608, filed on Dec. 12, 2003, now abandoned, which is a continuation-in-part of application No. 09/972,744, filed on Oct. 5, 2001, now abandoned.

(60) Provisional application No. 60/238,677, filed on Oct. 6, 2000, provisional application No. 60/312,558, filed on Aug. 15, 2001.

(51) Int. Cl.
| | |
|---|---|
| *G01N 33/532* | (2006.01) |
| *G01N 33/543* | (2006.01) |
| *G01N 33/551* | (2006.01) |
| *G01N 21/76* | (2006.01) |
| *G01N 33/58* | (2006.01) |
| *B82Y 15/00* | (2011.01) |
| *G01N 33/50* | (2006.01) |

(52) U.S. Cl.
CPC ............... *G01N 33/588* (2013.01); *B82Y 15/00* (2013.01); *G01N 33/5008* (2013.01); *G01N 33/5014* (2013.01); *G01N 33/5076* (2013.01); *G01N 2333/726* (2013.01); *G01N 2500/10* (2013.01)
USPC ............ 436/532; 436/523; 436/524; 436/172

(58) Field of Classification Search
CPC ............... B82Y 5/00; C12Q 2563/155; A61K 49/0067; A61K 49/0423; A61K 49/1824; A61K 49/1836; G01N 33/588; G01N 33/587; C07K 17/14
See application file for complete search history.

(56) References Cited

U.S. PATENT DOCUMENTS

| | | | |
|---|---|---|---|
| 4,444,879 | A | 4/1984 | Foster et al. |
| 4,497,791 | A | 2/1985 | Gamble et al. |
| 4,847,240 | A | 7/1989 | Ryser et al. |
| 5,330,746 | A | 7/1994 | Friedman et al. |
| 5,420,016 | A | 5/1995 | Boguslaski et al. |
| 5,534,416 | A | 7/1996 | Millard et al. |
| 5,545,395 | A | 8/1996 | Tournier et al. |
| 5,643,599 | A | 7/1997 | Lee et al. |
| 5,652,122 | A | 7/1997 | Frankel et al. |
| 5,658,592 | A | 8/1997 | Tanihara et al. |
| 5,747,066 | A | 5/1998 | Pittrof et al. |
| 5,929,177 | A | 7/1999 | Kataoka et al. |
| 5,990,479 | A | 11/1999 | Weiss et al. |
| 6,036,610 | A | 3/2000 | Lewark |
| 6,036,886 | A | 3/2000 | Chhabra et al. |
| 6,051,386 | A | 4/2000 | Lerner |
| 6,114,038 | A | 9/2000 | Castro et al. |
| 6,194,213 | B1 | 2/2001 | Barbera-Guillem |
| 6,210,910 | B1 | 4/2001 | Walt et al. |
| 6,235,540 | B1 | 5/2001 | Siiman et al. |
| 6,251,303 | B1 | 6/2001 | Bawendi et al. |
| 6,274,323 | B1 | 8/2001 | Bruchez et al. |
| 6,306,610 | B1 | 10/2001 | Bawendi et al. |
| 6,306,993 | B1 | 10/2001 | Rothbard et al. |
| 6,319,426 | B1 | 11/2001 | Bawendi et al. |
| 6,469,132 | B1 | 10/2002 | Eisenberg et al. |
| 6,495,663 | B1 | 12/2002 | Rothbard et al. |
| 6,548,264 | B1 | 4/2003 | Tan et al. |
| 6,593,292 | B1 | 7/2003 | Rothbard et al. |
| 6,602,671 | B1 | 8/2003 | Bawendi et al. |
| 6,761,877 | B2 | 7/2004 | Barbera-Guillem |

(Continued)

FOREIGN PATENT DOCUMENTS

| | | |
|---|---|---|
| EP | 0990903 | 4/2000 |
| JP | 2001/094872 | 4/2001 |

(Continued)

OTHER PUBLICATIONS

Moffitt et al. Spherical assemblies of semiconductor nanoparticles in water-soluble block copolymer aggregates. Chem. Mater. 1998, vol. 10, pp. 1021-1028.*

(Continued)

*Primary Examiner* — Shafiqul Haq
(74) *Attorney, Agent, or Firm* — Life Technologies Corporation

(57) ABSTRACT

Semiconductor nanoparticle complexes comprising semiconductor nanoparticles in association with cationic polymers are described. Also described are methods for enhancing the transport of semiconductor nanoparticles across biological membranes to provide encoded cells. The methods are particularly useful in multiplex settings where a plurality of encoded cells are to be assayed. Kits comprising reagents for performing such methods are also provided.

21 Claims, 20 Drawing Sheets

(56) References Cited

U.S. PATENT DOCUMENTS

| | | |
|---|---|---|
| 6,761,902 B2 | 7/2004 | Sodroski et al. |
| 6,828,142 B2 | 12/2004 | Barbera-Guillem et al. |
| 6,838,243 B2 | 1/2005 | Lai et al. |
| 6,890,764 B2 | 5/2005 | Chee et al. |
| 6,953,656 B2 | 10/2005 | Jacobson et al. |
| 7,585,834 B2 | 9/2009 | Wender et al. |
| 8,148,847 B2 | 4/2012 | Lai |
| 2003/0004123 A1 | 1/2003 | Boucher, Jr. et al. |
| 2003/0032593 A1 | 2/2003 | Wender et al. |

FOREIGN PATENT DOCUMENTS

| | | |
|---|---|---|
| WO | WO-98/21587 | 5/1998 |
| WO | 99/45357 | 9/1999 |
| WO | 00/17655 | 3/2000 |
| WO | WO-00/17642 | 3/2000 |
| WO | WO-01/61045 | 8/2001 |
| WO | WO-02/29410 | 4/2002 |
| WO | WO-02/29410 A2 | 4/2002 |

OTHER PUBLICATIONS

Qi et al. Synthesis and characterizaiton of mixed CdS-ZnS nanoparticles in reverse micelles, Colloids and Surfaces 1996, vol. 111, pp. 195-202.*
U.S. Appl. No. 10/334,416, filed May 10, 2005, Chee, Mark.
U.S. Appl. No. 10/374,652 received Final Office action Sep. 7, 2005.
U.S. Appl. No. 10/374,652 received Final Office action Sep. 11, 2007.
U.S. Appl. No. 10/374,652 received Office Action Sep. 3, 2008.
U.S. Appl. No. 10/374,652 received Office Action Feb. 28, 2005.
U.S. Appl. No. 10/374,652 received Office Action May 20, 2009.
U.S. Appl. No. 10/374,652 Response to Final Office action Nov. 16, 2006 filed on Jan. 16, 2007.
U.S. Appl. No. 10/374,652 Response to Office Action Mar. 7, 2007 filed on Jun. 7, 2007.
U.S. Appl. No. 10/374,652 Response to Feb. 28, 2005 Office Action filed May 28, 2005.
U.S Appl. No. 10/735,608 received Office Action Sep. 5, 2008.
U.S. Appl. No. 11/682,063 received Office Action Nov. 27, 2009.
U.S. Appl. No. 11/682,063 received Office Action Jul. 2, 2010.
Bruchez, M., et al. "Semiconductor Nanocrystals as Fluorescent Biological Labels." *Science*, 1998, 2013-2016, 281.
"High Precision—Water Stable nanocrystals for coupling proteins, nucleic acids, antibodies and other biological molecules for reagent and assay development, Evitags for Biotech Researchers, Reagent Suppliers, and Assay Developers", *Evident Technologies* Feb. 2003.
EP04821527.1, "European Search Report," mailed on Aug. 20, 2007.
EP09154683.8, "Extended European Search Report," mailed Jun. 26, 2009.
Chan, Warren C. et al., "Quantum Dot Bioconjugates for Ultrasensitive Nonisotopic Detection", *Science* vol. 281 1998, 2016-2018.
Dubertret, B. et al., "In Vivo Imaging of Quantum Dots Encapsulated in Phospholipid Micelles", *Science* 298 2002, 1759-1762.
Futaki, et al., "Structural variety of membrane permeable peptides", *Curr Protein Pept Sci.* vol. 4, No. 2 2003, 87-96.
Lacoste, Thilo D. et al., "Super Resolution Molecular Ruler Using Single Quantum Dots", *Biophysical Journal* 78 Jan. 2000, 402A.
Lewin, Maite et al., "Tat peptide-derivatized magnetic nanoparticles allow in vivo tracking and recovery of progenitor cells", *Nature Biotechnology* vol. 18 Apr. 2000, 410-414.
PCT/US01/31410, "International Search Report," mailed Aug. 5, 2002.
PCT/US04/41045, "International Search Report," mailed Jan. 18, 2006.
Ricolleau, C. et al., "3D morphology of II-VI semiconductor nanocrystals grown in inverted micelles", *Journal of Crystal Growth* 1999, 486-499.
Schwarze, Steven R. et al., "In Vivo Protein Transduction: Delivery of a Biologically Active Protein into the Mouse", *Science* vol. 285 Sep. 3, 1999, 1569-1572.
Tkachenko, Alexander G. et al., "Multifunctional Gold Nanoparticle-Peptide Complexes for Nuclear Targeting", *J. Am. Chem. Soc.* 125 2003, 4700-4701.
Umezawa, N. et al., "Translocation of a beta-peptide across cell membranes", *J Am Chem Soc* vol. 124, No. 3 2002, 368-369.
Wooley, L. K. et al., ""Shell Crosslinked Polymer Assemblies: Nanoscale Constructs Inspired from Biological System"", vol. 38 Feb. 2, 2000, 1397-1407.
Korgel, B. et al., "Synthesis of size-monodisperse cds nanocrystals using phosphatidylcholine vesicles as true reaction compartments", *J. Phys. Chem.*, vol. 100, 1996, pp. 346-351.
Moghimi, S. et al., "Subcutaneous and intravenous delivery of diagnostic agents to the lymphatic system: applications in lymphoscintigraphy and indirect lymphography", vol. 37, Advanced Drug Delivery Reviews, 1999, pp. 295-312.
Jenkins, A. et al., "Glossary of Basic Terms in Polymer Science", *Pure and Applied Chernistry*, vol. 68, 1996, 2287, 2289, 2299.
Molecular Probes, "Qdot Nanocrystals—Section 6.6", Jul. 29, 2013, pp. 1-18.
Templeton, A. et al., "Water-Soluble, Isolable Gold Clusters Protected by Tiopronin and Coenzyme A Monolayers", *Langmuir*, 15, 1999, pp. 66-76.
Schenborn, E. et al., "Liposome-Mediated Transfection of Mammalian Cells", *Methods in Molecular Biology*, vol. 130, 2000, pp. 155-164.
Allen, C, et al., "Cellular internalization of PCL 20-b-PEO44 block copolymer micelles", *Biochimica et Biophysica Acta*, 1421, 1999, pp. 32-38.

* cited by examiner

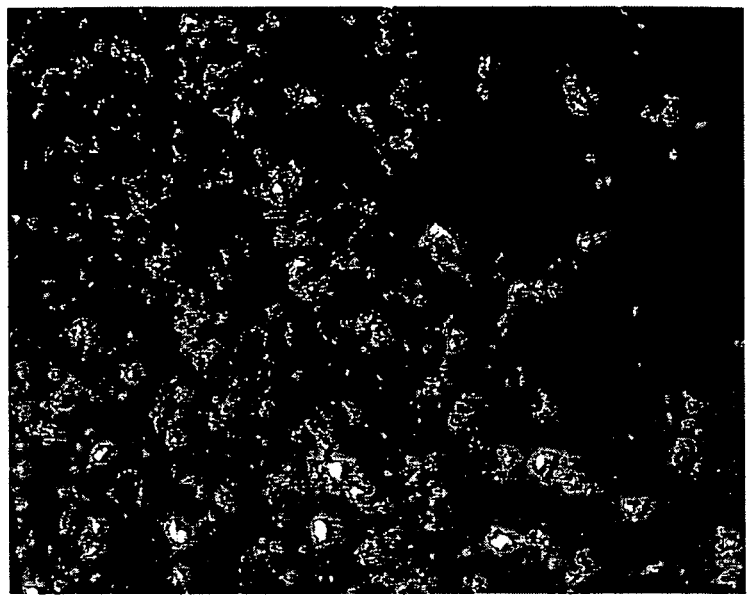
Fig. 10A
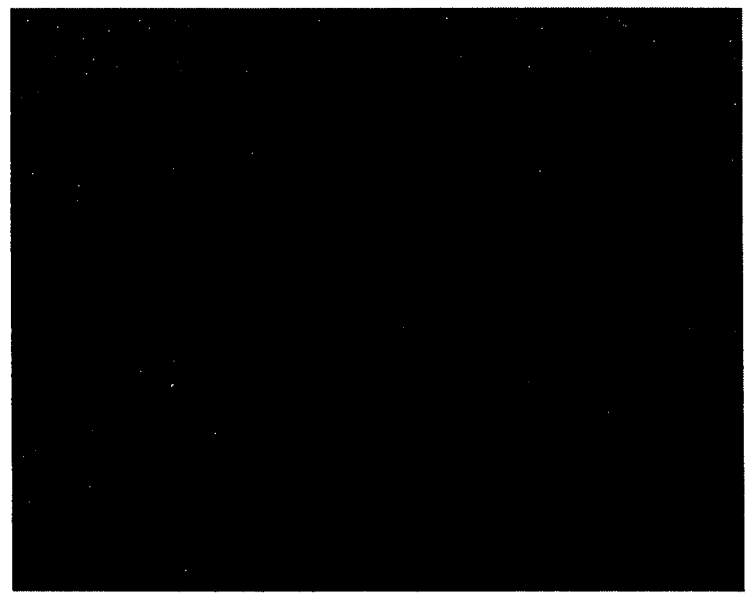
Fig. 10B
Figure 10

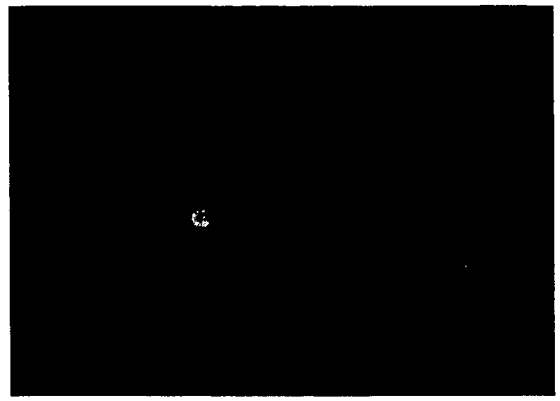
Fig. 13A
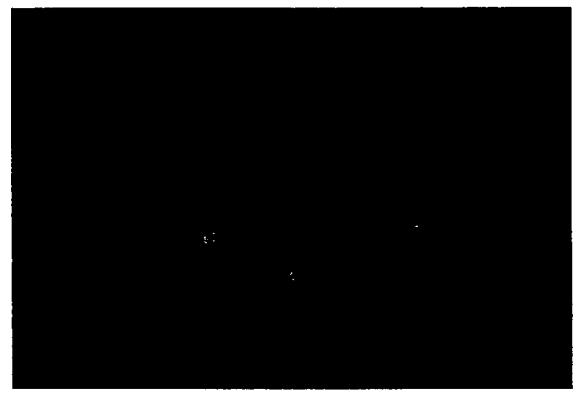
Fig. 13B
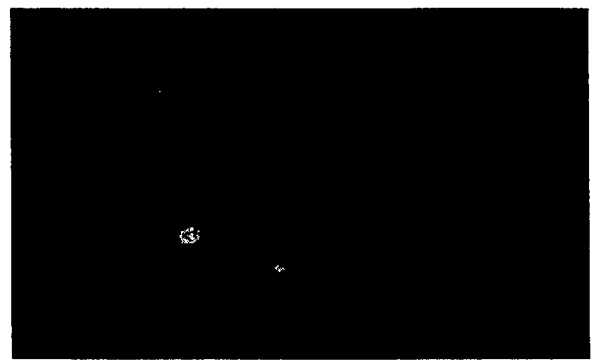
Fig. 13C
Figure 13

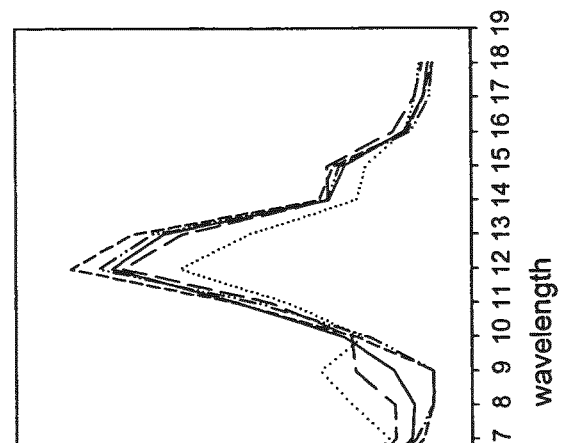
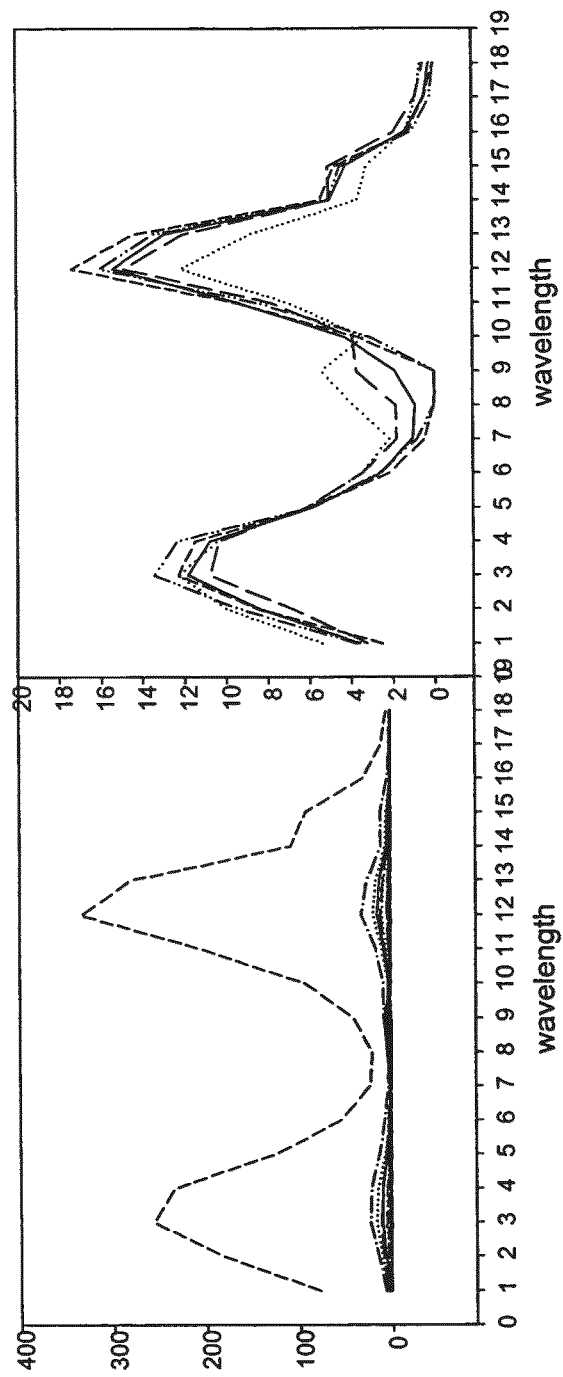
Fig. 16A
Fig. 16B
Figure 16

METHOD FOR ENHANCING TRANSPORT OF SEMICONDUCTOR NANOCRYSTALS ACROSS BIOLOGICAL MEMBRANES

CROSS-REFERENCE TO RELATED APPLICATIONS

This application is a continuation of U.S. patent application Ser. No. 10/735,608, filed Dec. 12, 2003 now abandoned, which is a continuation-in-part of U.S. patent application Ser. No. 09/972,744, filed Oct. 5, 2001 now abandoned, from which priority is claimed pursuant to 35 U.S.C. §120, which in turn claims the benefit of U.S. Ser. No. 60/238,677, filed Oct. 6, 2000, and U.S. Ser. No. 60/312,558, filed Aug. 15, 2001, from which applications priority is claimed under 35 USC §119(e)(1). The disclosures of the aforementioned applications are incorporated herein by reference in their entireties.

TECHNICAL FIELD

The present invention relates to semiconductor nanocrystal probes for biological applications, and methods of screening modulators of receptors using encoded cells. The invention also relates to the use of cationic polymers for enhancing the transport of semiconductor nanocrystals across biological membranes.

BACKGROUND OF THE INVENTION

Multiplexed assay formats are necessary to meet the demands of today's high-throughput screening methods, and to match the demands that combinatorial chemistry is putting on the established discovery and validation systems for pharmaceuticals. In addition, the ever-expanding repertoire of genomic information is rapidly necessitating very efficient, parallel and inexpensive assay formats. The requirements for all of these multiplexed assays are ease of use, reliability of results, a high-throughput format, and extremely fast and inexpensive assay development and execution.

For these high-throughput techniques, a number of assay formats are currently available. Each of these formats has limitations, however. By far the most dominant high-throughput technique is based on the separation of different assays into different regions of space. The 96-well plate format is the workhorse in this arena. In 96-well plate assays, the individual wells (which are isolated from each other by walls) are charged with different components, the assay is performed and then the assay result in each well measured. The information about which assay is being run is carried with the well number, or the position on the plate, and the result at the given position determines which assays are positive. These assays can be based on chemiluminescence, scintillation, fluorescence, absorbance, scattering, or colorimetric measurements, and the details of the detection scheme depend on the reaction being assayed. Assays have been reduced in size to accommodate 1536 wells per plate, though the fluid delivery and evaporation of the assay solution at this scale are significantly more problematic. High-throughput formats based on multi-well arraying require complex robotics and fluid dispensing systems to function optimally. The dispensing of the appropriate solutions to the appropriate bins on the plate poses a challenge from both an efficiency and a contamination standpoint, and pains must be taken to optimize the fluidics for both properties. Furthermore, the throughput is ultimately limited by the number of wells that one can put adjacent on a plate, and the volume of each well. Arbitrarily small wells have arbitrarily small volumes, resulting in a signal that scales with the volume, shrinking proportionally to $R^3$. The spatial isolation of each well, and thereby each assay, comes at the cost of the ability to run multiple assays in a single well. Such single-well multiplexing techniques are not widely used, due in large part to the inability to "demultiplex" or resolve the results of the different assays in a single well. However, such multiplexing would obviate the need for high-density well assay formats.

Each of the current techniques for ultra-high-throughput assay formats suffers from severe limitations. The present invention relates to methods for encoding spectra, which are readable with a single light source for excitation, into cells, which can be used in highly multiplexed assays.

The methods of the invention for encoding spectra can be used, for example, for screening for drug candidates, such as agonists or antagonists of receptors, for identifying new receptors, or for obtaining functional information pertaining to receptors, such as orphan G-protein coupled receptors (GPCRs). GPCRs represent one of the most important families of drug targets. G protein-mediated signaling systems have been identified in many divergent organisms, such as mammals and yeast. GPCRs respond to, among other extracellular signals, neurotransmitters, hormones, odorants and light. GPCRs are thought to represent a large superfamily of proteins that are characterized by the seven distinct hydrophobic regions, each about 20-30 amino acids in length, that forms the transmembrane domain. The amino acid sequence is not conserved across the entire superfamily, but each phylogenetically related subfamily contains a number of highly conserved amino acid motifs that can be used to identify and classify new members. Individual GPCRs activate particular signal transduction pathways, although at least ten different signal transduction pathways are known to be activated via GPCRs. For example, the beta 2-adrenergic receptor (βAR) is a prototype mammalian GPCR. In response to agonist binding, βAR receptors activate a G protein ($G_s$) which in turn stimulates adenylate cyclase and cyclic adenosine monophosphate production in the cell.

It has been postulated that members of the GPCR superfamily desensitize via a common mechanism involving G protein-coupled receptor kinase (GRK) phosphorylation followed by arrestin binding. The protein β-arrestin regulates GPCR signal transduction by binding agonist-activated receptors that have been phosphorylated by G protein receptor kinases. The β-arrestin protein remains bound to the GPCR during receptor internalization. The interaction between a GPCR and β-arrestin can be measured using several methods. In one example, the β-arrestin protein is fused to green fluorescent protein to create a protein fusion (Barak et al. (1997) *J. Biol. Chem.* 272(44):27497-500). The agonist-dependent binding of β-arrestin to a GPCR can be visualized by fluorescence microscopy. Microscopy can also be used to visualize the subsequent trafficking of the GPCR/β-arrestin complex to clathrin coated pits. Other methods for measuring binding of β-arrestin to a GPCR in live cells include techniques such as FRET (fluorescence resonance energy transfer), BRET (bioluminescent energy transfer) or enzyme complementation (Rossi et al. (1997) *Proc. Natl. Acad. Sci. USA* 94(16):8405-10).

At present, there are nearly 400 GPCRs whose natural ligands and function are known. These known GPCRs, named for their endogenous ligands, have been classified into five major categories: Class-A Rhodopsin-like; Class-B Secretin-like; Class-C Metabotropic glutamate/pheromone; Class-D Fungal pheromone; Class-E cAMP (dictyostelium). Representative members of Class-A are the amine receptors (e.g., muscarinic, nicotinic, adrenergic, adenosine, dopamine, histamine and serotonin), the peptide receptors (e.g., angiotensin, bradykinin, chemokines, endothelin and opioid), the hormone receptors (e.g., follicle stimulating, lutropin and thyrotropin), and the sensory receptors, including rhodopsin (light), olfactory (smell) and gustatory (taste) receptors. Representatives of Class-B include secretin, calcitonin, gastrin and glucagon receptors. Much less is known about Classes C-E.

Many available therapeutic drugs in use today target GPCRs, as they mediate vital physiological responses, including vasodilation, heart rate, bronchodilation, endocrine secretion, and gut peristalsis (Wilson and Bergsma (2000) *Pharm. News* 7: 105-114). For example, ligands to β-adrenergic receptors are used in the treatment of anaphylaxis, shock, hypertension, hypotension, asthma and other conditions. Additionally, diseases can be caused by the occurrence of spontaneous activation of GPCRs, where a GPCR cellular response is generated in the absence of a ligand. Drugs that are antagonists of GPCRs decrease this spontaneous activity (a process known as inverse agonism) are important therapeutic agents. Examples of commonly prescribed GPCR-based drugs include Atenolol (Tenormin®), Albuterol (Ventolin®), Ranitidine (Zantac®), Loratadine (Claritin®), Hydrocodone (Vicodin®) Theophylline (TheoDur®), and Fluoxetine (Prozac®).

Due to the therapeutic importance of GPCRs, methods for the rapid screening of compounds for GPCR ligand activity are desirable. Additionally, there is a need for methods of screening orphan GPCRs for interactions with known and putative GPCR ligands in order to characterize such receptors. The present invention meets these and other needs.

Peptides and cationic polymers have been used to transport various substances across biological membranes. For example, Tkachenko et al., *J. Am. Chem. Soc.* (2003) 125: 4700-4701 describes gold nanoparticle-peptide complexes for targeting molecules to the cell nucleus. U.S. Pat. No. 6,495,663 describes methods for transporting drugs and macromolecules across biological membranes using transport polymers, such as poly-Arg polymers, conjugated to the agent to be transported. U.S. Pat. No. 4,847,240 describes the use of high molecular weight polymers of lysine for increasing transport of various drugs across cellular membranes. PCT Pub. No. WO 94/04686 and Fawell et al., *Proc. Natl. Acad. Sci.* (1994) 91:664-668 proposed the use of fragments of the tat protein containing the tat basic region (residues 49-57 having the sequence RKKRRQRRR (SEQ ID NO: 1).

However, none of the above-described art pertains to the use of cationic polymers to transport semiconductor nanoparticles across biological membranes.

SUMMARY OF THE INVENTION

Methods and compositions for encoding cells with semiconductor nanoparticles such as semiconductor nanocrystals, other fluorescent species, or otherwise detectable species and combinations thereof are provided. In one aspect, a method is provided comprising the ability to separately identify individual populations of cells in a mixture of different types of cells which is highly advantageous for many applications. This method is especially useful for identifying a population of cells derived from an initial sample of one or more cells via its unique spectral code after several cell divisions. The method facilitates analysis of many otherwise identical cells which only differ by the presence or absence of one or more genes and which are subjected to a functional assay.

The ability to detect populations of cells derived from a few precursors by virtue of their spectral code greatly facilitates the high-throughput analysis of many systems. It allows the identification of populations that have multiplied in a particular environment in the absence of any further experimental processing. The number of cells bearing the diluted code can be determined using various spectral scanning devices.

Many specific binding interactions can only occur when at least one of the binding partners is in its 'natural' environment. This environment is often the membrane of a cell. Therefore to have a method to simultaneously interrogate multiple populations of cell that are of different lineages or are expressing different binding partners for a molecule of interest requires an ability to separately encode those cells. This invention describes a method by which this is done using SCNCs, other fluorescent species, or otherwise detectable species and combinations thereof. This is useful in, for example, high throughput cell based screening systems. One example is the analysis of G-protein coupled receptors and their binding partners—these receptors span lipid bilayers 7 times and can only bind their partners when in this conformation.

Another utility for this invention is as a method for separately coding cells in order to follow the fate of a specific population of cells while it is in a mixed population.

The present invention also relates to methods for providing enhanced transport of semiconductor nanoparticles, such as semiconductor nanocrystals across cell membranes, thereby encoding cells which can be used in highly multiplexed assays. The methods of the invention for encoding spectra can be used, for example, in multiplex settings where a plurality of different cell types are encoded and assayed for a phenotype. The large number of distinguishable semiconductor nanoparticles can be employed to simultaneously analyze differently spectrally encoded cells. The methods may be used to enhance transport of semiconductor nanoparticles across any of a number of biological membranes including, but not limited to, eukaryotic cell membranes, prokaryotic cell membranes, and cell walls. The methods are also useful in single-plex type assays, such as to follow cell mobility, for cell tracking and in in vivo applications.

Accordingly, in one aspect, a method is provided for enhancing the transport of semiconductor nanoparticles, such as semiconductor nanocrystals and related species across biological membranes. The method entails the use of these species with associated cationic polymers. Labeling cells in this way allows individual populations of cells in a mixture of different types of cells to be separately identified. This method is especially useful for identifying a population of cells derived from an initial sample of one or more cells via its unique spectral code after several cell divisions. The method facilitates analysis of many otherwise identical cells which only differ by the presence or absence of one or more genes and which are subjected to a functional assay.

The ability to detect populations of cells derived from a few precursors by virtue of their spectral code greatly facilitates the high-throughput analysis of many systems. It allows the identification of populations that have multiplied in a particular environment in the absence of any further experimental processing. The number of cells bearing the diluted code can be determined using various spectral scanning devices.

Another utility for this invention is as a method for separately coding cells in order to follow the fate of a specific population of cells while it is in a mixed population.

The invention thus provides a semiconductor nanoparticle complex comprising a semiconductor nanoparticle associated with a cationic polymer capable of enhancing the transport of the semiconductor nanoparticle across a biological membrane.

In certain embodiments, the semiconductor nanoparticle is a semiconductor nanocrystal. The semiconductor nanocrystal can comprise a core and optionally a shell. The core and the shell can be selected from the group consisting of ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, AlAs, AlP, AlSb, AlS, Ge, Si, Pb, PbS, PbSe, an alloy thereof, and a mixture thereof.

In further embodiments, the cationic polymer is tat peptide from the protein transduction domain of the HIV tat protein, such as a peptide comprising the sequence RKKRRQRRR (SEQ ID NO: 1). In other embodiments, the cationic polymer has from 5 to 25 contiguous Lys and/or Arg residues.

In yet additional embodiments, the biological membrane is a cell membrane.

In a further embodiment, the invention is directed to a semiconductor nanocrystal complex comprising a semiconductor nanocrystal associated with a cationic polymer capable of enhancing the transport of the semiconductor nanocrystal across a cell membrane, wherein the semiconductor nanocrystal comprises a core and a shell, wherein the core and the shell are each selected from the group consisting of ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, AlAs, AlP, AlSb, AlS, Ge, Si, Pb, PbS, PbSe, an alloy thereof, and a mixture thereof.

In certain embodiments, the core is CdSe and the shell is ZnS.

In additional embodiments, the cationic polymer is tat peptide from the protein transduction domain of the HIV tat protein, such as a peptide comprising the sequence RKKRRQRRR (SEQ ID NO: 1). In other embodiments, the cationic polymer has from 5 to 25 contiguous Lys and/or Arg residues.

In yet further embodiments, the invention is directed to a method of enhancing the transport of a semiconductor nanoparticle across a biological membrane comprising contacting a cell with any of the semiconductor nanoparticles described above, under conditions that provide for the transport of the semiconductor nanoparticle across the biological membrane.

In additional embodiments, the invention is directed to a method of distinguishably identifying a cell, comprising:
(a) providing a cell; and
(b) contacting the cell with any of the semiconductor nanoparticle complexes described above, under conditions in which the semiconductor nanoparticle is transported across the cell membrane to provide a labeled cell, thereby identifying the cell.

In yet further embodiments, the invention is directed to a method of identifying a cell in a mixed population of cells, comprising:
(a) providing a first cell;
(b) contacting the cell with any of the semiconductor nanoparticle complexes described above, under conditions in which the semiconductor nanoparticle is transported across the cell membrane to provide an encoded first cell;
(c) mixing the encoded first cell with a second cell distinct therefrom to form a mixed population of cells;
(d) culturing the mixed population of cells;
(e) exposing the cultured mixed population of cells to an excitation energy source; and
(f) detecting a semiconductor nanoparticle code to identify the encoded cell.

In certain embodiments of any of the methods above, the cell is prokaryotic or eukaryotic. Moreover, the cell can be a mammalian cell selected from the group consisting of a human cell, a mouse cell, a rat cell, a bovine cell, and a hamster cell.

Kits comprising reagents useful for performing the methods of the invention are also provided.

BRIEF DESCRIPTION OF THE FIGURES

FIG. 10 is a fluorescence micrograph of CHO cells and SCNCs incubated in the presence (FIG. 10A) or absence (FIG. 10B) of Chariot reagent as described in Example 1.

FIG. 13 is a fluorescence micrograph of CHO cells cotransfected with red polymer crosslinked SCNCs and EGFP/rac DNA as described in Example 4. Shown is the image using a 535 nm emission filter (FIG. 13A), a 625 nm emission filter (FIG. 13B), and the two images overlayed (FIG. 13C).

FIG. 16 is a graphical representation of spectra (raw, FIG. 16A; normalized, FIG. 16B) of five individual CHO cells encoded with green and red SCNCs using Chariot reagent as described in Example 5.

DETAILED DESCRIPTION OF THE INVENTION

Figure 1:
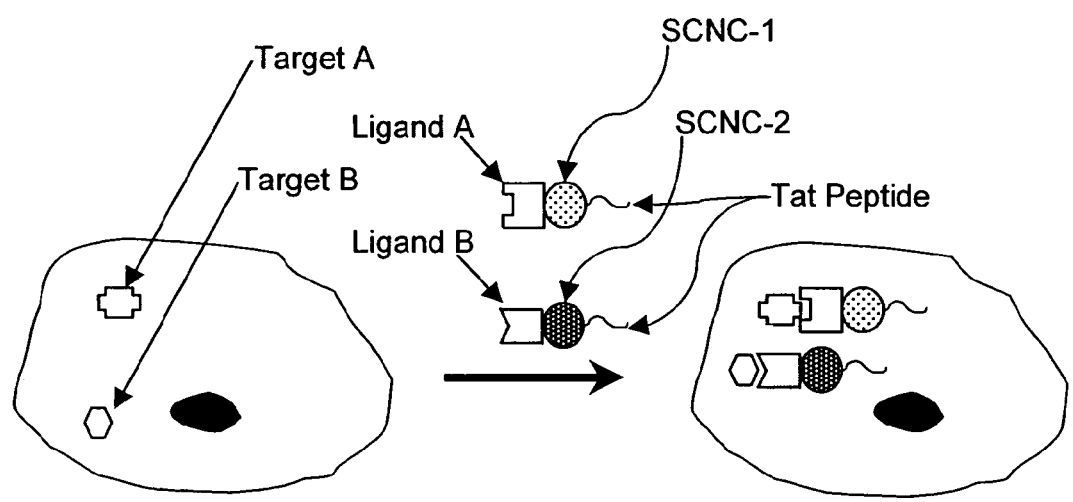
FIG. 1 is a pictorial representation illustrating a method for introducing semiconductor nanocrystals (SCNCs), to which have been conjugated cellular target-specific ligands, into live cells using peptides that facilitate passage into cells.

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Haines & S J. Higgins, eds., 1984); *Methods in Enzymology* (Academic Press, Inc.); Kirk-Othmer's *Encyclopedia of Chemical Technology*; and House's Modern Synthetic Reactions.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

It must be noted that, as used in this specification and the appended claims, the singular forms "a", "an" and "the" include plural referents unless the content clearly dictates otherwise. Thus, for example, reference to "a cell" includes two or more cells, and the like.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The term "biological membrane" as used herein refers to a lipid-containing barrier which separates cells or groups of cells from the extracellular space. Biological membranes include, without limitation, plasma membranes, cell walls, intracellular organelle membranes, such as the mitochondrial membrane, nuclear membranes, and the like By a "enhancing transport" of a semiconductor nanoparticle, such as a semiconductor nanocrystal or like species across a biological membrane is meant that the transporting agent, such as the cationic polymer, is effective to impart to the associated semiconductor nanoparticle a degree (i.e., amount) and/or rate of trans-membrane transport across a biological membrane that is greater than the degree and/or rate of trans-membrane transport of the semiconductor nanoparticle when it is not associated with the transporting agent. Enhanced transport is determined by comparing the delivery of the semiconductor nanoparticle that is not associated with the cationic polymer with a semiconductor nanoparticle so associated, delivered under the same conditions.

The term "polymer" is used herein in its conventional sense to refer to a compound having two or more monomer units, and is intended to include linear and branched polymers, the term "branched polymers" encompassing simple branched structures as well as hyperbranched and dendritic polymers. The term "monomer" is used herein to refers to compounds that are not polymeric. The term "polymer" as used herein includes homopolymers and copolymers (random and block). "Polymers" herein may be naturally occurring, chemically modified, or chemically synthesized. A peptide is an example of a polymer that can be composed of identical or non-identical naturally occurring or non-naturally occurring amino acid subunits that are joined by peptide linkages.

The term "cationic polymer" as used herein refers to a polymer that includes a sequence of positive charges sufficient to enhance transport of semiconductor nanoparticles across a biological membrane of choice when in association with the polymer. The polymer may have a net positive charge. Alternatively, the multiple positive charges may form an adequate sequence in the primary structure, or an adequate spacial arrangement in the tertiary structure, or both, to cause enhanced cellular uptake, even though the molecule does not have an overall net positive charge. Preferably, the cationic polymer will include from about 5 to about 50 subunits, more preferably from about 5 to about 25 subunits, or any number within these ranges, such as 6, 7, 8, 9, 10 . . . 15 . . . 20 . . . 25, and so forth, with at least half of the subunits bearing a positive charge.

The term "peptide" is used herein to refer to a compound made up of a single chain of D- or L-amino acids or a mixture of D- and L-amino acids joined by peptide bonds. Generally, peptides contain at least two amino acid residues and are less than about 50 amino acids in length.

The terms "poly-arginine," "poly-lysine," "poly-Arg," "poly-Lys" and like terms with reference to other naturally and non-naturally occurring amino acids refer to a polymeric sequence composed of contiguous residues of the particular amino acid, such as arginine, lysine, etc.; poly-L-arginine, poly-L-lysine, etc., refers to all L-arginines, L-lysines, etc.; poly-D-arginine, poly-D-lysine, etc. refers to all D-arginines, D-lysines, etc. Poly-L-arginine, poly-L-lysine, etc., are also abbreviated by the three or one letter code for the amino acid shown in the table herein, followed by the number of like residues in the peptide (e.g., D-Arg9 represents a 9-mer of contiguous D-arginine residues).

The term "guanidyl", "guanidinyl", and "guanidino" are used interchangeably herein to refer to a moiety having a formula —HN=C(NH$_2$)NH (unprotenated form). As an example, arginine contains a guanidyl (guanidino) moiety, and is also referred to as 2-amino-5-guanidinovaleric acid or α-amino-β-guanidinovaleric acid. "Guanidinium" refers to the positively charged conjugate acid form.

"Amidinyl" and "amidino" refer to a moiety having the formula —C(=NH)(NH$_2$). "Amidinium" refers to the positively charged conjugate acid form.

The term "nanoparticle" refers to a particle, generally a semiconductive or metallic particle, having a diameter in the range of about 1 nm to about 1000 nm, preferably in the range of about 2 nm to about 50 nm, more preferably in the range of about 2 nm to about 20 nm (for example about 2, 3, 4, 5, 6, 7, 8, 9, 10, 11, 12, 13, 14, 15, 16, 17, 18, 19, or 20 nm).

The terms "semiconductor nanoparticle" and "semiconductive nanoparticle" refer to a nanoparticle as defined above that is composed of an inorganic semiconductive material, an alloy or other mixture of inorganic semiconductive materials, an organic semiconductive material, or an inorganic or organic semiconductive core contained within one or more semiconductive overcoat layers.

The term "metallic nanoparticle" refers to a nanoparticle as defined above that is composed of a metallic material, an alloy or other mixture of metallic materials, or a metallic core contained within one or more metallic overcoat layers.

The terms "semiconductor nanocrystal" (SCNC), "quantum dot" and "Qdot™ nanocrystal" are used interchangeably herein to refer to semiconductor nanoparticles composed of an inorganic crystalline material that is luminescent (i.e., capable of emitting electromagnetic radiation upon excitation), and that include an inner core of one or more first semiconductor materials that is optionally contained within an overcoating or "shell" of a second semiconductor material. A semiconductor nanocrystal core surrounded by a semiconductor shell is referred to as a "core/shell" semiconductor nanocrystal. The surrounding shell material will preferably have a bandgap energy that is larger than the bandgap energy of the core material and may be chosen to have an atomic spacing close to that of the core substrate. Suitable semiconductor materials for the core and/or shell include, but are not limited to, the following: materials comprised of a first element selected from Groups 2 and 12 of the Periodic Table of the Elements and a second element selected from Group 16 (e.g., ZnS, ZnSe, ZnTe, CDs, CdSe, CdTe, HgS, HgSe, HgTe, MgS, MgSe, MgTe, CaS, CaSe, CaTe, SrS, SrSe, SrTe, BaS, BaSe, BaTe, and the like); materials comprised of a first element selected from Group 13 of the Periodic Table and a second element selected from Group 15 (GaN, GaP, GaAs, GaSb, InN, InP, InAs, InSb, and the like); materials comprised of a Group 14 element (Ge, Si, and the like); materials such as PbS, PbSe and the like; and alloys and mixtures thereof. As used herein, all references to the Periodic Table of the Elements and groups thereof is with reference to the new IUPAC system for numbering element groups, as set forth in the Handbook of Chemistry and Physics, 81$^{st}$ Edition (CRC Press, 2000).

An SCNC is optionally surrounded by a "coat" of an organic capping agent. The organic capping agent may be any number of materials, but has an affinity for the SCNC surface. In general, the capping agent can be an isolated organic molecule, a polymer (or a monomer for a polymerization reaction), an inorganic complex, or an extended crystalline structure. The coat can be used to convey solubility, e.g., the ability to disperse a coated SCNC homogeneously into a chosen solvent, functionality, binding properties, or the like. In addition, the coat can be used to tailor the optical properties of the SCNC.

Thus, the terms "semiconductor nanocrystal," "SCNC," "quantum dot" and "Qdot™ nanocrystal" as used herein include a coated SCNC core, as well as a core/shell SCNC.

"Monodisperse" particles include a population of particles wherein at least about 60% of the particles in the population, more preferably about 75% to about 90% or more, or any percentage within these stated ranges, of the particles in the population fall within a specified particle size range. A population of monodisperse particles deviates less than 10% rms (root-mean-square) in diameter, and preferably deviates less than 5% rms.

The phrase "one or more sizes of SCNCs" is used synonymously with the phrase "one or more particle size distributions of SCNCs." One of ordinary skill in the art will realize that particular sizes of SCNCs are actually obtained as particle size distributions.

By "luminescence" is meant the process of emitting electromagnetic radiation (light) from an object. Luminescence results when a system undergoes a transition from an excited state to a lower energy state with a corresponding release of energy in the form of a photon. These energy states can be electronic, vibrational, rotational, or any combination thereof. The transition responsible for luminescence can be stimulated through the release of energy stored in the system chemically or added to the system from an external source. The external source of energy can be of a variety of types including chemical, thermal, electrical, magnetic, electromagnetic, and physical, or any other type of energy source capable of causing a system to be excited into a state higher in energy than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

"Preferential binding" refers to the increased propensity of one member of a binding pair to bind to a second member as compared to other components in the sample.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3'-P5' phosphoramidates, oligodeoxyribonucleotide N3'-P5' thiophosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, thiophosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base that form hydrogen bonds to a respective complementary pyrimidine or purine. The resultant modified nucleotidic unit optionally may form a base pair with other such modified nucleotidic units but not with A, T, C, G or U. A basic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-$NH_2$, respectively, of adenosine and between the C2-oxy, N3 and C4-$NH_2$, of cytidine and the C2-$NH_2$, N'—H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide, which will not effectively base pair with guanosine but will form a base pair with isoguanosine. Isocytosine is available from Sigma Chemical Co. (St. Louis, Mo.); isocytidine may be prepared by the method described by Switzer et al. (1993) *Biochemistry* 32:10489-10496 and references cited therein; 2'-deoxy-5-methyl-isocytidine may be prepared by the method of Tor et al. (1993) *J. Am. Chem. Soc.* 115:4461-4467 and references cited therein; and isoguanine nucleotides may be prepared using the method described by Switzer et al. (1993), supra, and Mantsch et al. (0.1993) *Biochem.* 14:5593-5601, or by the method described in U.S. Pat. No. 5,780,610 to Collins et al. Other nonnatural base pairs may be synthesized by the method described in Piccirilli et al. (1990) *Nature* 343:33-37 for the synthesis of 2,6-diaminopyrimidine and its complement (1-methylpyrazolo-[4,3]pyrimidine-5,7-(4H,6H)-dione. Other such modified nucleotidic units which form unique base pairs are known, such as those described in Leach et al. (1992) *J. Am. Chem. Soc.* 114:3675-3683 and Switzer et al., supra.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

"Complementary" or "substantially complementary" refers to the ability to hybridize or base pair between nucleotides or nucleic acids, such as, for instance, between the two strands of a double stranded DNA molecule or between a polynucleotide primer and a primer binding site on a single stranded nucleic acid to be sequenced or amplified. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, Kanehisa (1984) *Nucleic Acids Res.* 12:203.

"Preferential hybridization" as a form of preferential binding refers to the increased propensity of one polynucleotide to bind to a complementary target polynucleotide in a sample as compared to noncomplementary polynucleotides in the sample or as compared to the propensity of the one polynucleotide to form an internal secondary structure such as a hairpin or stem-loop structure under at least one set of hybridization conditions.

Stringent hybridization conditions will typically include salt concentrations of less than about 1M, more usually less than about 500 mM and preferably less than about 200 mM. Hybridization temperatures can be as low as 5 C, but are typically greater than 22 C, more typically greater than about 30 C, and preferably in excess of about 37 C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art. Less stringent, and/or more physiological, hybridization conditions are used where a labeled polynucleotide amplification product cycles on and off a substrate linked to a complementary probe polynucleotide during a real-time assay which is monitored during PCR amplification such as a molecular beacon assay. Such less stringent hybridization conditions can also comprise solution conditions effective for other aspects of the method, for example reverse transcription or PCR.

The terms "aptamer" (or "nucleic acid antibody") is used herein to refer to a single- or double-stranded polynucleotide that recognizes and binds to a desired target molecule by virtue of its shape. See, e.g., PCT Publication Nos. WO 92/14843, WO 91/19813, and WO 92/05285.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides contain co- and/or post-translational modifications of the polypeptide, for example, glycosylations, acetylations, phosphorylations, and sulphations. In addition, protein fragments, analogs (including amino acids not encoded by the genetic code, e.g., homocysteine, ornithine, D-amino acids, and creatine), natural or artificial mutants or variants or combinations thereof, fusion proteins, derivatized residues (e.g., alkylation of amine groups, acetylations or esterifications of carboxyl groups) and the like are included within the meaning of polypeptide.

The terms "substrate" and "support" are used interchangeably and refer to a material having a rigid or semi-rigid surface.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g., any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, biotin-neutravidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

Terms such as "connected," "attached," "linked," and "conjugated" are used interchangeably herein and encompass direct as well as indirect connection, attachment, linkage or conjugation, including covalent and non-covalent binding, adsorption, physical immobilization and the like, unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention.

Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, an antibody will selectively bind to the antigen against which it was raised; A DNA molecule will bind to a substantially complementary sequence and not to unrelated sequences. The affinity molecule can comprise any molecule, or portion of any molecule, that is capable of being linked to a semiconductor nanocrystal and that, when so linked, is capable of recognizing specifically a detectable substance. Such affinity molecules include, by way of example, such classes of substances as antibodies, as defined below, monomeric or polymeric nucleic acids, aptamers, proteins, polysaccharides, sugars, and the like. See, e.g., Haugland, "Handbook of Fluorescent Probes and Research Chemicals" (Sixth Edition), and any of the molecules capable of forming a binding pair as described above.

An "SCNC conjugate" is an SCNC linked to a first member of a binding pair, as defined above, or an SCNC linked to a cationic polymer. For example, an SCNC is "linked" or "conjugated" to, or chemically "associated" with, such molecules when the SCNC is coupled to, or physically associated with the molecule. Thus, these terms intend that the SCNC may either be directly linked to the molecule or may be linked via a linker moiety, such as via a chemical linker. The terms indicate items that are physically linked by, for example, covalent chemical bonds, physical forces such van der Waals or hydrophobic interactions, encapsulation, embedding, non-covalent interactions, adsorption and the like. For example, nanocrystals can be associated with biotin which can bind to the proteins avidin, streptavidin, neutravidin, and the like.

When used in relation to a composition comprising a cell and an SCNC or other detectable moiety, the term "associated" is intended to include cells in which the SCNC is contained in the nucleus, in the cytoplasm, in an organelle contained within the cell, embedded either in whole or in part in the cytoplasmic membrane, the nuclear membrane or any other membrane within the cell, is bound to a molecule within the cell or in the cell membrane, or otherwise fixed to the cell in a manner resistant to the environment or changes in the environment, such as experimental manipulations, exposure to candidate pharmacological agents, or the like.

The term "antibody" as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, e.g., Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 149B: 120-126); humanized antibody molecules (see, e.g., Riechmann et al. (1988) Nature 332:323-327; Verhoeyan et al. (1988) Science 239:1534-1536; and U.K. Patent Publication No. GB 2,276,169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote et al. (1985) Monoclonal Antibodies and Cancer Therapy, Alan R. Liss, p. 77.

"Multiplexing" herein refers to an assay or other analytical method in which multiple cell types can be assayed simultaneously by using more than spectral code to encode each cell type, each different code having at least one different fluorescence characteristic (for example excitation wavelength, emission wavelength, emission intensity, FWHM (full width at half maximum peak height), or fluorescence lifetime).

For example, two different preparations of SCNCs may have the same composition but different particle sizes, and thus differ in excitation and/or emission wavelength. Or, two different preparations may have the same particle size or particle size distribution but different composition, and thus also differ in excitation and/or emission wavelength. Different preparations having different compositions of SCNCs can have different fluorescent lifetimes, and thus their emission spectra can be distinguished even when they have the same emission wavelength and intensity, for example by sampling the emission from the encoded substance at different times after excitation. Differences in FWHM can be achieved for example by using SCNCs of different composition, or of the same composition but which are synthesized differently, or by mixing different SCNC "preparations" having overlapping emission peaks together to form a new preparation.

An SCNC having a known emission wavelength and/or intensity may be included with the SCNCs used for the encoding to provide an internal standard for calibrating the wavelength and/or intensity of the other SCNC(s) used in the conjugate. In addition, other nanoparticles, e.g., metallic or magnetic nanoparticles, examples of which are tabulated herein, can be used for the encoding.

The phenotypic assays of the invention can be performed in multiplex formats. Multiplex methods are provided employing 2, 3, 4, 5, 10, 15, 20, 25, 50, 100, 200, 500, 1000 or more different encoded cell types which can be used simultaneously to assay for a phenotype.

Where different ligands are included in a multiplex assay, the different ligands can be encoded so that they can be distinguished. Any encoding scheme can be used; conveniently, the encoding scheme can employ one or more different fluorescent species, which can be nanoparticles, e.g., fluorescent semiconductor nanocrystals and other metallic or magnetic nanoparticles. For the sake of simplicity, the following discussion will refer to semiconductor nanocrystals as the encoding species. However, it is to be understood that this convention is not intended to be limiting in any way and that other encoding species, e.g., other nanoparticles, such as metallic or magnetic nanoparticles, as well as combinations of encoding species such as SCNCs and other nanoparticles, can be used to encode cells according to the disclosure that follows.

Thus, for example, in addition to SCNCs, the nanoparticles of the invention may also be light-scattering metallic nanoparticles. Such particles are useful, for example, in surface-enhanced Raman scattering (SERS), which employs nanometer-size particles onto which Raman-active moieties (e.g., a dye or pigment, or a functional group exhibiting a characteristic Raman spectrum) are adsorbed or attached. Metallic nanoparticles may be comprised of any metal or metallic alloy or composite, although for use in SERS, a SERS-active metal is used, e.g., silver, gold, copper, lithium, aluminum, platinum, palladium, or the like. In addition, the particles can be in a core-shell configuration, e.g., a gold core may be encased in a silver shell; see, e.g., Freeman et al. (1996) J. Phys. Chem. 100:718-724, or the particles may form small aggregates in solution. Kneipp et al. (1998) Applied Spectroscopy 52:1493.

In addition, organic fluorescent species can be used to encode cells alone or in combination with nanoparticles. Suitable fluorescent species include, but are not limited to, fluorescein, 5-carboxyfluorescein (FAM), rhodamine, 5-(2'-aminoethyl) aminonapthalene-1-sulfonic acid (EDANS), anthranilamide, coumarin, terbium chelate derivatives, Reactive Red 4, BODIPY dyes and cyanine dyes. In a preferred aspect, the organic fluorescent donors include Alexa 488, fluorescein, fluorescein iso-thiocyanate (FITC), Cy3, Cy5, PE, Texas Red, Cascade Blue, Bodipy, TMR and tetramethyl rhodamine isothiocyanate (TRITC).

Other fluorescent species are set forth below in Table 1. Those of skill in the art will know of other suitable fluorescence species suitable for use in the present invention.

TABLE 1

| Fluorochrome | Excitation Wavelength | Emission Wavelength |
|---|---|---|
| Acid Fuchsin | 540 | 630 |
| Acridine Orange (Bound to DNA) | 502 | 526 |
| Acridine Red | 455-600 | 560-680 |
| Acridine Yellow | 470 | 550 |
| Acriflavin | 436 | 520 |
| AFA (Acriflavin Feulgen SITSA) | 355-425 | 460 |
| Alizarin Complexon | 530-560 | 580 |
| Alizarin Red | 530-560 | 580 |

TABLE 1-continued

| Fluorochrome | Excitation Wavelength | Emission Wavelength |
|---|---|---|
| Allophycocyanin | 650 | 661 |
| ACMA | 430 | 474 |
| AMCA-S, AMC | 345 | 445 |
| Aminoactinomycin D | 555 | 655 |
| 7-Aminoactinomycin D-AAD | 546 | 647 |
| Aminocoumarin | 350 | 445 |
| Anthroyl Stearate | 361-381 | 446 |
| Astrazon Brilliant Red 4G | 500 | 585 |
| Astrazon Orange R | 470 | 540 |
| Astrazon Red 6B | 520 | 595 |
| Astrazon Yellow 7 GLL | 450 | 480 |
| Atabrine | 436 | 490 |
| Auramine | 460 | 550 |
| Aurophosphine | 450-490 | 515 |
| Aurophosphine G | 450 | 580 |
| BAO 9-(Bisamino-phenyloxadiazole) | 365 | 395 |
| BCECF | 505 | 530 |
| Berberine Sulphate | 430 | 550 |
| Bisbenzamide | 360 | 600-610 |
| BOBO-1, BO-PRO-1 | 462 | 481 |
| Blancophor FFG Solution | 390 | 470 |
| Blancophor SV | 370 | 435 |
| Bodipy Fl | 503 | 512 |
| Bodipy TMR | 542 | 574 |
| Bodipy TR | 589 | 617 |
| BOPRO 1 | 462 | 481 |
| Brilliant Sulpho-flavin FF | 430 | 520 |
| Calcein | 494 | 517 |
| Calcien Blue | 370 | 435 |
| Calcium Green | 505 | 532 |
| Calcium Orange | 549 | 576 |
| Calcofluor RW Solution | 370 | 440 |
| Calcofluor White | 440 | 500-520 |
| Calcofluor White ABT Solution | 380 | 475 |
| Calcofluor White Standard Solution | 365 | 435 |
| 5-(and 6-)carboxy SNARF-1 indicator 576(high pH) 635(high pH) 6-Carboxyrhodamine 6G | 548(low pH) 587(low pH) 525 | 555 |
| Cascade Blue | 400 | 425 |
| Catecholamine | 410 | 470 |
| Chinacrine | 450-490 | 515 |
| CL-NERF 514(high pH) 540(high pH) Coriphosphine O | 504(low pH) 587(low pH) 460 | 575 |
| Coumarin-Phalloidin | 387 | 470 |
| CY3.18 | 554 | 568 |
| CY5.18 | 649 | 666 |
| CY7 | 710 | 805 |
| DANS (1-DimethylAmino-Naphthaline-5-Sulphonic Acid) | 340 | 525 |
| DANSA (DiaminoNaphthyl-Sulphonic Acid) | 340-380 | 430 |
| Dansyl NH—CH₃ in water | 340 | 578 |
| DAPI | 350 | 470 |
| DiA | 456 | 590 |
| Diamino Phenyl Oxydiazole (DAO) | 280 | 460 |
| Di-8-ANEPPS | 488 | 605 |
| Dimethylamino-5-Sulphonic Acid | 310-370 | 520 |
| DiI [DiIC$_{18}$(3)] | 549 | 565 |
| DiO [DiOC$_{18}$(3)] | 484 | 501 |
| Diphenyl Brilliant Flavine 7GFF | 430 | 520 |
| DM-NERF 510(high pH) 536(high pH) Dopamine | 497(low pH) 527(low pH) 340 | 490-520 |
| ELF-97 alcohol | 345 | 530 |
| Eosin | 525 | 545 |
| Erythrosin ITC | 530 | 558 |
| Ethidium Bromide | 510 | 595 |
| Euchrysin | 430 | 540 |
| FIF (Formaldehyde Induced Fluorescence) | 405 | 435 |
| Flazo Orange | 375-530 | 612 |
| Fluorescein | 494 | 518 |
| Fluorescein Iso-thiocyanate (FITC) | 490 | 525 |
| Fluo 3 | 485 | 503 |
| FM1-43 | 479 | 598 |
| Fura-2 | 335(high [Ca$^{2+}$]) | 363(low [Ca$^{2+}$]) 512(low [Ca$^{2+}$]) |
| Fura Red | 505(high [Ca$^{2+}$]) 436(high [Ca$^{2+}$]) 637(high [Ca$^{2+}$]) | 472(low [Ca$^{2+}$]) 657(low [Ca$^{2+}$]) |
| Genacryl Brilliant Red B | 520 | 590 |
| Genacryl Brilliant Yellow 10GF | 430 | 485 |
| Genacryl Pink 3G | 470 | 583 |
| Genacryl Yellow 5GF | 430 | 475 |
| Gloxalic Acid | 405 | 460 |
| Granular Blue | 355 | 425 |
| Haematoporphyrin | 530-560 | 580 |
| Hoechst 33258, 33342 (Bound to DNA) | 352 | 461 |
| 3-Hydroxypyrene-5,-8,10-TriSulfonic Acid | 403 | 513 |
| 7-Hydroxy-4-methylcoumarin | 360 | 455 |
| 5-Hydroxy-Tryptamine (5-HT) | 380-415 | 520-530 |
| Indo-1 | 350 | 405-482 |
| Intrawhite Cf Liquid | 360 | 430 |
| Leucophor PAF | 370 | 430 |
| Leucophor SF | 380 | 465 |
| Leucophor WS | 395 | 465 |
| Lissamine Rhodamine B200 (RD200) | 575 | 595 |
| Lucifer Yellow CH | 425 | 528 |
| Lucifer Yellow VS | 430 | 535 |
| LysoSensor Blue DND-192, DND-167 | 374 | 425 |
| LysoSensor Green DND-153, DND-189 | 442 | 505 |
| LysoSensor Yellow/Blue 329(high pH) 440(high pH) LysoTracker Green | 384(low pH) 540(low pH) 504 | 511 |
| LysoTracker Yellow | 534 | 551 |
| LysoTracker Red | 577 | 592 |
| Magdala Red | 524 | 600 |
| Magnesium Green | 506 | 531 |
| Magnesium Orange | 550 | 575 |
| Maxilon Brilliant Flavin 10 GFF | 450 | 495 |
| Maxilon Brilliant Flavin 8 GFF | 460 | 495 |
| Mitotracker Green FM | 490 | 516 |
| Mitotracker Orange CMTMRos | 551 | 576 |
| MPS (Methyl Green Pyronine Stilbene) | 364 | 395 |
| Mithramycin | 450 | 570 |
| NBD | 465 | 535 |
| NBD Amine | 450 | 530 |
| Nile Red | 515-530 | 525-605 |
| Nitrobenzoxadidole | 460-470 | 510-650 |
| Noradrenaline | 340 | 490-520 |
| Nuclear Fast Red | 289-530 | 580 |
| Nuclear Yellow | 365 | 495 |
| Nylosan Brilliant Flavin E8G | 460 | 510 |
| Oregon Green 488 fluorophore | 496 | 524 |
| Oregon Green 500 fluorophore | 503 | 522 |
| Oregon Green 514 fluorophore | 511 | 530 |
| Pararosaniline (Feulgen) | 570 | 625 |
| Phorwite AR Solution | 360 | 430 |
| Phorwite BKL | 370 | 430 |
| Phorwite Rev | 380 | 430 |
| Phorwite RPA | 375 | 430 |
| Phosphine 3R | 465 | 565 |
| Phosphine R | 480-565 | 578 |
| Pontochrome Blue Black | 535-553 | 605 |
| POPO-1, PO-PRO-1 | 434 | 456 |
| Primuline | 410 | 550 |
| Procion Yellow | 470 | 600 |
| Propidium Iodide | 536 | 617 |
| Pyronine | 410 | 540 |
| Pyronine B | 540-590 | 560-650 |
| Pyrozal Brilliant Flavin 7GF | 365 | 495 |

TABLE 1-continued

| Fluorochrome | Excitation Wavelength | Emission Wavelength |
|---|---|---|
| Quinacrine Mustard | 423 | 503 |
| R-phycoerythrin | 565 | 575 |
| Rhodamine 110 | 496 | 520 |
| Rhodamine 123 | 511 | 534 |
| Rhodamine 5 GLD | 470 | 565 |
| Rhodamine 6G | 526 | 555 |
| Rhodamine B | 540 | 625 |
| Rhodamine B 200 | 523-557 | 595 |
| Rhodamine B Extra | 550 | 605 |
| Rhodamine BB | 540 | 580 |
| Rhodamine BG | 540 | 572 |
| Rhodamine Green fluorophore | 502 | 527 |
| Rhodamine Red | 570 | 590 |
| Rhodamine WT | 530 | 555 |
| Rhodol Green fluorophore | 499 | 525 |
| Rose Bengal | 540 | 550-600 |
| Serotonin | 365 | 520-540 |
| Sevron Brilliant Red 2B | 520 | 595 |
| Sevron Brilliant Red 4G | 500 | 583 |
| Sevron Brilliant Red B | 530 | 590 |
| Sevron Orange | 440 | 530 |
| Sevron Yellow L | 430 | 490 |
| SITS (Primuline) | 395-425 | 450 |
| SITS (Stilbene Isothiosulphonic Acid) | 365 | 460 |
| Sodium Green | 507 | 535 |
| Stilbene | 335 | 440 |
| Snarf 1 | 563 | 639 |
| Sulpho Rhodamine B Can C | 520 | 595 |
| Sulpho Rhodamine G Extra | 470 | 570 |
| SYTOX Green nucleic acid stain | 504 | 523 |
| SYTO Green fluorescent nucleic acid stains | 494 ± 6 | 515 ± 7 |
| SYTO Green fluorescent nucleic acid stains | 515 ± 7 | 543 ± 13 |
| SYTO 17 red fluorescent nucleic acid stain | 621 | 634 |
| Tetracycline | 390 | 560 |
| TRITC (Tetramethyl Rhodamine Isothiocyanate) | 557 | 576 |
| Texas Red | 596 | 615 |
| Thiazine Red R | 510 | 580 |
| Thioflavin S | 430 | 550 |
| Thioflavin TCN | 350 | 460 |
| Thioflavin 5 | 430 | 550 |
| Thiolyte | 370-385 | 477-484 |
| Thiozol Orange | 453 | 480 |
| Tinopol CBS | 390 | 430 |
| TOTO 1, TO-RRO-1 | 514 | 533 |
| TOTO 3, TO-PRO-3 | 642 | 661 |
| True Blue | 365 | 420-430 |
| Ultralite | 656 | 678 |
| Uranine B | 420 | 520 |
| Uvitex SFC | 365 | 435 |
| X-Rhodamine | 580 | 605 |
| Xylene Orange | 546 | 580 |
| XRITC | 582 | 601 |
| YOYO-1, YOYO-PRO-1 | 491 | 509 |
| YOYO-3, YOYO-PRO-3 | 612 | 613 |

One or more different populations of spectrally encoded cells can be created, each population comprising one or more different semiconductor nanocrystals. Different populations of the cells, and thus different assays, can be blended together, and the assay can be performed in the presence of the blended populations. The individual cells are scanned for their spectral properties, which allows the spectral code to be decoded and thus identifies the cell. Because of the large number of different semiconductor nanocrystals and combinations thereof which can be distinguished, large numbers of different encoded cells can be simultaneously interrogated.

"Optional" or "optionally" means that the subsequently described event or circumstance may or may not occur, and that the description includes instances where the event or circumstance occurs and instances in which it does not. For example, the phrase "optionally surrounded by a 'coat' of an organic capping agent" with reference to an SCNC includes SCNCs having such a coat, and SCNCs lacking such a coat.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As explained above, the present invention pertains to methods of encoding cells with SCNCs and related species and uses of the encoded cells. In order to further an understanding of the invention, a more detailed discussion is provided below regarding SCNCs for use in the subject methods, as well as detailed descriptions of providing encoded cells and uses of the encoded cells.

Production of SCNCs

SCNCs can be made from any material and by any technique that produces SCNCs having emission characteristics useful in the methods, articles and compositions taught herein. The SCNCs have absorption and emission spectra that depend on their size, size distribution and composition. Suitable methods of production are disclosed in, e.g., U.S. Pat. Nos. 6,576,291; 6,207,229; 6,048,616; 5,990,479; 5,690,807; 5,505,928; 5,262,357; PCT Publication No. WO 99/26299 (published May 27, 1999; inventors Bawendi et al.), the disclosures of all of said patents and publications incorporated herein by reference in their entireties. Other suitable methods of manufacture are described in, e.g., Murray et al. (1993) *J. Am. Chem. Soc.* 115:8706-8715; Guzelian et al. (1996) *J. Phys. Chem.* 100:7212-7219; Peng et al. (2001) *J. Am. Chem. Soc.* 123:183-184; Hines et al. (1996) *J. Phys. Chem.* 100: 468; Dabbousi et al. (1997) *J. Phys. Chem. B* 101:9463; Peng et al. (1997) *J. Am. Chem. Soc.* 119:7019; Peng et al. (1998) *J. Am. Chem. Soc.* 120:5343; and Qu et al. (2001) *Nano Lett.* 1:333-337.

Examples of materials from which SCNCs can be formed include group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, Pb, Ge, Si, and other materials such as PbS, PbSe, and mixtures of two or more semiconducting materials, and alloys of any semiconducting material(s).

The composition, size and size distribution of the semiconductor nanocrystals affect their absorption and emission spectra. Exemplary SCNCs that emit energy in the visible range include CdS, CdSe, CdTe, ZnSe, ZnTe, GaP, and GaAs. Exemplary SCNCs that emit energy in the near IR range include InP, InAs, InSb, PbS, and PbSe. Exemplary SCNCs that emit energy in the blue to near-ultraviolet include ZnS and GaN. The size of SCNCs in a given population can be determined by the synthetic scheme used and/or through use of separation schemes, including for example size-selective precipitation and/or centrifugation. The separation schemes can be employed at an intermediate step in the synthetic scheme or after synthesis has been completed. For a given composition, larger SCNCs absorb and emit light at longer wavelengths than smaller SCNCs. SCNCs absorb strongly in the visible and UV and can be excited efficiently at wavelengths shorter than their emission peak. This characteristic allows the use in a mixed population of SCNCs of a single excitation source to excite all the SCNCs if the source has a shorter wavelength than the shortest SCNC emission wavelength within the mixture; it also confers the ability to selectively excite subpopulation(s) of SCNCs within the mixture by judicious choice of excitation wavelength.

The surface of the SCNC is preferably modified to enhance emission efficiency by adding an overcoating layer to form a "shell" around the "core" SCNC, because defects in the surface of the core SCNC can trap electrons or holes and degrade its electrical and optical properties. Addition of an insulating shell layer removes nonradiative relaxation pathways from the excited core, resulting in higher luminescence efficiency. Suitable materials for the shell include semiconductor materials having a higher bandgap energy than the core and preferably also having good conductance and valence band offset. Thus, the conductance band of the shell is desirably of a higher energy and the valence band is desirably of a lower energy than those of the core. For SCNC cores that emit energy in the visible (e.g., CdS, CdSe, CdTe, ZnSe, ZnTe, GaP, GaAs) or near IR (e.g., InP, InAs, InSb, PbS, PbSe), a material that has a bandgap energy in the ultraviolet may be used for the shell, for example ZnS, GaN, and magnesium chalcogenides, e.g., MgS, MgSe, and MgTe. For an SCNC core that emits in the near IR, materials having a bandgap energy in the visible, such as CdS or CdSe, or the ultraviolet may be used. Preparation of core-shell SCNCs is described in, e.g., Dabbousi et al. (1997) *J. Phys. Chem. B* 101:9463; Kuno et al. (1997) *J. Phys. Chem.* 106:9869; Hines et al. (1996) *J. Phys. Chem.* 100:468; PCT Publ. No. WO 99/26299; and U.S. Pat. No. 6,207,229 to Bawendi et al. issued Mar. 27, 2001. The SCNCs can be made further luminescent through overcoating procedures as described in Danek et al. (1996) *Chem. Mat.* 8(1):173-180, and Peng et al. (1997) *J. Am. Chem. Soc.* 119:7019-7029.

In a preferred embodiment, the nanocrystals are used in a core/shell configuration wherein a first semiconductor nanocrystal forms a core ranging in diameter, for example, from about 20 Å to about 100 Å, with a shell of another semiconductor nanocrystal material grown over the core nanocrystal to a thickness of, for example, 1-10 monolayers in thickness. In a preferred embodiment, a 1-10 monolayer thick shell of CdS is epitaxially grown over a core of CdSe.

Most SCNCs are typically prepared in coordinating solvent, such as TOPO and trioctyl phosphine (TOP), resulting in the formation of a passivating organic layer on the surface of SCNCs with and without a shell. Such passivated SCNCs can be readily solubilized in organic solvents, for example toluene, chloroform and hexane. Molecules in the passivating layer can be displaced or modified to provide an outermost coating that adapts the SCNCs for use in other solvent systems, for example aqueous systems.

Alternatively, an outermost layer of an inorganic material such as silica can be added around the shell to improve the aqueous dispersibility of the SCNCs, and the surface of the silica can optionally be derivatized (Bruchez et al. (1998), supra). See, also, U.S. Pat. No. 6,649,138 for methods of making water-dispersible SCNCs, incorporated herein by reference in its entirety.

A displacement reaction may also be employed to modify the SCNC to improve the solubility in a particular organic solvent. For example, if it is desired to associate the SCNCs with a particular solvent or liquid, such as pyridine, the surface can be specifically modified with pyridine or pyridine-like moieties which are soluble or miscible with pyridine to ensure solvation. Water-dispersible SCNCs can be prepared as described in U.S. Pat. No. 6,251,303 to Bawendi et al. and PCT Publ. No. WO 00/17655, published Mar. 30, 2000.

The surface layer of the SCNCs may be modified by displacement to render the SCNC reactive for a particular coupling reaction. For example, displacement of trioctylphosphine oxide (TOPO) moieties with a group containing a carboxylic acid moiety enables the reaction of the modified SCNCs with amine containing moieties to provide an amide linkage. For a detailed description of these linking reactions, see, e.g., U.S. Pat. No. 5,990,479 to Weiss et al.; Bruchez et al. (1998), supra, Chan et al. (1998), supra, Bruchez "Luminescent SCNCs: Intermittent Behavior and use as Fluorescent Biological Probes" (1998) *Doctoral dissertation*, University of California, Berkeley, and Mikulec "SCNC Colloids: Manganese Doped Cadmium Selenide, (Core) Shell Composites for Biological Labeling, and Highly Fluorescent Cadmium Telluride" (1999) *Doctoral dissertation*, Massachusetts Institute of Technology. The SCNC may be conjugated to other moieties directly or indirectly through a linker.

Examples of suitable spacers or linkers are polyethylene glycols, dicarboxylic acids, polyamines and alkylenes. The spacers or linkers are optionally substituted with functional groups, for example hydrophilic groups such as amines, carboxylic acids and alcohols or lower alkoxy group such as methoxy and ethoxy groups. Additionally, the spacers will have an active site on or near a distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., *Solid Phase Peptide Synthesis*, IRL Press (1989).

The Cell

The cell(s) used in the methods described herein can be of any origin, including from prokaryotes, eukaryotes, or archeons. The cell(s) may be living or dead. If obtained from a multicellular organism, the cell may be of any cell type. The cell(s) may be a cultured cell line or a primary isolate, the cell(s) may be mammalian, amphibian, reptilian, plant, yeast, bacterium, spirochetes, or protozoan. The cell(s) may be, for example, human, murine, rat, hamster, chicken, quail, goat or dog. The cell may be a normal cell, a mutated cell, a genetically manipulated cell, a tumor cell, etc.

Exemplary cell types from multicellular organisms include acidophils, acinar cells, pinealocytes, adipocytes, ameloblasts, astrocytes, basal (stem) cells, basophils, hepatocytes, neurons, bulging surface cells, C cells, cardiac muscle cells, centroacinar cells, chief cells, chondrocytes, Clara cells, columnar epithelial cells, corpus luteal cells, decidual cells, dendrites, endrocrine cells, endothelial cells, enteroendocrine cells, eosinophils, erythrocytes, extraglomerular mesangial cells, fetal fibroblasts, fetal red blood cells, fibroblasts, follicular cells, ganglion cells, giant Betz cells, goblet cells, hair cells, inner hair cells, type I hair cells, hepatocytes, endothelial cells, Leydig cells, lipocytes, liver parenchymal cells, lymphocytes, lysozyme-secreting cells, macrophages, mast cells, megakaryocytes, melanocytes, mesangial cells, monocytes, myoepithelial cells, myoid cells, neck mucous cells, nerve cells, neutrophils, oligodendrocytes, oocytes, osteoblasts, osteochondroclasts, osteoclasts, osteocytes, pillar cells, sulcal cells, parathyroid cells, parietal cells, pepsinogen-secreting cells, pericytes, pinealocytes, pituicytes, plasma cells, platelets, podocytes, spermatocytes, Purkinje cells, pyramidal cells, red blood cells, reticulocytes, Schwann cells, Sertoli cells, columnar cells, skeletal muscle cells, smooth muscle cells, somatostatin cells, enteroendocrine cells, spermatids, spermatogonias, spermatozoas, stellate cells, supporting Deiter cells, support Hansen cells, surface cells, surface epithelial cells, surface mucous cells, sweat gland cells, T lymphocytes, theca lutein cells, thymocytes, thymus epithelial cell, thyroid cells, transitional epithelial cells, type I pneumonocytes, and type II pneumonocytes.

Exemplary types of tumor cells include adenomas, carcinomas, adenocarcinomas, fibroadenomas, ameloblastomas, astrocytomas, mesotheliomas, cholangiocarcinomas, cholangiofibromas, cholangiomas, chondromas, chondrosarcomas, chordomas, choriocarcinomas, craniopharyngiomas, cystadenocarcinomas, cystadenomas, dysgerminomas, ependymomas, epitheliomas, erythroid leukemias, fibroadenomas, fibromas, fibrosarcomas, gangliogliomas, ganglioneuromas, ganglioneuroblastomas, gliomas, granulocytic leukemias, hemangiomas, hemangiopericytomas, hemangiosarcomas, hibernomas, histiocytomas, keratoacanthomas, leiomyomas, leiomyosarcomas, lipomas, liposarcomas, luteomas, lymphangiomas, lymphangiosarcomas, lymphomas, medulloblastomas, melanomas, meningiomas, mesotheliomas, myelolipomas, nephroblastomas, neuroblastomas, neuromyoblastomas, odontomas, oligodendrogliomas, osteochondromas, osteomas, osteosarcomas, papillomas, paragangliomas, pheochromocytomas, pinealomas, pituicytomas, retinoblastomas, rhabdomyosarcomas, sarcomas, schwannomas, seminomas, teratomas, thecomas and thymomas.

Exemplary bacteria which may be encoded include *Staphylococcus aureus*, *Legionella pneumophila*, *Escherichia coli*, *M tuberculosis*, *S. typhimurium*, *Vibrio cholera*, *Clostridium perfringens*, *Clostridium tetani*, *Clostridium botulinum*, *Clostridium baratii*, *Clostridium difficile*, *M leprae*, *Helicobacter pylori*, *Hemophilus influenzae* type b, *Corynebacterium diphtheriae*, *Corynebacterium minutissimum*, *Bordetella pertussis*, *Streptococcus pneumoniae*, *Neisseria gonorrhoeae*, *Neisseria meningitides*, *Shigella dysenteriae*, *Pseudomonas aeruginosa*, *Bacteroides fragilis*, *Prevotella melaminogenica*, *Fusobacterium*, *Erysipelothrix rhusiopathiae*, *Listeria monocytogenes*, *Bacillus anthracis*, *Hemophilus ducreyi*, *Francisella tularensis*, *Yersinia pestis*, *Bartonella henselae*, *Klebsiella*, *Enterobacter*, *Serratia*, *Proteus*, and *Shigella*.

Exemplary spirochetes which may be encoded include *Treponema pallidum*, *T pertenue*, *T. carateum*, *Borrelia recurrentis*, *B. vincentii*, *B. burgdorferi*, and *Leptospira icterohaemorrhagiae*.

Exemplary fungi which may be encoded include *Actinomyces bovis*, Aspergillus fumigatus, Blastomyces dermatitidis, Candida albicans, Coccidioides immitis, Cryptococcus enoformans, Histoplasma capsulatum, Sporotrichum schenckii, Actinomyces israelii, Actinomyces bovis, Aspergillus fumigatus, Blastomyces dermatitidis, Candida albicans, Coccidioides immitis, Cryptococcus neoformans, Histoplasma capsulatum, Nocardia asteroides, Pneumocystis carinii, Sporothrix schenckii, Pichia pastoris, Saccharomyces cerevisiae, and *Schizosaccharomyces pombe*.

Exemplary protozoa and parasites which may be encoded include *Plasmodium falciparum*, Entamoeba histolytica, trypansomes, Leishmania, Toxpolasma gondii, Giardia lamblia, Chlamydia trachomatis.

Spectrally Encoded Cells

Semiconductor nanocrystals, other fluorescent species, or otherwise detectable species and combinations thereof can be used to spectrally encode cells either by allowing SCNCs producing a single color or mixtures of colors to associate specifically or non-specifically to the surface of the cells or to be incorporated into the cells. Populations of cells thus encoded can then be mixed with other populations of cells with different mixtures of colors encoding them. The mixed samples of encoded cells can then be decoded.

There are several methods whereby SCNCs can be used to spectrally encode cells. The SCNCs can be coated with a substance, e.g., a carboxyl or amine group-containing ligand that allows the SCNCs to be linked to the proteinaceous lipid bilayer of cells or to the surface of prokaryotic cells. This is done by mixing cells (e.g., from 1 cell to ~$10^{11}$ cells) for an appropriate period of time (e.g., about 1 minute to about 24 hours) with an appropriate concentration of SCNCs (e.g., 1 pM to 1 M). The excess SCNCs can be separated by filtering out SCNCs or centrifuging the cells at a speed slow enough to sediment the cells but not the SCNCs.

Alternatively, SCNCs can be conjugated with a specific molecule, e.g., a cell surface marker-specific antibody, that has a known affinity for a molecule on the surface of the cell and by this means the SCNCs could encode the cells by incubating cells and SCNCs. The binding partner on the surface of the cell can be an endogenous protein or a protein which is not normally endogenous to the cell, but which the cell is induced to express.

Cells can also be encoded by introducing SCNCs to the interior of the cell either by coating the SCNC with a molecule recognized by a molecule on the surface of the cell and allowing an active uptake procedure to occur (e.g., receptor mediated endocytosis), by forcing the SCNCs into the cell (by transient permeabilization or via lipid vesicles or by high speed injection), or by using a cationic polymer to facilitate transport across the cell membrane.

The encoded cells can be subjected to an assay which introduces a specific label to interact with the cells; for example, the label can be an SCNC or another fluorescent or non-fluorescent label. The specific interaction can be via receptor-ligand interactions, an adhesion molecule and its binding partner, a drug and the cellular protein to which it binds, or any other specific interaction between an entity on the cell and an introduced, labeled analyte. The labeled or unlabeled encoded cells can then be interrogated using a detection system or systems which can decode the cells and identify which cells are labeled, for example flow cytometry or another detection system described herein.

The initial mixed samples of encoded cells can then be grown in the presence or absence of a selective force (e.g., heat, ultraviolet light, osmotic stress, shear stress, selective media, a cytostatic or cytotoxic agent, and the like). After a certain growth period (for example, from 1 minute to 1 week depending on the cell type and type of assay being performed) the number of cells bearing the diluted code can be determined.

Through the use of the techniques described herein, a number of assays may be performed simultaneously in a single tube for a number of different analytes. This may be accomplished using a number of differently encoded cells in the same tube. The cells may then be categorized and detected by exposure to a 488 nm laser. The relative emission intensities of the different fluorescence channels are used to detect and classify which assay (which cell) is being measured.

The use of SCNCs greatly reduces the difficulty encountered with coding schemes using dye molecules because it allows simple and efficient classification and detection simultaneously with a single light source. The usually narrow dye molecule excitation spectra demand multiple excitation sources in order to successfully classify the dyes and their relative abundances.

Cells can be spectrally encoded through incorporation of nanoparticles, semiconductive, e.g., SCNCs, or metallic nanoparticles, or other fluorophores. The desired fluorescence characteristics of the cells may be obtained by mixing SCNCs of different sizes and/or compositions in a fixed amount and/or ratio to obtain the desired spectrum, which can be determined prior to association with the cells. Subsequent treatment of the cells (through for example covalent attachment, or passive absorption or adsorption) with the staining solution results in a material having the designed fluorescence characteristics.

A number of cell encoding or staining solutions can be prepared, each having a distinct distribution of sizes and compositions, to achieve the desired fluorescence characteristics. These solutions may be mixed in fixed proportions to arrive at a spectrum having the predetermined ratios and intensities of emission from the distinct SCNCs suspended in that solution. Upon exposure of this solution to a light source, the emission spectrum can be measured by techniques that are well established in the art. If the spectrum is not the desired spectrum, then more of the SCNC solution needed to achieve the desired spectrum can be added and the solution "titrated" to have the correct emission spectrum. These solutions may be colloidal solutions of SCNCs dispersed in a solvent, or they may be pre-polymeric colloidal solutions, which can be polymerized to form a matrix with SCNCs contained within.

The composition of the staining solution can be adjusted to have the desired fluorescence characteristics, preferably under the exact excitation source that will be used for the decoding. A multichannel auto-pipetter connected to a feedback circuit can be used to prepare an SCNC solution having the desired spectral characteristics, as described above. If the several channels of the titrater/pipetter are charged with several unique solutions of SCNCs, each having a unique excitation and emission spectrum, then these can be combined stepwise through addition of stock solutions.

Once the staining solution has been prepared, it can be used to incorporate a unique spectral code into a given cell or a cell population. The staining procedure can also be carried out in sequential steps.

In another method, the cell or the population of cells can be spectrally encoded through incorporation of microspheres or beads that make up a beadset, usually referred to as fluorospheres or fluospheres. Fluorospheres suitable for use in accordance with the invention are generally known in the art and may be obtained from manufacturers such as Spherotech and Molecular Probes. Examples of fluorospheres include blue fluorescent fluorospheres, with excitation/emission maxima of 350/440 nm, yellow-green fluorescent fluorospheres having excitation/emission maxima of 505/515 nm, red fluorescent fluorospheres having excitation/emission maxima of 580/605 nm, infrared fluorescent fluorospheres having excitation/emission maxima of 715/755 nm. Alternatively, fluorospheres having different surface functional groups for conjugation can be used in the present invention. The surface functional groups can include, for example, carboxylate, sulfate, aldyhyde-sulfate, amine, and the like. In addition, fluorospheres labeled with biotin, streptavidin, avidin, neutravidin, protein A, or the like can also be used for encoding the cells for use in the invention.

In another method, the cell or the population of cells can be spectrally encoded through incorporation of colloidal rod particles, also referred to as nanoparticles, nanorods, or nanobars. Typically, nanobar codes have a plurality of segments with the entire width of the nanobar particle being about 30 nm to about 1,000 nanometers, and length being about 1 to 15 microns. Nanobar codes are usually composed of two or more different materials, such as metal, metal chalcogenide, metal oxide, metal alloy, a semiconductor, or an organic or inorganic material. The method of manufacture of colloidal rod particles as nanobar codes is described in PCT publications WO 01/25002 and WO 01/25510. In general, the nanobar code particles are manufactured by electrochemical deposition in an alumina or polycarbonate template, followed by template dissolution, or by alternating electrochemical reduction of metal ions. The cell or the population of cells can then be spectrally encoded with nanobars using the methods described in detail above.

In another method of spectrally encoding the cells or population of cells, light scattering metallic particles of nanometer size onto which Raman-active moieties are adsorbed or attached are used, and the cells thus encoded are then detected by surface-enhanced Raman scattering (SERS). The metal particles can be made from a SERS active metal such as silver, gold, copper, lithium, aluminum, platinum, palladium, or the like. In addition, the particles can be in a core-shell configuration, e.g., a gold "core" encased in a silver "shell" (see, e.g., Freeman et al. (1996) *J. Phys. Chem.* 100:718-724). Furthermore, the particles can be composites of two or more metals. Preferably, the metal particle is a silver particle, a gold particle or a gold core-silver shell particle.

The colloids can be prepared from a reduction of a soluble precursor, for example, a metal salt in aqueous or solvent environment, by controlled addition of a colloid-generating agent such as citrate or borohydride, or by other conventional comminution techniques. See, e.g., Lee et al. (1982) *J. Phys. Chem.* 86:3391. The size of the colloids can be between about 2 and 150 nm, preferably between about 5 and 100 nm, more preferably between about 20 and 100 nm. The reduction can be carried out over a temperature range from 0° C. to 100° C. The SERS or SERRS active structures can also be an aggregate of the aforementioned particles. Both single particle and aggregates of particles that exhibit SERS or SERRS activity will be referred to as SERS colloids.

A Raman-active tag is adsorbed to the surface of the SERS colloid. The Raman-active tag can be any chemical molecule or portion thereof that exhibits a characteristic Raman spectrum and is capable of adsorbing or binding to a SERS colloid. The tag can be a dye or pigment and/or can be, for example, a nitrile, a pyridine, an imidazole, a pyrrole, an isonitrile, a thiocyanate, a urea, an isourea, a carbamate, a thiocarbamate, an imide, a thiol, an amine, an amide, a carbonate, a carbonyl or a carboxylate. See, also, Rahman et al. (1998) *J. Org. Chem.* 63:6196-6199, for additional Raman-active moieties. The tag can have a Raman-active mode relative to the excitation light source in the range of between about 100 to 5000 $cm^{-1}$, preferably between about 1000-5000 $cm^{-1}$ and, more preferably, between about 1000-2500 $cm^{-1}$. SERRS-active particles can be used that have a suitable electronic transition such that the excitation light source is chosen to emit light having a frequency close to that of the electronic transition and/or the frequency of the SERS plasmon resonance of the SERS particle.

Methods by which Raman-active moieties can be adsorbed or bound to the surface of the particle are well known in the art. See, e.g., EP 0806460(A1). Thus, for example, the Raman-active tag may be added to the medium containing the SERS colloid as a solid or as a solution. It can be added before, during or after the reduction of the soluble metal precursor. The amount of Raman-active tag can be added to provide between about 1 and 1,000,000, preferably between about 10 and 10,000, more preferably between about 10 and 100 Raman-active tags on each particle. The cell or the population of cells can then be spectrally encoded with SERS and/or SERRS particle using the methods described in detail herein.

Spectrally encoding cells can be effected by any combination of the above described methods and detectable species.

Attaching SCNCs to Cells

The SCNCs can be attached to the cells by covalent attachment as well as by entrapment, or can be coupled to one member of a binding pair the other member of which is attached to the cells. For instance, SCNCs are prepared by a number of techniques that result in reactive groups on the surface of the SCNC. See, e.g., Bruchez et al. (1998) *Science* 281:2013-2016, Chan et al. (1998) *Science* 281:2016-2018, Colvin et al. (1992) *J. Am. Chem. Soc.* 114:5221-5230, Katari et al. (1994) *J. Phys. Chem.* 98:4109-4117, Steigerwald et al. (1987) *J. Am. Chem. Soc.* 110:3046. The reactive groups present on the surface of the SCNCs can be coupled to reactive groups present on the cell. For example, SCNCs which have carboxylate groups present on their surface can be coupled to cells with amine groups using a carbodiimide activation step.

Any cross-linking method that links a SCNC to a cell and does not adversely affect the properties of the SCNC or the cell can be used. In a cross-linking approach, the relative amounts of the different SCNCs can be used to control the relative intensities, while the absolute intensities can be controlled by adjusting the reaction time to control the number of reacted sites in total. After the cells are crosslinked to the SCNCs, the cells are optionally rinsed to wash away unreacted SCNCs.

A sufficient amount of fluorophore must be used to encode the cells so that the intensity of the emission from the fluorophores can be detected by the detection system used and the different intensity levels must be distinguishable, where intensity is used in the coding scheme but the fluorescence emission from the SCNCs or other fluorophores used to encode the cells must not be so intense to as to saturate the detector used in the decoding scheme.

Where intact cellular structures are desired, the methods used to encode the cells cause minimal disruption of the viability of the cell and of the integrity of membranes. Alternatively, the cells can be fixed and treated with routine histochemical or cytochemical procedures. A fixative that does not affect the encoding should be used.

Semiconductor nanocrystals of varying core sizes (10-150 angstroms), composition and/or size distribution can be conjugated to a specific-binding molecule which bind specifically to a molecule on a cell membrane or within a cell. Any specific "anti-molecule" can be used, for example, an antibody, an immunoreactive fragment of an antibody, and the like. Preferably, the anti-molecule is an antibody. The semiconductor nanocrystal conjugates are used to associate the SCNC with the cell or, once within the cell, to identify intracellular components, organelles, molecules or the like.

More specifically, the specific-binding molecule may be derived from polyclonal or monoclonal antibody preparations, may be a human antibody, or may be a hybrid or chimeric antibody, such as a humanized antibody, an altered antibody, F(ab')$_2$ fragments, F(ab) fragments, Fv fragments, a single-domain antibody, a dimeric or trimeric antibody fragment construct, a minibody, or functional fragments thereof which bind to the analyte of interest. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, polyclonal antibodies are generated by immunizing a suitable animal, such as a mouse, rat, rabbit, sheep or goat, with an antigen of interest. In order to enhance immunogenicity, the antigen can be linked to a carrier prior to immunization. Such carriers are well known to those of ordinary skill in the art.

Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2-6 weeks later with one or more injections of the antigen in saline, preferably using Freund's incomplete adjuvant. Antibodies may also be generated by in vitro immunization, using methods known in the art. Polyclonal antiserum is then obtained from the immunized animal.

Monoclonal antibodies are generally prepared using the method of Kohler and Milstein (1975) *Nature* 256:495-497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

Human monoclonal antibodies are obtained by using human rather than murine hybridomas. See, e.g., Cote, et al. *Monclonal Antibodies and Cancer Therapy*, Alan R. Liss, 1985, p. 77.

Monoclonal antibodies or portions thereof may be identified by first screening a B-cell cDNA library for DNA molecules that encode antibodies that specifically bind to p185, according to the method generally set forth by Huse et al. (1989) *Science* 246:1275-1281. The DNA molecule may then be cloned and amplified to obtain sequences that encode the antibody (or binding domain) of the desired specificity.

As explained above, antibody fragments which retain the ability to recognize the molecule of interest, will also find use in the subject invention. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as F$_v$. See, e.g., Inbar et al. (1972) *Proc. Nat.*

Acad. Sci. USA 69:2659-2662; Hochman et al. (1976) Biochem 15:2706-2710; and Ehrlich et al. (1980) Biochem 19:4091-4096.

A single-chain Fv ("sFv" or "scFv") polypeptide is a covalently linked $V_H$-$V_L$ heterodimer which is expressed from a gene fusion including $V_H$- and $V_L$-encoding genes linked by a peptide-encoding linker. Huston et al. (1988) Proc. Nat. Acad. Sci. USA 85:5879-5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al. (1988) Proc. Nat. Acad. Sci. USA 85:5879-5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al. (1992) Biochem 31:1579-1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) J Immunology 149B:120-126.

Introduction of the SCNCs into the Cell

In general, transfer methods into cells can be divided into three categories: physical (e.g., electroporation, direct transfer, and particle bombardment), chemical (e.g., proteinoids, microemulsions, and liposomes), and biological (e.g., virus-derived vectors, receptor-mediated uptake, phagocytosis). Derivatizing a ligand for a cellular receptor which is endocytosed with an agent acts as a means to ferry that agent into the cell.

The procedure for attaching an agent such as an SCNC to a ligand varies according to the chemical structure of the ligand. Generally, the ligand contains a variety of functional groups which are available for reaction with a suitable functional group on a biologically active molecule to bind the agent thereto. Alternatively, the ligand and/or agent may be derivatized to expose or attach additional reactive functional groups. The derivatization may involve attachment of any of a number of linker molecules such as those available from Pierce Chemical Company, Rockford Ill.

A linker can be used to join, covalently or noncovalently, the ligand and agent. Suitable linkers are well known to those of skill in the art and include, but are not limited to, straight or branched-chain carbon linkers, heterocyclic carbon linkers, or peptide linkers. See, e.g., Birch and Lennox, Monoclonal Antibodies: Principles and Applications, Chapter 4, Wiley-Liss, New York, N.Y. (1995); U.S. Pat. Nos. 5,218,112 and 5,090,914; Hermanson (1996) Bioconjugate Techniques, Academic Press, San Diego, Calif.

A bifunctional linker having one functional group reactive with a group on a particular agent, and another group reactive with a ligand, may be used to form the desired conjugate. Alternatively, derivatization may involve chemical treatment of the ligand and/or agent; e.g., glycol cleavage of a sugar moiety with periodate to generate free aldehyde groups. The free aldehyde groups may then be reacted with free amine or hydrazine groups on an agent to bind the agent thereto. See, U.S. Pat. No. 4,671,958. Procedures for generation of free sulfhydryl groups on antibodies or antibody fragments are also known. See, U.S. Pat. No. 4,659,839. Many procedures and linker molecules for attachment of proteins to other molecules are known. See, e.g., European Patent Application No. 188,256; U.S. Pats. Nos., 4,671,958, 4,659,839, 4,414,148, 4,699,784; 4,680,338; 4,569,789; and 4,589,071; and Borlinghaus et al. (1987) Cancer Res. 47:4071-4075.

Conjugates comprising cleavable linkages may be used. Cleaving of the linkage to release the agent from the ligand and/or linker may be prompted by enzymatic activity or conditions to which the conjugate is subjected. The cis-aconitic acid spacer can be used to release the agent from the ligand in endosomes. Disulfide linkages are also cleavable in the reducing environment of the endosomes.

A number of different cleavable linkers are known to those of skill in the art. See U.S. Pats. Nos. 4,618,492; 4,542,225, and 4,625,014. The mechanisms for release of an agent from these linker groups include, for example, irradiation of a photolabile bond and acid-catalyzed hydrolysis. U.S. Pat. No. 5,141,648 discloses conjugates comprising linkers of specified chemical structure, wherein the linkage is cleaved in vivo thereby releasing the attached compound. The linker is susceptible to cleavage at a mildly acidic pH, and is believed to be cleaved during transport into the cytoplasm of a target cell, thereby releasing the agent inside a target cell. U.S. Pat. No. 4,671,958 includes a description of conjugates comprising linkers which are cleaved by proteolytic enzymes of the complement system.

Alternatively, methods may be used to transport SCNCs out of the endosome. A number of suitable methods are known in the art. SCNC bound to a ligand which binds specifically to the polymeric immunoglobulin receptor can be used for efficient introduction into cells. Ferkol et al. (1993) J. Clin. Invest. 92:2394-2400; and Ferkol et al. (1995) J. Clin. Invest. 95:493-502. As an example, SCNC may be linked to ricin A, which is capable of penetrating the endosomal membrane into the cytosol. Beaumell et al. (1993) J. Biol. Chem. 268:23661-23669.

Nonlimiting examples of artificial means for transporting SCNCs across cell membranes include action of chemical agents such as detergents, enzymes or adenosine triphosphate; receptor- or transport protein-mediated uptake; liposomes or alginate hydrogels; phagocytosis; pore-forming proteins; microinjection; electroporation; hypoosmotic shock; or minimal physical disruption such as scrape loading, patch clamp methods, or bombardment with solid particles coated with or in the presence of the SCNCs of the invention.

These techniques include transfection, infection, biolistic impact, electroporation, microinjection, scraping, or any other method which introduces the gene of interest into the host cell (see, U.S. Pat. No. 4,743,548, 4,795,855, 5,068,193, 5,188,958, 5,463,174, 5,565,346 and No. 5,565,347).

One method for introducing SCNCs into cells involves the use of micelles and liposomes. Micelles can be formed in aqueous solution by the use of micelle forming agents such as emulsifying agents, cholic acid and derivatives thereof, phosphatides, detergents, cationic lipids, and the like. Emulsifying agents include, for example, those marketed under the tradenames Cremophore EL, the Tweens, and the pluronics. Cholic acid and its derivatives include the trihydroxycholic acids, such as glyocholic acid, taurocholic acids, and their salts. Phosphatides for use in the invention include especially those that contain at least one saturated fatty acid residue that is branched, such as glycerol where two of the hydroxyl groups are esterified with residues from saturated fatty acids of $C_{10-20}$ where at least one of the carbon atoms has an alkyl group. Examples of such phosphatides includes, for example, 1,2-di(8-methylheptadecanoyl)-sn-glycero-3-phosphocholine, 1,2-di(10-methylstearoyl)-sn-glycero-3-phosphocholine, 1,2-(10-methylnonadecanoyl)-sn-glycero-3-phosphocholine, and the like. As will be evident to one of skill in the art, other compounds may also be added to the micelle forming agents, such as a lipoid component, bile acid salts, dihexanoyl lecithin, and the like.

SCNCs can be introduced into cells using transfection by micelle-based or liposome-based methods. Conjugated or unconjugated SCNCs in solution (about 1 fm to about 10 mM) are mixed with a micelle forming agent or any other species that can be used to form effective micelles or liposomes, at various concentrations to form SCNC trapped in the micelles. The solution containing the SCNCs trapped in the micelles can then be added to mammalian or other eukaryotic or prokaryotic cells, wherein the lipid and SCNC compositions and concentrations are varied, the micelle forming agent:SCNC ratio is varied, the cell density is varied and the time of exposure to the SCNC trapped in the micelles or liposomes is varied (e.g., from 1 minute to 48 hours) to determine the optimum transfection conditions. The efficacy of introduction of such SCNCs into cells can be assessed by standard epi-fluorescent microscopy or by any other detection system utilizing the broadband excitation and flexible emission spectra of SCNCs.

Useful liposomes include cationic phospholipids, neutral phospholipids, lipids and mixtures thereof. Additional components may be included, such as targeting peptides or proteins, fusion peptides (e.g., from Sendai virus, influenza virus, hemagluttinating virus of Japan (HVJ)), envelope proteins of viruses, polycationic substances such as poly-L-lysine or DEAE-dextran, molecules which bind to the surface of airway epithelial cells including antibodies, adhesion molecules and growth factors, and the like.

The SCNC can be formulated as an SCNC-liposome complex formulation. Such complexes comprise a mixture of lipids which bind to the SCNC or a ligand attached to the SCNC, providing a hydrophobic coat which allows the agent to be delivered into cells. Liposomes that can be used include DOPE (dioleoyl phosphatidyl ethanol amine) and CUDMEDA (N-(5-cholestrum-3-ol 3-urethanyl)-N',N'-dimethylethylene diamine). Cationic liposomes which may be used in the present invention include 3-[N-(N',N'-dimethyl-aminoethane)-carbamoyl]-cholesterol (DC-Chol), N,N,N-trimethyl-2,3-bis((1-oxo-9-octadecenyl)oxy)-(Z,Z)-1-propanaminium methyl sulfate (DOTAP), lipopolyamines such as lipospermine (DOGS), (+/−)—N-(2-hydroxyethyl)-N,N-dimethyl-2,3-bis(dodecyloxy)-1-propanaminium bromide (DLRIE), DOTMA, DOSPA, DMRIE, GL-67, GL-89, Lipofectin, and Lipofectamine (Thiery et al. (1997) *Gene Ther.* 4:226-237; Feigner et al., (1995) *Annals N.Y. Acad. Sci.* 772:126-139; Eastman et al. (1997) *Hum. Gene Ther.* 8:765-773). Also encompassed are the cationic phospholipids described in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol or DC-cholesterol may also be included.

For preparing liposomes, the procedure described by Kato et al. (1991) *J. Biol. Chem.* 266:3361 may be used. Briefly, the lipids and lumen composition containing the SCNC are combined in an appropriate aqueous medium, conveniently a saline medium where the total solids is in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Figure 4:
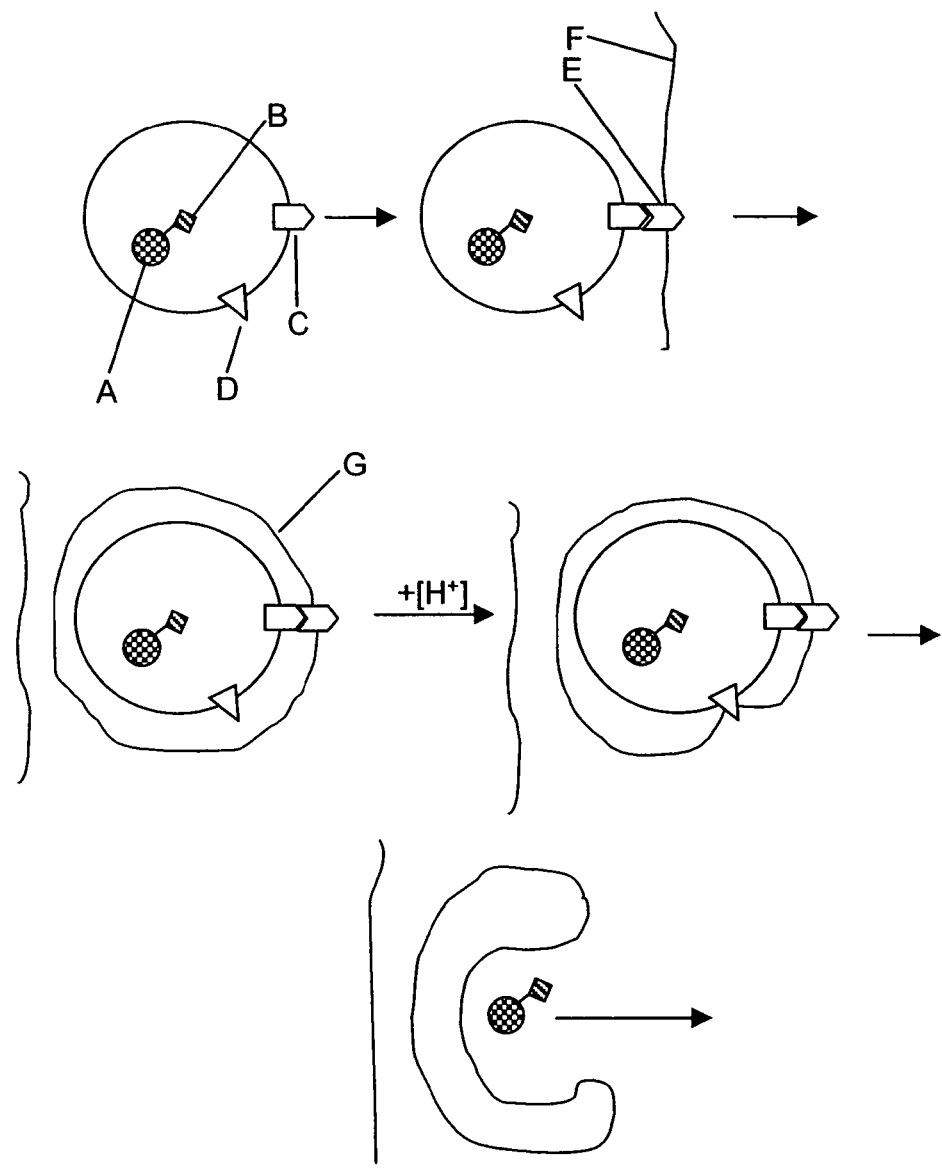
FIG. 4 is a pictorial representation illustrating a method for introducing SCNCs into live cells in which the SCNC is enclosed in a liposome which contains proteins to trigger receptor mediated endocytosis and acid-induced fusogenic proteins.

The process of receptor-mediated endocytosis results in the contents of an endosome fusing with liposomes and their subsequent degradation. Certain viruses (e.g., Semliki forest virus) avoid being transported to liposomes by being released from the endosome prior to endosome-lysosome fusion. These viruses behave in this manner because proteins in the viral coat (e.g., hemagglutinin) are induced to cause fusion and release of viral particles in the acidic environment of the endosomes. Thus, SCNCs and proteins to trigger receptor-mediated endocytosis can be enclosed in liposomes, thereby permitting acid-induced fusogenic proteins to be introduced into cells (FIG. 4). SCNC conjugates with a proteins or peptides of interest (e.g., the signal transduction domains of a receptor) can be entrapped within lipsomes using standard techniques. The lipsomes bilayers have proteins incorporated therein or attracted to their surface using methods already described. The proteins associated with liposome membrane can include a ligand train to induce receptor-mediated endocytosis (e.g., transferrin) and proteins that induce fusion to the endosome under acidic conditions e.g., hemagglutinin, or some portion of such a proteins that is sufficient to generate its activity. The ligand used for receptor-mediated endocytosis can also act as a specific cell-targeting agent when introducing the lipsomes to mixed cell cultures or in whole organisms or in mixed blood cell or tissue cell populations. The SCNC-liposome can then be added to a population of cells and will be taken up and deposited into the cytoplasm of the target cells. Liposomes could be loaded with multiple SCNC conjugates and the cells subsequently treated in the appropriate manner and the localization of each type of SCNC analyzed microscopically.

SCNCs can also be incorporated into cells using an artificial viral envelope, either alone or in combination with other materials. Artificial membranes can be prepared, for example, by double detergent dialysis as described in U.S. Pat. No. 5,252,348 and published EP patent application 0 555 333 B1. These viral envelopes have a cholesterol:phospholipid ratio of about 0.8 to about 1.2, preferably 1.0, similar to natural viral envelopes. The particles also have a homogenous size structure similar to that of natural viral particles and a physically stable unilamellar membrane structure.

In another method, SCNCs conjugated to specific biomolecules or unconjugated SCNCs can be incorporated into cells by forming pores in the cells. The pores can be formed by, for example, electroporation, osmotic shock, or by the use of a porogen. Electroporation is a common method for introducing foreign material, such as DNA, into cells (see Hui, 1995, *Methods in Molecular Biology*, Chapter 2, 48:29-40). The electroporation method of the invention consists of delivering high voltage pulses to cells thereby making pores in the cell membrane to facilitate the transport of SCNCs into cells. The electroporation process consists of two major steps: reversible breakdown of the cell membranes, and recovery of permeablized cells. Thus, the electrical and incubation parameters are optimized to facilitate the transfer of SCNCs across the membrane. In general, cells in suspension (from 1 to $10^{10}$ cells) can be placed in an electroporation cuvette with an appropriately sized SCNC (10 Å to 150 Å) at various concentrations (approximately 1 fmol to approximately 10 mM). The cuvette is then connected to an appropriate power supply and the cells/SCNCs are subjected to a high voltage pulse of defined magnitude and length. The voltage, capacitance and resistance can be varied appropriately depending on the cells or efficiency of the protocol. For example the voltage can be varied between about 1 V to about 100 kV, preferably 1 to 5 kV), the capacitance can be varied between about 0.1 Ff to about 100 f, preferably between about 1 Ff to about 50 Ff, and the resistance can be varied from about 0.1 S to about infinity. Cells should then be allowed to recover in the appropriate medium and detection of successfully transfected cells assessed using the appropriate detection systems for the SCNC.

Alternatively, the porogen can be digitonin, saporin, or a member of the complement cascade. Cells may be permeabilized with digitonin as described in Hagstrom et al. (1997) *J. Cell. Sci.* 110:2323-31, and in Sterne-Marr et al. (1992) *Meth. Enzymol.* 219:97-111, to allow the SCNC to be incorporated into the cell.

Figure 2:
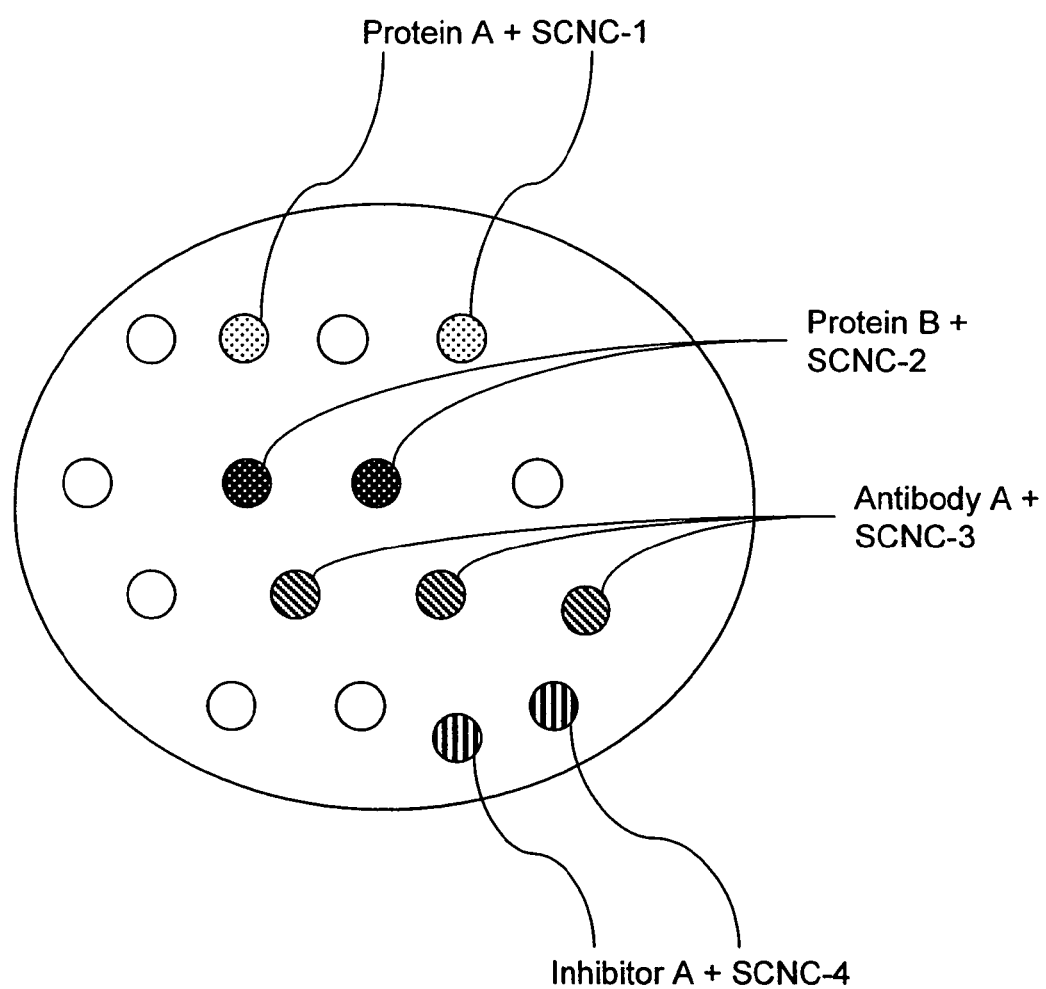
FIG. 2 is a pictorial representation illustrating the use SCNCs as a marker for identifying microinjected cells in which SCNCs are microinjected either alone or together with other molecules of interest to allow color-coded identification of a particular microinjected cell.
Figure 3:
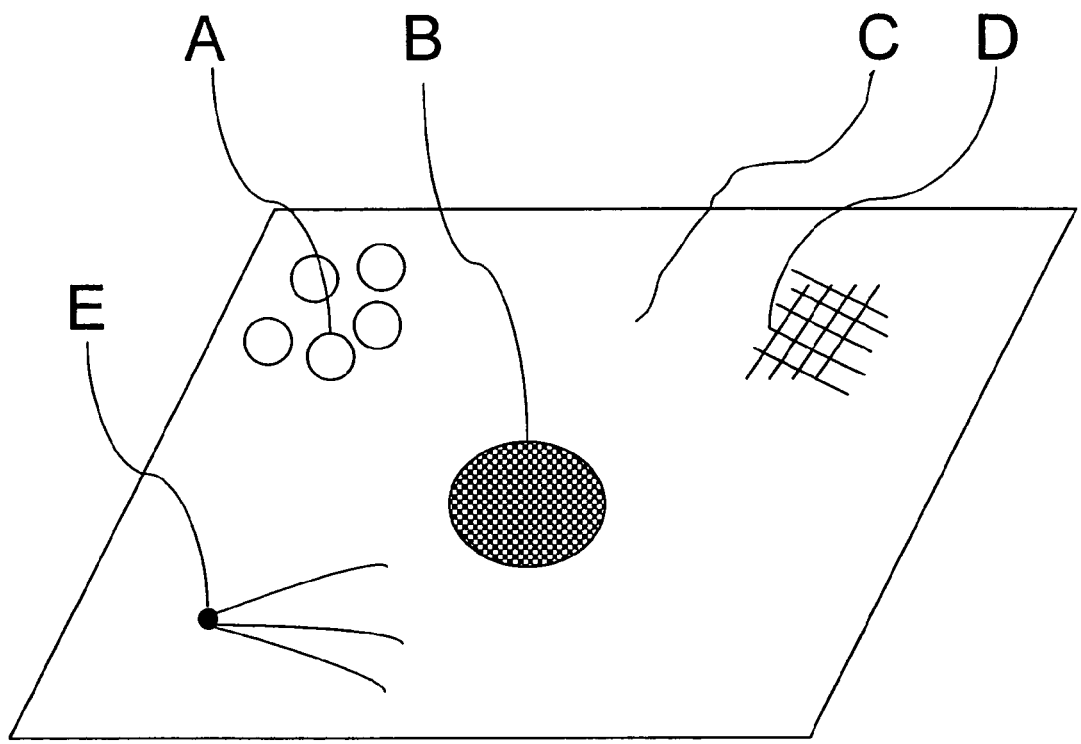
FIG. 3 is a pictorial representation illustrating the use of SCNCs as markers in multicolor immunofluorescent staining in which (A) represents a co-injected protein detected by indirect fluorescence with antibody conjugated to Fluo-4 or SCNC-5, (B) represents a nucleus stained with Fluo-3 or SCNC-4, (C) represents the cell marked with SCNC-1, (D) represents actin cytoskeleton stained with Fluo-1 or SCNC-2 conjugated to phalloidin, and (E) represents microtubules stained with Fluo-2 or SCNC-3 conjugated to tubulin.

There are many other ways in which SCNC can be introduced into cells, e.g., microinjection, passive pinocytosis or uptake via coating with viral fusogenic proteins. SCNCs can be used as flexible markers for identifying microinjected cells. To this end, SCNCs are microinjected either alone (as control) or together with other molecules of interest to allow color-coded identification of a particular microinjected cell. The method of microinjection uses a syringe needle, usually a heat-drawn sharp-ended glass tube, to puncture the cell membrane to deliver a solution containing SCNCs. SCNCs are suspended in an appropriate microinjected buffer at the required concentration (1 fm to 10 mM). The needle is aimed and actuated by using a micro-manipulator and viewed under a microscope. Once the cell is punctured, a controlled quantity of SCNCs is injected by applying a controlled pressure to the syringe plunger. After microinjection, the cells are left to recover. The size and composition of the SCNC (10 Å to 150 Å) determines the emission wavelength. This type of marker can be used, for example, to differentially mark cells injected with a particular molecule within a population of cells injected with multiple molecule (FIG. 2). Because all SCNCs can be excited at a common wavelength of light, or a wavelength may be selected to excite all species that have been used to encode the population of cells, all injected cells can be visualized concurrently and the effects of the co-injected molecule observed. In addition, the use of SCNCs as markers allows a flexible third, fourth, fifth, and greater, color to be used in multicolor immunofluorescent staining experiments (FIG. 3).

Transport of SCNCs Across Biological Membranes Using Cationic Polymers

One method for transporting SCNCs and other semiconductor nanoparticles across biological membranes, including across cell membranes and intracellular organelle membranes, such as the mitochondrial membrane, nuclear membranes, and the like, employs the use of peptides and cationic polymers that encourage entry of SCNCs into the cell.

One such peptide is an HIV-Tat peptide that facilitates viral passage into cells. The Tat peptide has been used to introduce magnetic nanoparticles into mammalian cells. Tat peptides for use herein can include peptides from the protein transduction domain of Tat. One particular Tat peptide for use herein is a fragment of the tat protein containing the tat basic region (residues 49-57 having the sequence RKKRRQRRR (SEQ ID NO: 1). SCNCs can be coated with Tat peptide sequences alone or along with other peptides, oligonucleotide or other affinity molecule to facilitate SCNC uptake by the cells and delivered to their appropriate binding partner or cellular compartment. Attachment can be achieved via any standard bioconjugation process well known in the art. SCNCs of any size and composition can be coated with both a peptide that recognizes a specific binding motif on an intracellular protein and also with a peptide that corresponds to the HIV-Tat sequence. Incubation of such modified SCNCs with a mammalian cell allows the SCNCs to enter the cell, probably via adsorptive endocytosis. Once inside the cell, the modified SCNCs can interact with and bind to the protein of oligonucleotide that contains the region recognized by the other peptide or oligonucleotide, respectively, on the surface of the SCNC. This will provide information as to the localization, trafficking and abundance of that protein. If a second color of SCNC that carries an affinity molecule for a second intracellular protein or oligonucleotide is introduced via a similar method then the relative positions of the two molecules can be determined (see FIG. 1).

Other viral-based peptides for enhancing transport of molecules into the cytoplasm and nucleus of cells are described in e.g., Tkachendo et al., *J. Am. Chem. Soc.* (2003) 125:4700-4701, and include peptides derived from the SV40 large T NLS, such as the peptide with the sequence CGGGP-KKKRKVG (SEQ ID NO:2), peptides from the adenoviral NLS, such as the peptide with the sequence CGGFSTSL-RARKA (SEQ ID NO:3), peptides from the adenoviral RME, such as a peptide with the sequence CKKKKKKSEDEY-PYVPN (SEQ ID NO:4) and peptides from the adenoviral fiber protein such as a peptide having the sequence CKKKKKKKSEDEYPYVPNFSTSLRARKA (SEQ ID NO:5).

Similarly, other cationic polymers, i.e., polymers with a series of positively charged monomers, can be used to facilitate transport of SCNCs over biological membranes. Typically, although not exclusively, the positively charged groups are primary, secondary or tertiary amines which ionize at or around neutral pH. Such amine groups can be present as amino groups in side chains as in poly(amino acids); amino groups included in a polymer backbone as in poly(amines); or amino substituents added to an uncharged polymer, such as result in dextran substituted with diethylaminoethyl groups. Polymers containing other positively charged groups, such as quaternary amines, the sulfur group in S-methyl methionine, etc., would also be suitable.

Specific poly(amino acids) which are suitable include, but are not limited to, poly-L-lysine, poly-L-ornithine, poly-L-arginine, poly-L-homoarginine, poly-L-diaminobutyric acid, poly-L-histidine, the D-optical isomers thereof and copolymers thereof. Copolymers may include non-cationic amino acid residues. Cationic poly(amino acids) are preferred. Additionally, it may be desirable to employ cationic polymers which are digested by proteolytic enzymes present in mammalian cells, such as, for example, poly-L-lysine and poly-L-arginine.

Other cationic polymers suitable for use with the present methods include polymers with neutral or anionic backbones to which cationic groups have been bonded, such as substituted polysaccharides (e.g., diethylaminoethyl dextran), substituted cellulose, substituted copolymers of ethylene and maleic anhydride, substituted lactic or glycolic acid polymers, and the like. Polyamines, such as for instance, poly (vinyl amine), or other cationic synthetic polymers, will also find use herein.

Additionally, other positively charged, naturally occurring macromolecules will also serve as suitable cationic polymers. Specific examples include protamines and histones, such as those found to increase cellular uptake of albumin by their simple presence. See, Ryser et al., Science (1965) 150:501-503.

Generally, the multiple positive charges present in the cationic polymer will give the molecule a net positive charge. In other cases, however, the multiple charges may form an adequate sequence in the primary structure, or an adequate spacial arrangement in the tertiary structure, or both, to cause enhanced transport, even though the molecule does not itself have an overall net positive charge. For example, a molecule containing a limited number of positive charges at various intervals in its primary structure may fold in a manner such that a cluster of positive charges will be positioned in the same spatial area of its tertiary structure. Alternatively, a copolymer of poly(amino acid) with a neutral or negative net charge may contain a functionally important cluster of positive charges. Therefore, as used herein, the term "cationic polymer" refers not only to a polymer which has an overall positive net charge, but also includes polymers that contain sequential portions or spatial arrangements of positive charges sufficient to confer on them the transport properties of cationic polymers having a net positive charge.

Preferably, the cationic polymer will include from about 5 to about 50 subunits, more preferably from about 5 to about 25 subunits, or any number within these ranges, such as 6, 7, 8, 9, 10 . . . 15 . . . 20 . . . 25, and so forth. In some cases, at least half of the subunits will include a guanidino or amidino sidechain moiety. Such polymers are described in e.g., U.S. Pat. No. 6,495,663, the disclosure of which is incorporated herein by reference in its entirety. Particularly preferred, are polymers containing about 4 to 25 contiguous Arg or Lys residues, preferably from 7-15 such residues. However, the residues need not be contiguous and it may sometimes be desirable to include, e.g., repeating units of two or three Arg or Lys residues, or the like, separated by other amino acids. See, e.g., U.S. Patent Application Publication No. 2003/0032593, incorporated herein by reference in its entirety.

The polymers are constructed by any method known in the art. For example, peptides can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barmy and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx);

2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

N-methyl and hydroxy-amino acids can be substituted for conventional amino acids in solid phase peptide synthesis. However, production of polymers with reduced peptide bonds requires synthesis of the dimer of amino acids containing the reduced peptide bond. Such dimers are incorporated into polymers using standard solid phase synthesis procedures. Other synthesis procedures are well known and can be found, for example, in Fletcher et al., *Chem. Rev.* (1998) 98:763-795, Simon et al., *Proc. Natl. Acad. Sci.* (1992) 89:9367-9371, and references cited therein.

Alternatively, the peptides can be produced by recombinant techniques, e.g., by synthesizing DNA encoding the desired peptide, along with an ATG initiation codon. The nucleotide sequence can be designed with the appropriate codons for the particular amino acid sequence desired. In general, one selects preferred codons for the intended host in which the sequence is expressed. The complete sequence is generally assembled from overlapping oligonucleotides prepared by standard methods and assembled into a complete coding sequence. See, e.g., Edge *Nature* (1981) 292:756; Nambair et al. *Science* (1984) 223:1299; Jay et al. *J. Biol. Chem.* (1984) 259:6311. Automated synthetic techniques such as phosphoramide solid-phase synthesis, can be used to generate the nucleotide sequence. See, e.g., Beaucage, S. L. et al. *Tet. Lett.* (1981) 22:1859-1862; Matteucci, M. D. et al. *J. Am. Chem. Soc.* (1981) 103:3185-3191. Next the DNA is cloned into an appropriate expression vector, either procaryotic or eucaryotic, using conventional methods.

Transport polymers of the invention can be associated with SCNCs by simply mixing the particular polymer with the nanoparticles thereby forming a non-covalent association. See, e.g., Example 1 herein. Alternatively, the transport polymers can be attached covalently to SCNCs by a number of chemical methods, methods known in the art (see, for example, Wong, S. S., Ed., *Chemistry of Protein Conjugation and Cross-Linking*, (1991) CRC Press, Inc., Boca Raton, Fla., either directly (e.g., with a carbodiimide) or via a linking moiety. In particular, carbamate, ester, thioether, disulfide, and hydrazone linkages are generally easy to form and suitable for most applications. Ester and disulfide linkages are preferred if the linkage is to be readily degraded in the cytosol, after transport of the substance across the cell membrane.

Various functional groups (hydroxyl, amino, halogen, etc.) can be used to attach the SCNC to the transport polymer.

Moreover, the SCNC can be associated with the cationic polymer using first and second members of a binding pair. In a preferred embodiment, steptavidin, avidin or neutravidin is coupled to the SCNC and biotin is coupled to the cationic polymer. Alternatively, biotin is coupled to the SCNC and steptavidin, avidin or neutravidin is coupled to the cationic polymer. Methods for biotinylating peptides are well known in the art, and various commercial sources, such as Pierce Chemical Co., Rockford Ill., sell kits for doing so Cationic polymers are generally produced with an amino terminal protecting group, such as FMOC. The FMOC may be cleaved from the N-terminus of the completed resin-bound polypeptide so that the SCNC can be linked to the free N-terminal amine. In such cases, the SCNC is typically activated by methods well known in the art to produce an active ester or active carbonate moiety effective to form an amide or carbamate linkage, respectively, with the polymer amino group. Of course, other linking chemistries can also be used.

To help minimize side-reactions, guanidino and amidino moieties can be blocked using conventional protecting groups, such as carbobenzyloxy groups (CBZ), di-t-BOC, PMC, Pbf, N-NO$_2$, and the like.

Coupling reactions are performed by known coupling methods in any of an array of solvents, such as N,N-dimethyl formamide (DMF), N-methylpyrrolidinone, dichloromethane, water, and the like. Exemplary coupling reagents include O-benzotriazolyloxy tetramethyluronium hexafluorophosphate (HATU), dicyclohexyl carbodiimide, bromo-tris (pyrrolidino) phosphonium bromide (PyBroP), etc. Other reagents can be included, such as N,N-dimethylamino pyridine (DMAP), 4-pyrrolidino pyridine, N-hydroxy succinimide, N-hydroxy benzotriazole, and the like.

The linker may be a readily cleavable linker, meaning that it is susceptible to enzymatic or solvent-mediated cleavage in vivo. For this purpose, linkers containing carboxylic acid esters and disulfide bonds are preferred, where the former groups are hydrolyzed enzymatically or chemically, and the latter are severed by disulfide exchange, e.g., in the presence of glutathione.

In one embodiment, the cleavable linker contains a first cleavable group that is distal to the SCNC, and a second cleavable group that is proximal to the SCNC, such that cleavage of the first cleavable group yields a linker-SCNC conjugate containing a nucleophilic moiety capable of reacting intramolecularly to cleave the second cleavable group, thereby releasing the SCNC from the linker and polymer.

Methods for conjugating cationic polymers to molecules to be transported are known in the art and described in e.g., U.S. Pat. Nos. 4,847,240 and 6,495,663; and U.S. Patent Application Publication No. 2003/0032593, the disclosures of which are incorporated herein by reference in their entireties.

The Coding Scheme

The cells are encoded to allow rapid analysis of cell, identity, as well as allowing multiplexing. The coding scheme preferably employs one or more different SCNCs, although a variety of additional agents, including chromophores, fluorophores and dyes, and combinations thereof can be used alternatively or in combination with SCNCs. For organic dyes, different dyes that have distinguishable fluorescence characteristics can be used. Different SCNC populations having the same peak emission wavelength but different peak widths can be used to create different codes if sufficient spectral data can be gathered to allow the populations to be distinguished. Such different populations can also be mixed to create intermediate linewidths and hence more unique codes. In addition, the coding scheme can be based on differences in excitation wavelength, emission wavelength, emission intensity, FWHM (full width at half maximum peak height), fluorescence lifetime, or combinations thereof.

The number of SCNCs used to encode a single cell locale can be selected based on the particular application. Single SCNCs can be detected (see, e.g., U.S. Application Ser. No. 09/784,866, filed Feb. 15, 2001 and entitled "Single Target Counting Assays Using Semiconductor Nanocrystals; Empedocles et al. inventors); however, a plurality of SCNCs from a given population is preferably incorporated in a single cell to provide a stronger, more continuous emission signal from each cell and thus allow shorter analysis time.

Different SCNC populations can be prepared with peak wavelengths separated by approximately 1 nm, and the peak wavelength of an individual SCNC can be readily determined with 1 nm accuracy. In the case of a single-peak spectral code, each wavelength is a different code. For example, CdSe SCNCs have a range of emission wavelengths of approximately 490-640 nm and thus can be used to generate about 150 single-peak codes at 1 nm resolution.

A spectral coding system that uses only highly separated spectral peaks having minimal spectral overlap and does not require stringent intensity regulation within the peaks allows for approximately 100,000 to 10,000,000 or more unique codes in different schemes.

A binary coding scheme combining a first SCNC population having an emission wavelength within a 490-565 nm channel and a second SCNC population within a 575-650 nm channel produces 3000 valid codes using 1-nm resolved SCNC populations if a minimum peak separation of 75 nm is used. The system can be expanded to include many peaks, the only requirement being that the minimum separation between peak wavelengths in valid codes is sufficient to allow their resolution by the detection methods used in that application.

A binary code using a spectral bandwidth of 300 nm, a coding-peak resolution, i.e., the minimum step size for a peak within a single channel, of 4 nm, a minimum interpeak spacing of 50 nm, and a maximum of 6 peaks in each code results in approximately 200,000 different codes. This assumes a purely binary code, in which the peak within each channel is either "on" or "off." By adding a second "on" intensity, i.e., wherein intensity is 0, 1 or 2, the number of potential codes increases to approximately 5 million. If the coding-peak resolution is reduced to 1 nm, the number of codes increases to approximately $1 \times 10^{10}$.

Valid codes within a given coding scheme can be identified using an algorithm. Potential codes are represented as a binary code, with the number of digits in the code corresponding to the total number of different SCNC populations having different peak wavelengths used for the coding scheme. For example, a 16-bit code could represent 16 different SCNC populations having peak emission wavelengths from 500 nm through 575 nm, at 5 nm spacing. A binary code 1000 0000 0000 0001 in this scheme represents the presence of the 500 nm and 575 nm peaks. Each of these 16-bit numbers can be evaluated for validity, depending on the spacing that is required between adjacent peaks; for example, 0010 0100 0000 0000 is a valid code if peaks spaced by 15 nm or greater can be resolved, but is not valid if the minimum spacing between adjacent peaks must be 20 nm. Using a 16-bit code with 500 to 575 nm range and 5 nm spacing between peaks, the different number of possible valid codes for different minimum spectral spacings between adjacent peaks is shown in Table 2.

TABLE 2

The number of unique codes with a binary 16-bit system.

| | Spectral Separation | | | | | |
|---|---|---|---|---|---|---|
| | 5 nm | 10 nm | 15 nm | 20 nm | 25 nm | 30 nm |
| Number of unique codes | 65535 | 2583 | 594 | 249 | 139 | 91 |

If different distinguishable intensities are used, then the number of valid codes dramatically increases. For example, using the 16-bit code above, with 15 nm minimum spacing between adjacent peaks in a code, 7,372 different valid codes are possible if two intensities, i.e., a ternary system, are used for each peak, and 38,154 different valid codes are possible for a quaternary system, i.e., wherein three "on" intensities can be distinguished.

Codes utilizing intensities require either precise matching of excitation sources or incorporation of an internal intensity standard into the cells due to the variation in extinction coefficient exhibited by individual SCNCs when excited by different wavelengths.

It is preferred that the light source used for the encoding procedure be as similar as possible (preferably of the same wavelength and intensity) to the light source that will be used for decoding. The light source may be related in a quantitative manner, so that the emission spectrum of the final material may be deduced from the spectrum of the staining solution.

Codes can optionally be created by using substantially non-overlapping colors of SCNCs, and then combining the SCNCs in unique ratios, or according to absolute levels. Alternative codes might be created by relying on overlapping signal deconvolution.

The code creation methods optionally use a computer program to combine or mix together, in silico (that is, using computer modeling), emission signals from SCNCs.

These individual marker signal spectra can be real spectra from SCNCs that have already been manufactured, or simulated spectra for SCNC batches that can be manufactured. Candidate code spectra are then compared against one another, with acceptable codes added to the library in order to create an optimal set of codes that are sufficiently different from each other to allow robust code assignment given constraints such as code-number requirements and instrument resolution. A further method uses stored patterns of known code spectra against which to evaluate an unknown spectrum, in order to assign a code to the unknown spectrum, or to declare it as "no match." To do this, several steps are performed, some optional: (1) creation of a code; (2) creation of a template for the code; (3) comparison of a sample spectrum against all possible templates; and (4) assignment of "match" or "no match" to the sample based upon its degree of similarity to one of the templates and/or dissimilarity to the remainder.

Coded objects can be created by attaching one or more SCNC batches to an object or to many objects simultaneously. One criterion for creating useful codes is that, when a code is analyzed, it can be uniquely identified within the statistical confines of the experiment or actual code reading equipment. Generally, all codes to be used in a given application should be spectrally resolvable, i.e., sufficiently spectrally dissimilar within manufacturing tolerances and/or reading error, such that the rate of incorrect decoding is very low. The acceptable error rate depends on the application. Codes may be created randomly or systematically. Using the random approach, mixtures of SCNCs are created and then used as codes. Using the systematic approach, SCNC batches are chosen, and mixed together in the appropriate ratios to generate the codes. In both approaches, the composite emission spectrum of each new code is compared to the emission spectrum of all other codes that will be used in the application. This can be done prior to the actual physical creation of the code, by using predicted spectra, or can be done by reading the spectrum of the new code prior to, or after, attaching the code to the object(s). If the code is non-overlapping, i.e., will not be misclassified when noise, aging, reader differences, or other factors are taken into account, then the code is valid to be used. The emission spectrum of the new code is stored digitally so that putative new codes, and unknown codes during code reading, can be compared against it. Preferably, reading accuracy will be incorporated into the comparison of prior codes with new codes, the reading accuracy generally being determined based on known properties of one or more of the excitation energy source, the sensor, and the data manipulation performed by the processor.

When many items are being coded with the same code, e.g., when attaching SCNCs to cells, microspheres or beads in a batch mode, it is useful to analyze more than one of those items and store an average, or representative, spectrum for the code. Once this has been done, the actual spectrum for each sample item can be compared with the average spectrum to ensure that they are correctly identified. They may also be compared against the spectra of other codes to ensure that they are not mis-identified. Furthermore, statistical information regarding, for example, reproducibility and confidence levels can be gleaned at this stage.

The stored emission spectrum may herein be called the code's "template" and can have been generated experimentally by analyzing coded object(s) or SCNC mixtures, or can be generated in silico by adding together emission spectra from the SCNCs that make up the code, along with any required correction factors.

Template emission spectra may be generated by using the instrument (or a similar instrument, or a computer model of the instrument) that will be used for reading the code, optionally correcting for any instrument-to-instrument variation. For example, for SCNC-encoded cell assays it is desirable to analyze wells that contain a single or a few different known coded cells that have been processed through assay conditions. The template emission spectra may be generated for each encoded cell reader instrument so that during analysis, the templates for a given reader or assay are used.

Many different systematic methods for creating codes can be envisioned. For example, two colors of SCNCs may be used and the ratio of color 1:color-2 varied to create different codes. Using additional colors, the different ratios can be varied to create codes that are more complex.

SCNC batches that have the same color, i.e., the same peak wavelength, but have different peak widths, can be used to create two different codes if sufficient spectral data is gathered to allow these to be defined as being significantly different. These batches can also be mixed to create intermediate linewidths and hence more unique codes.

A computer-based method that uses all physically available SCNC spectra, or that uses electronically generated spectra of all manufacturable SCNC batches, can be used. In this case, the computer is programmed to combine systematically or randomly different amounts of these SCNC spectra, in silico, along with any correction factors desired due to energy or electron transfer, emission intensity variations, or wavelength changes that may occur. The electronically created spectra are compared against current codes and any that are sufficiently distinguishable are candidates for manufacturing into real physical codes. This type of approach can also be used to create code sets, i.e., manufacturable emission spectra that are chosen to be maximally different from one another according to predetermined comparison criteria such as the residual value from a least squares fitting, or other methods known in the art.

Data on the overall emission spectrum of a code can be gathered by exciting the SCNCs with an appropriate source, e.g., laser, lamp, light-emitting diode, or the like, and reading the emitted light with a device that provides spectral information for the object, e.g., grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, colored glass filters, or electronically tunable filters are appropriate). More than one imager may be used to gather data simultaneously through dedicated filters, or the filter may be changed in front of a single imager. Once this data has been gathered, it can be processed to generate spectral information about objects in the image, or for each pixel, or group of pixels in the image, via straightforward image processing techniques.

The emission spectrum from the sample object is compared against all the known templates. This can be done using many techniques known in the art such as least squares fitting, Fourier analysis, Kolmogorov-Smirnov Test, Pearson Rank Correlation test, or the like (see *Numerical Recipes* in C, Press et al., Cambridge University Press, 1996). In each case, a measure of the goodness of fit of the unknown to each template is generated, (e.g., a residual value for a least squares approach, or other fit measure dependent on the fitting algorithm used such as one of the "robust" or absolute magnitude methods described by Press et al., supra). If this goodness of fit falls within the pre-determined range for only one of the codes then this is the identity of the unknown code, otherwise the unknown is classified as "no match," or as matching too many templates.

It might be desirable to make the matching process insensitive to absolute intensity variations. This can be done by including a linear or non-linear intensity normalization factor during the matching process, which is varied to generate the lowest residual value or other match parameter for each comparison. The normalization factor can be allowed to vary without limits or can be constrained to be within a given range to limit the amount of correction for intensity variations.

The spectral data can also be normalized spectrally, i.e., shifting the data spectrally in a linear or nonlinear manner, to correct for variations in the wavelength that may occur due to the instrument or due to temperature changes, degradation, or other effects that cause the SCNCs to emit at different wavelengths. Again, the spectral shift factor may be constrained to be within a given range.

When the emission spectrum also contains signal from a reporter or reference SCNC, e.g., in the case of encoded cell assays, this may be quantitated at the same time, and may also be normalized according to the factors described above. Any spectral overlap from the code into the assay signal may also be corrected for in this way.

Spectral data will often be collected from more windows and/or allowed discrete wavelengths than there are colors of SCNCs present. This allows SCNCs of only slightly differing wavelengths to be used to create the codes. Additional spectral data also makes the classification process more robust than simple one-color, one-data point approaches. An advantage of the pattern matching approach for analysis is that, independent of the method of code creation, any sufficiently different spectra can be used as unique codes. Since unique fingerprints can be obtained for each code based on individual raw spectra, concrete statistical estimates can be used in determinations such as goodness of fit, confidence intervals, and determination of uniqueness. In addition, this method allows for empirical determination of codes following chemical processing as blanks, removing much of the ambiguity associated with pre-formatted idealized code sets.

Spectrally Encoded Microspheres.

Microspheres for use in the invention disclosed herein can be spectrally encoded through incorporation of SCNCs See, e.g., U.S. Pat. No. 6,207,392 to Weiss et al., issued Mar. 27, 2001, International Pat. Publ. No. WO 00/17103 (inventors Bawendi et al.), published Mar. 30, 2000, and Han et al. (2001) *Nature Biotech.* 19:632-635.

Preferably, microspheres or beads used to encode cells are approximately less than about 1 micrometer, preferably 0.01 to about 0.5 micrometer, more preferably 0.01 to about 0.1 micrometer, and can be manipulated using normal solution techniques when suspended in a solution. Each individual cell can be encoded with a single microsphere having a unique code. Alternatively, each individual cell can be encoded with more than one microsphere as needed to provide a uniquely encoded cell. The beads can be prepared to contain a population of SCNCs having a single peak emission wavelength or the beads can be prepared to contain more than a single population of SCNCs, each population having a peak emission wavelength, or other fluorescence characteristic (for example excitation wavelength, emission wavelength, emission intensity, FWHM (full width at half maximum peak height), or fluorescence lifetime) that is distinguishable from that of the other populations, such that each bead has a unique spectral signature.

Polymeric microspheres or beads can be prepared from a variety of different polymers, including but not limited to polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers and epoxies. The materials have a variety of different properties with regard to swelling and porosity, which are well understood in the art. The terms "bead," "sphere," "microbead" and "microsphere" are used interchangeably herein.

The desired fluorescence characteristics of the microspheres may be obtained by mixing SCNCs of different sizes and/or compositions in a fixed amount and ratio to obtain the desired spectrum, which can be determined prior to association with the microspheres. Subsequent treatment of the microspheres (through, for example, covalent attachment, co-polymerization, or passive absorption or adsorption) with the staining solution results in a material having the designed fluorescence characteristics.

A number of SCNC solutions can be prepared, each having a distindt distribution of sizes and compositions, to achieve the desired fluorescence characteristics. These solutions may be mixed in fixed proportions to arrive at a spectrum having the predetermined ratios and intensities of emission from the distinct SCNCs suspended in that solution. Upon exposure of this solution to a light source, the emission spectrum can be measured by techniques that are well established in the art. If the spectrum is not the desired spectrum, then more of the SCNC solution needed to achieve the desired spectrum can be added and the solution "titrated" to have the correct emission spectrum. These solutions may be colloidal solutions of SCNCs dispersed in a solvent, or they may be pre-polymeric colloidal solutions, which can be polymerized to form a matrix with SCNCs contained within.

The composition of the staining solution can be adjusted to have the desired fluorescence characteristics, preferably under the exact excitation source that will be used for the decoding. A multichannel auto-pipettor connected to a feedback circuit can be used to prepare an SCNC solution having the desired spectral characteristics, as described above. If the several channels of the titrator/pipettor are charged with several unique solutions of SCNCs, each having a unique excitation and emission spectrum, then these can be combined stepwise through addition of stock solutions.

Once the staining solution has been prepared, it can be used to incorporate a unique spectral code into a given bead population. If the method of incorporation of the SCNCs into the beads is absorption or adsorption, then the solvent that is used for the staining solution should be one that is suitable for swelling the microspheres, and can be selected based on the microsphere composition. Typical solvents for swelling microspheres include those in which the microsphere material is more soluble, for example dichloromethane, chloroform, dimethylformamide, tetrahydrofuran and the like. These can be mixed with a solvent in which the microsphere material is less soluble, for example methanol or ethanol, to control the degree and rate of incorporation of the staining solution into the material.

The microspheres swell when added to the staining solution and incorporate a plurality of SCNCs in the relative proportions that are present in the staining solution. After removal of the staining solution from the material, a non-swelling solvent is added, the material shrinks, or unswells, thereby trapping the SCNCs in the material. Alternatively, SCNCs can be trapped by evaporation of the swelling solvent from the material. After rinsing with a nonswelling solvent in which the SCNCs can be suspended, the SCNCs are trapped in the material, and can be retained by further use of a non-swelling solvent. Typical nonswelling solvents include hexane and toluene. The thus-encoded beads can be separated and exposed to a variety of solvents without a change in the emission spectrum under the light source. When the material used is a polymer bead, the material can be separated from the rinsing solvent by any suitable technique, for example, centrifugation, evaporation, fluidized bed drying, etc., or combined procedures, and can be redispersed into aqueous solvents and buffers through the use of detergents in the suspending buffer.

The staining procedure can also be carried out in sequential steps. A first staining solution can be used to stain the beads with one population of SCNCs. The beads can then be separated from the first staining solution and added to a second staining solution to stain the beads with a second population of SCNCs. These steps can be repeated until the desired spectral properties are obtained from the material when excited by a light source.

The SCNCs can be attached to the beads by covalent attachment as well as by entrapment in swelled beads, or can be coupled to one member of a binding pair the other member of which is attached to the beads. For instance, SCNCs are prepared by a number of techniques that result in reactive groups on the surface of the SCNC. See, e.g., Bruchez et al. (1998) *Science* 281:2013-2016, Chan et al. (1998) *Science* 281:2016-2018, Colvin et al. (1992) *J. Am. Chem. Soc.* 114: 5221-5230, Katari et al. (1994) *J. Phys. Chem.* 98:4109-4117, Steigerwald et al. (1987) *J. Am. Chem. Soc.* 110:3046. The reactive groups present on the surface of the SCNCs can be coupled to reactive groups present on a surface of the material. For example, SCNCs which have carboxylate groups present on their surface can be coupled to beads with amine groups using a carbodiimide activation step.

Any cross-linking method that links a SCNC to a bead and does not adversely affect the properties of the SCNC or the bead can be used. In a cross-linking approach, the relative amounts of the different SCNCs can be used to control the relative intensities, while the absolute intensities can be controlled by adjusting the reaction time to control the number of reacted sites in total. After the beads are crosslinked to the SCNCs, the beads are optionally rinsed to wash away unreacted SCNCs.

A sufficient amount of fluorophore must be used to encode the beads so that the intensity of the emission from the fluorophores can be detected by the detection system used and the different intensity levels must be distinguishable, where intensity is used in the coding scheme but the fluorescence emission from the SCNCs or other fluorophores used to encode the beads must not be so intense to as to saturate the detector used in the decoding scheme.

The beads can be encoded to allow rapid analysis thereof, and thus of the cell encoded therewith, identity, as well as allowing multiplexing. The coding scheme preferably employs one or more different SCNCs, although a variety of additional agents, including chromophores, fluorophores and dyes, and combinations thereof can be used alternatively or in combination with SCNCs. For organic dyes, different dyes that have distinguishable fluorescence characteristics can be used. Different SCNC populations having the same peak emission wavelength but different peak widths can be used to create different codes if sufficient spectral data can be gathered to allow the populations to be distinguished. Such different populations can also be mixed to create intermediate linewidths and hence more unique codes.

The number of SCNCs used to encode a single bead or substrate locale can be selected based on the particular application. Single SCNCs can be detected; however, a plurality of SCNCs from a given population is preferably incorporated in a single bead to provide a stronger, more continuous emission signal from each bead and thus allow shorter analysis time.

The beads can be encoded using the coding scheme described supra.

The Excitation Source

By exposing the encoded cells prepared and described as above to light of an excitation source, the SCNCs disposed in or on the cell will be excited to emit light. This excitation source is of an energy capable of exciting at least one population of SCNCs used in the experiment to emit light and preferably chosen to be of higher energy than the shortest emission wavelength of the SCNCs used. Further, the excitation source can be chosen such that it excites a minimum number of SCNCs in the sample to produce detectable light. Preferably the excitation source will excite a sufficient number of different populations of SCNCs to allow unique identification of all the encoded materials used in the experiment. For example, using two different populations of cells having different ratios of red to blue SCNCs, it would not be sufficient to only excite the red emitting SCNCs, e.g., by using green or yellow light, of the sample in order to decode the cells. It would be necessary to use a light source comprising at least one wavelength that is capable of exciting the blue emitting and the red emitting SCNCs simultaneously, e.g., violet or ultraviolet. There may be one or more light sources used to excite the different populations of SCNCs simultaneously, or sequentially, but a given light source will only excite subpopulations of SCNCs that emit at lower energy than the light source, due to the absorbance spectra of the SCNCs.

In addition, if a lamp source is used, degradation of the lamp can result in changes in the excitation source, thereby compromising the codes.

Detection of Emission

An example of an imaging system for automated detection for use with the present methods comprises an excitation source, a monochromator (or any device capable of spectrally resolving the image, or a set of narrow band filters) and a detector array. The excitation source can comprise blue or UV wavelengths shorter than the emission wavelength(s) to be detected. This may be: a broadband UV light source, such as a deuterium lamp with a filter in front; the output of a white light source such as a xenon lamp or a deuterium lamp after passing through a monochromator to extract out the desired wavelengths; or any of a number of continuous wave (cw) gas lasers, including but not limited to any of the Argon Ion laser lines (457, 488, 514, etc. nm) or a HeCd laser; solid state diode lasers in the blue such as GaN and GaAs (doubled) based lasers or the doubled or tripled output of YAG or YLF based lasers; or any of the pulsed lasers with output in the blue.

The emitted light can be detected with a device that provides spectral information for the substrate, e.g., grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, or electronically tunable filters are appropriate). More than one imager may be used to gather data simultaneously through dedicated filters, or the filter may be changed in front of a single imager. Imaging based systems, like the Biometric Imaging system, scan a surface to find fluorescent signals.

A scanning system can be used in which the sample to be analyzed is scanned with respect to a microscope objective. The luminescence is put through a single monochromator or a grating or prism to spectrally resolve the colors. The detector is a diode array that then records the colors that are emitted at a particular spatial position. The software then recreates the scanned image.

In the embodiment where cell or the population of cells is encoded with light-scattering SERS or SERRS particle, the Raman signal is detected using an epifluorescence laser confocal microscope comprising a visible or infra red excitation laser, a dichroic beam-splitter, a microscope objective, an excitation cutoff filter, spectrometer and high efficiency detector such as a CCD camera. Alternatively, the detection system can use line illumination and collection by adding a cylindrical lens to the excitation pathway and using a 2D detector. Alternatively, the detection system can use area illumination and detection, and generate spectral data by using a tunable bandpass filter or a number of fixed bandpass filters placed in the detection pathway.

Decoding Multiple Fluorescence Emissions

When imaging samples labeled with multiple fluorophores, it is desirable to resolve spectrally the fluorescence from each discrete region within the sample. Such samples can arise, for example, from multiple types of SCNCs (and/or other fluorophores) being used to encode cells, from a single type of SCNC being used to encode cells but bound to a molecule labeled with a different fluorophore, or from multiple cells labeled with different types of fluorophores which overlap. Decoding the spectral code of an encoded substrate can take place prior to, simultaneously with, or subsequent to obtaining information from a functional assay performed on the cells.

Many techniques have been developed to solve this problem, including Fourier transform spectral imaging (Malik et al. (1996) *J. Microsc.* 182:133; Brenan et al. (1994) *Appl. Opt.* 33:7520) and Hadamard transform spectral imaging (Treado et al. (1989) *Anal. Chem.* 61:732 Å; Treado et al. (1990) *Appl. Spectrosc.* 44:1-4; Treado et al. (1990) *Appl. Spectrosc.* 44:1270; Hammaker et al. (1995) *J. Mol. Struct.* 348:135; Mei et al. (1996) *J. Anal. Chem.* 354:250; Flateley et al. (1993) *Appl. Spectrosc.* 47:1464), imaging through variable interference (Youvan (1994) *Nature* 369:79; Goldman et al. (1992) *Biotechnology* 10:1557), acousto-optical (Mortensen et al. (1996) *IEEE Trans. Inst. Meas.* 45:394; Turner et al. (1996) *Appl. Spectrosc.* 50:277) or liquid crystal filters (Morris et al. (1994) *Appl. Spectrosc.* 48:857) or simply scanning a slit or point across the sample surface (Colarusso et al. (1998) *Appl. Spectrosc.* 52:106 Å), all of which are capable of generating spectral and spatial information across a two-dimensional region of a sample.

One-dimensional spectral imaging can easily be achieved by projecting a fluorescent image onto the entrance slit of a linear spectrometer. In this configuration, spatial information is retained along the y-axis, while spectral information is dispersed along the x-axis (Empedocles et al. (1996) *Phys. Rev. Lett.* 77(18):3873). The entrance slit restricts the spatial position of the light entering the spectrometer, defining the calibration for each spectrum. The width of the entrance slit, in part, defines the spectral resolution of the system.

Two-dimensional images can be obtained by eliminating the entrance slit and allowing the discrete images from individual points to define the spatial position of the light entering the spectrometer. In this case, the spectral resolution of the system is defined, in part, by the size of the discrete images. Since the spatial position of the light from each point varies across the x-axis, however, the calibration for each spectrum will be different, resulting in an error in the absolute energy values. Splitting the original image and passing one half through a dispersive grating to create a separate image and spectra can eliminate this calibration error. With appropriate alignment, a correlation can be made between the spatial position and the absolute spectral energy.

To avoid ambiguity between images that fall along the same horizontal line, a second beam-splitter can be added, with a second dispersive element oriented at 90 degrees to the original. By dispersing the image along two orthogonal directions, it is possible to unambiguously distinguish the spectra from each discrete point within the image. The spectral dispersion can be performed using gratings, for example holographic transmission gratings or standard reflection gratings. For example, using holographic transmission gratings, the original image is split into 2 (or 3) images at ratios that provide more light to the spectrally dispersed images, which have several sources of light loss, than the direct image. This method can be used to spectrally image a sample containing discrete point signals, for example in high throughput screening of discrete spectral images such as single cells or ensembles of cells immobilized on a substrate, and for highly parallel reading of spectrally encoded cells. The images are then projected onto a detector and the signals are recombined to produce an image that contains information about the amount of light within each band-pass.

Alternatively, techniques for calibrating point spectra within a two-dimensional image are unnecessary if an internal wavelength reference (the "reference channel") is included within the spectrally encoded cell. The reference channel is preferably either the longest or shortest wavelength emitting fluorophore in the code. The known emission wavelength of the reference channel allows determination of the emission wavelengths of the fluorophores in the dispersed spectral code image. In addition to wavelength calibration, the reference channel can serve as an intensity calibration where coding schemes with multiple intensities at single emission wavelengths are used. Additionally, a fixed intensity of the reference channel can also be used as an internal calibration standard for the quantity of label bound to the surface of each bead.

In one system for reading spectrally encoded cells, a confocal excitation source is scanned across the surface of a sample. When the source passes over an encoded cell, the fluorescence spectrum is acquired. By raster-scanning the point-excitation source over the sample, all of the cells within a sample can be read sequentially.

Encoded Cells Immobilized on Chips

Qcell™ encoding technology may be used to study membrane receptor proteins. Membrane receptor proteins constitute an important target class for drug development, yet are difficult to purify and immobilize on protein chips. Native expression of membrane proteins in SCNC-encoded cells greatly facilitates the correct folding and identification of these proteins for use in a variety of proteomics and diagnostics applications. Encoded cells are randomly deposited on the chip surface, and there is no need to spatially arrange each receptor for encoding. This assay platform is compatible with a variety of detection technologies that measure binding of fluorescent-tagged ligands to proteins on a chip surface.

Encoded cells may be utilized in conjunction with a substrate, and may be grown on, attached to, or placed upon the substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly) tetrafluoroethylene, (poly)vinylidenedifluoride, polystyrene, cross-linked polystyrene, polyacrylic, polylactic acid, polyglycolic acid, poly(lactide coglycolide), polyanhydrides, poly (methyl methacrylate), poly(ethylene-co-vinyl acetate), polysiloxanes, polymeric silica, latexes, dextran polymers, epoxies, polycarbonate, or combinations thereof.

Substrates can be planar crystalline substrates such as silica-based substrates (e.g. glass, quartz, or the like), or crystalline substrates used in, e.g., the semiconductor and microprocessor industries, such as silicon, gallium arsenide and the like.

Silica aerogels can also be used as substrates, and can be prepared by methods known in the art. Aerogel substrates may be used as freestanding substrates or as a surface coating for another substrate material.

The substrate can take any form and typically is a plate, slide, bead, pellet, disk, particle, strand, precipitate, membrane, optionally porous gel, sheets, tube, sphere, container, capillary, pad, slice, film, chip, multiwell plate or dish, optical fiber, and the like. The substrate may contain raised or depressed regions on which an encoded cell is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si—OH functionalities, such as those found on silica surfaces.

The substrate and/or its optional surface are chosen to provide appropriate optical characteristics for the synthetic and/or detection methods used. The substrate and/or surface can be transparent to allow the exposure of the substrate by light applied from multiple directions. The substrate and/or surface may be provided with reflective "mirror" structures to increase the recovery of light emitted by the semiconductor nanocrystal or other label. The substrate and/or its surface may also be coated to decrease the amount of spurious incident light.

The substrate and/or its surface is generally resistant to, or is treated to resist, the conditions to which it is to be exposed in use, and can be optionally treated to remove any resistant material after exposure to such conditions.

SCNCs as Labels to Study Intracellular Protein/Protein Interactions.

Figure 5:
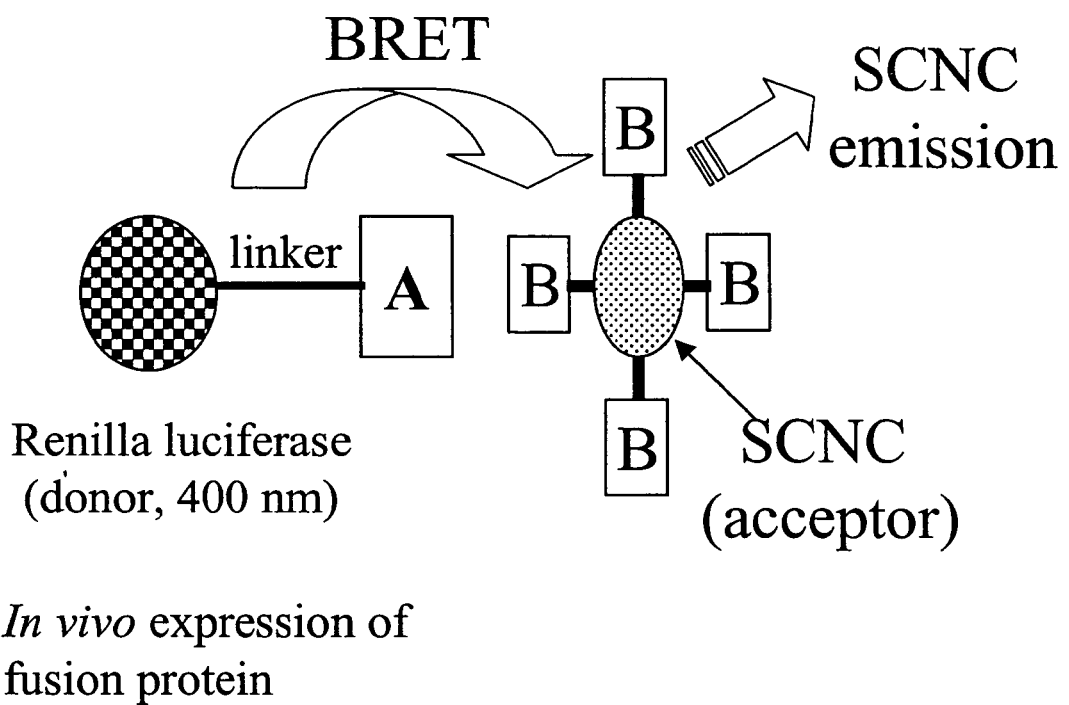
FIG. 5 depicts a bioluminescence resonance energy transfer experiment using semiconductor nanocrystals linked to a prospective binding partner for a protein of interest; this conjugate is introduced into cells expressing a fusion protein between the protein of interest and a luciferase to determine if fluorescence transfer occurs from the luciferase to the semiconductor nanocrystal in vivo.

To measure intracellular protein/protein interactions, a cell line expressing, for example, a gene fusion of renilla luciferase and a protein of interest (protein A) can be used. An SCNC, conjugated to a potential interacting protein (protein B), is delivered into cells using the Chariot reagent, a peptide reagent based on the HIV-tat sequence (see Example 1). The binding of protein A and protein B is measured by bioluminescence resonance energy transfer (BRET). See FIG. 5. The light emitted by renilla luciferase is transferred to the SCNC only if protein A is bound to protein B, and the distance between luciferase and the SCNC is less than 100 angstroms. Alternatively, several different SCNC/protein conjugates are delivered into cells and their interactions with protein A are studied in real time by measuring the SCNC emission properties. This approach can be used to study the assembly of complex structures such as transcription factor complexes or the splicesome inside living cells.

Encoding DNA Transfections to Screen, in a Combinatorial Fashion, the Functions of Genes Identified in Gene Expression Microarray Experiments.

As explained above, there are a number of distinct methods for delivering SCNCs into cells. One of these methods relies on a cationic lipid that is similar to commercial reagents for transfecting DNA molecules into cells which can be used to co-deliver DNA and SCNC codes into cells. The encoding of DNA transfections greatly facilitates the functional analysis of genes identified in microarray experiments. For example, a microarray experiment can identify hundreds of genes that are specifically turned on in response to a compound that induces cell apoptosis. To identify single genes or gene combinations responsible for the apoptotic phenotype, for example, many separate DNA transfections and assays are required using conventional methods. Multiplexing the assays with encoded DNA greatly facilitates these assays because the genotype is linked to phenotype via an easily read optical SCNC code. The encoded transfectants are mixed and added to wells, and the effects of a specific compound or incubation condition can be screened simultaneously against the phenotypes of many gene combinations within a single well.

Encoded Cells for Multiplex Screening of Different Drug Targets Expressed in a Common Host Cell Line Encoded cell technology can be used to screen multiple targets simultaneously in the same assay well. Each target is expressed in a common host cell line, and the identity of the receptor is encoded in the semiconductor nanocrystal code. Examples of high-value drug targets and corresponding cell-based assays include the following:

G protein coupled receptors: competition binding assays, reporter gene assays, calcium assays;

Ion channels: competition binding assays, reporter gene assays, calcium assays, membrane potential assays;

Nuclear receptors: reporter gene assays, calcium assays; and

Cytokine receptors: competition binding assays, reporter gene assays, calcium assays.

Encoded Cells for Comparing Complex Phenotypes Among Different Cell Types

Encoded cell technology is not limited to target-specific cell based assays. A complex phenotype, such as apoptosis or cell migration, can be compared between different cell types in the same assay well because each cell type is encoded with a unique SCNC code. Multiplexing complex phenotypic assays in the same assay well may be valuable for kinetic assays, or for measuring the effects of a single compound on cell-type specific responses. Examples of such phenotypic assays include the following: apoptosis, cell migration, cytoplasm to nucleus translocation, retrograde transport, neurite outgrowth, and receptor internalization.

Figure 6:
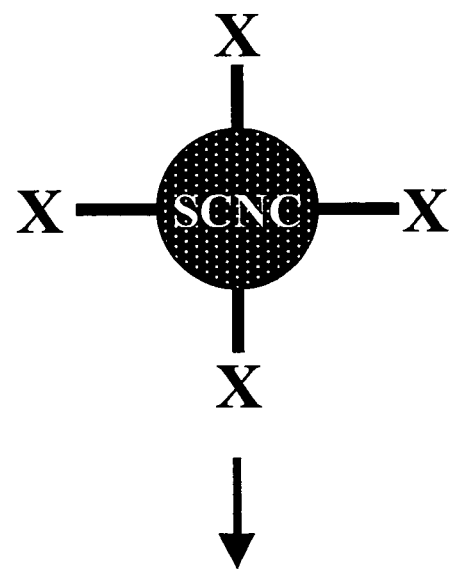
FIG. 6 depicts the conjugation of semiconductor nanocrystals to different types of proteins for use in affinity targeting of cells and subcellular structures.

SCNCs as Labels for Imaging Intracellular Organelles or Studying Protein Trafficking in Live Cells Delivery of SCNCs conjugated to specific peptides, proteins or antibodies into cells may provide a new and powerful method for live cell imaging (FIG. 6, in which X is, for example, a peptide ligand, protein, localization sequence or antibody). A peptide sequence may act as an affinity handle for binding the SCNC to a specific intracellular target, or it can target the SCNC to a specific intracellular organelle. Mulitiplex analysis of several proteins in a live cell is invaluable in screening and target validation applications.

Encoding Fixed Cells for Histochemical Applications

Encoded cell technology can also be used to multiplex any histochemical staining assay. For example, kits are commercially available for measuring the cytoplasm to nucleus translocation of several transcription factors (Cellomics). The kit is comprised of an Alexa-488-conjugated antibody that recognizes a specific transcription factor, and buffers to fix and mount the cells. Cells are incubated and fixed at various times after adding a compound, and the cytoplasm to nucleus translocation of the transcription factor is measured by fluorescence microscopy. Different encoded cell types can be used to study the translocation of a single protein among different cell types. Thus, the effect of a single compound can be screened for its ability to block or activate the translocation of a protein among different cell types.

Examples of Cellomics kits that can be encoded with SCNCs include those for NFcB, STAT1, STAT2, STAT3, STATS, c-Jun, ATF-2, p38 MAPK, JNK/SAPK, ERK MAPK.

Other cell-based assay kits that can be used with encoded cells include cell viability, neurite outgrowth, apoptosis, mitotic index, cell motility, and receptor internalization.

Multiplex Screening of Cell Viability

Figure 7:
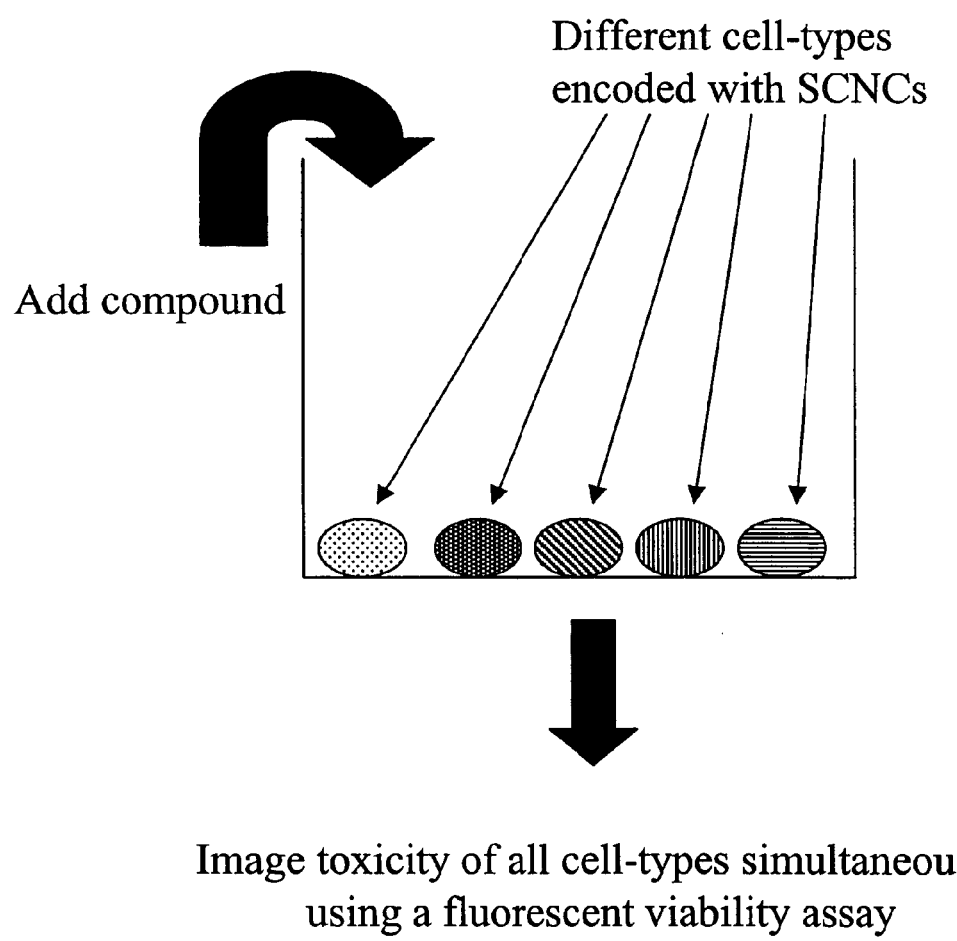
FIG. 7 depicts the toxicity screening in a single well of a single compound against a plurality of cell types encoded through the techniques described herein.

A single compound can be screened for toxicity against multiple cell types in a single well (FIG. 7).

Selectivity Profiling as a Tool for Predicting Compound Toxicity.

Encoded cells can be used to measure the selectivity of compounds against many drug targets and cell types. This information can be used to predict toxicity, because many compounds are toxic due to non-selective interactions.

Selectivity Profiling as a Tool to Increase the Efficiency of Lead Optimization

Selectivity profiling can also aid lead optimization. A thorough understanding of target selectivity at an early stage in the drug discovery pipeline can lead to better choices for lead optimization.

Figure 8:
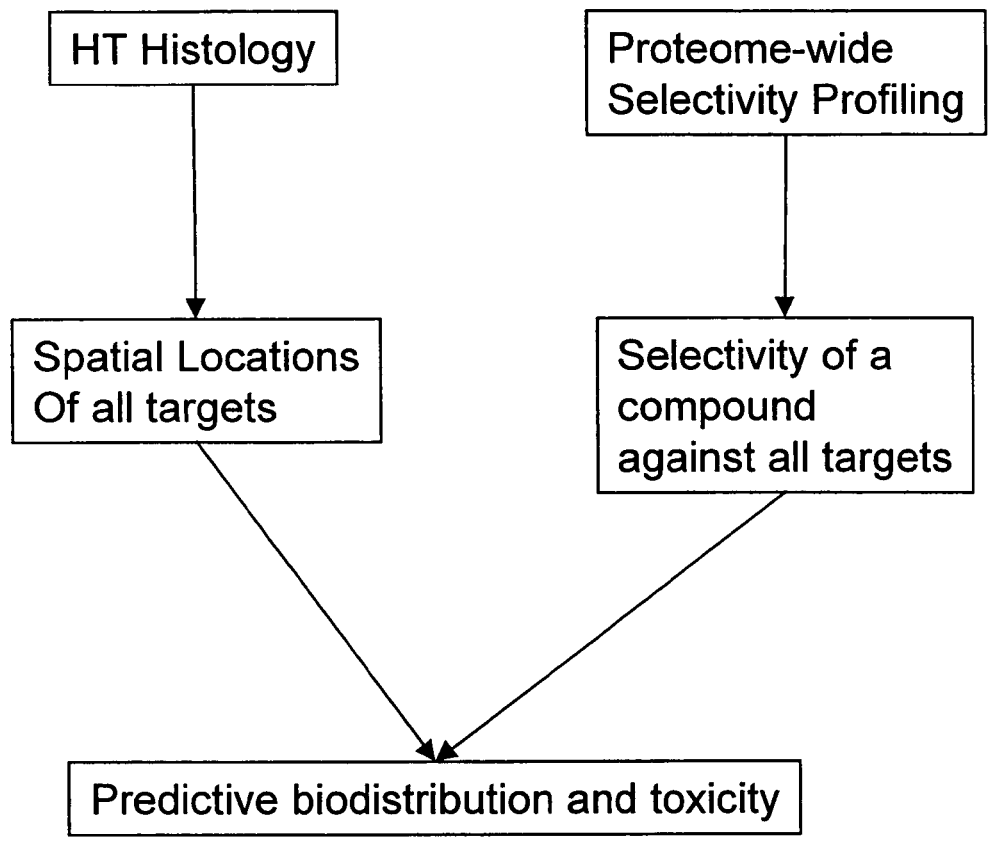
FIG. 8 depicts a predictive in silico biodistribution and toxicity model that integrates high throughput histological information regarding prospective targets with a compound's proteome-wide selectivity against those targets.

Combining Target Distribution and Compound Selectivity to Predict Biodistribution of Compounds Combining a compound's proteome-wide selectivity with the proteome-wide tissue distribution of targets enables predictive in silico biodistribution models (FIG. 8).

Transporter Assays

Transporter proteins are a high-value target class because of their role in drug uptake. For example, selective serotinin reuptake inhibitors (SSRIs) interact with the serotonin transporter protein. SCNCs can be applied to transporter assays in several ways. First, SCNCs can be conjugated to transporter ligands and used in competition uptake assays to screen for compounds that block uptake of the SCNC conjugate. Another use is to encode cell lines expressing different transporters and to compare the uptake efficiency of a fluorescent-labeled ligand among different transporter types.

Figure 9:
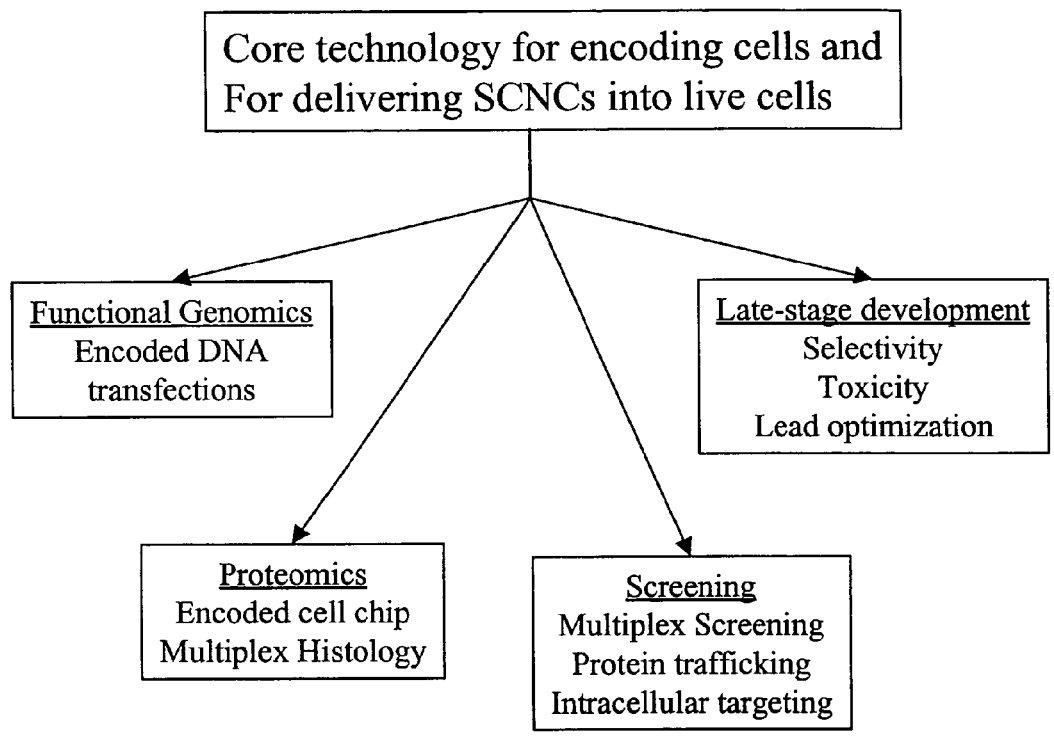
FIG. 9 lists some of the wide range of applications for cells encoded with semiconductor nanocrystals.

Thus, the applications of encoded cells are extremely wide-ranging (FIG. 9).

GPCR Pathway Assays

The present invention provides a method of screening test compounds and test conditions for the ability to modulate (activate or inhibit, enhance or depress) a GPCR pathway, and provides methods of assessing GPCR pathway function, such as the function of an orphan GPCR, in a cell in general. In the present methods, SCNCs are coupled with a candidate ligand or a library of candidate ligands, as detailed above, and translocation of the ligand by the GPCR pathway is followed by detecting the spatial location of SCNCs, or the change in spatial location of SCNCs, in extracellular fluid (natural or artificial, e.g., a growth or assay medium), in a cell, the cell cytosol, a cell membrane, or an intracellular compartment or membrane, e.g., an intracellular vesicle, the cell nucleus or nuclear membrane, mitochondria or mitochondria membrane, golgi apparatus, other organelle, or other intracellular compartment or membrane. The relative extent of translocation or change of spatial location of SCNCs under varied test conditions may be compared, or a test condition may be compared, to a control condition or to a predetermined standard. Depending on the assay design, the determination of translocation of the ligand is an indicator of modulation, e.g., agonist stimulation, of GPCR activity or of the presence of a GPCR in a cell, in a cell membrane or the like.

Translocation of the ligand is evidenced by an increase in the intensity of the detectable signal located within the cell cytosol, cell membrane, or an intracellular compartment and/or a decrease in the intensity of the detectable signal located within the cytosol, membrane, or intracellular compartment, wherein the change occurs after exposure to the test compound. Translocation may thus be detected by comparing changes in the detectable signal in the same cell over time (i.e., pre- and post-exposure to the test compound or to one or more members of the library of test compounds). Alternatively, a test cell may be compared to a pre-established standard. If a known modulator, e.g., an agonist or antagonist ligand, is available, the present methods can be used to screen a chemical compound library for and study candidate GPCR agonists and antagonists.

The methods of the present invention provide easily detectable results. For example, translocation of a ligand, such as a GPCR ligand or beta-arrestin, coupled to an SCNC, in response to GPCR activation or inhibition, results in a relative change in the spatial location of the detectable signal within the cell cytosol, membrane or intracellular compartment. In addition, the concomitant decrease in detectable signal from the original location of the signal in the cell cytosol, membrane or intracellular compartment can be used to measure translocation of the ligand. In certain cells, the activation of the GPCRs will result in essential clearing of detectable signal from the original location of the signal, and an concomitant increase in the detectable signal within the cell cytosol, membrane or intracellular compartment. In the present methods, it is preferred that the assay design results in an increase in the detectable signal within the cell cytosol, membrane or intracellular compartment after GPCR activation. Preferably, the signal will increase at least two-fold, more preferably at least three-fold, still more preferably at least five-fold, and most preferably at least ten-fold.

In one embodiment, the present invention provides a method for screening modulators of GPCR activity comprising: a) providing a cell expressing a known or unknown GPCR, wherein the cell is encoded with an SCNC, other detectable label as disclosed herein or combination thereof; b) exposing the cell to a test compound; c) detecting the signal from the SCNC; and (d) comparing the signal produced in the presence of the test compound with the signal produced in the absence, wherein changes in the spatial location of the signal indicates that the compound is a modulator of a GPCR.

In another embodiment, the present invention provides a method for screening candidate GPCR modulator compounds comprising: a) providing a cell expressing a known or unknown GPCR; b) contacting the cell with a translocatable ligand that is conjugated to a SCNC; c) exposing the cell to a predetermined concentration of a test compound or each member of a library of test compounds; d) detecting the translocation of the translocatable ligand into the cell cytosol, cell membrane or intracellular compartment, and comparing the translocation in the presence and absence of the candidate modulator.

In yet another embodiment, the present invention provides methods for screening a cell or a population of cells for the presence of a GPCR, comprising (a) providing a cell or a population of cells; (b) associating the cell or population of cells with an SCNC; (c) exposing the cell or population of cells to a test solution containing a known agonist to a GPCR; and either (d) detecting in the cell translocation of a translocatable ligand either (i) from the cellular membrane to the cytosol of the cell or to an intracellular compartment or (ii) from the cytosol of the cell to the membrane, and subsequently to an intracellular compartment, (iii) from the cytosol to an intracellular compartment, or (iv) from one intracellular compartment to another intracellular compartment, or (e) detecting those cells in which translocation of the translocatable ligand occurs, wherein the translocation of the ligand indicates the presence of such a GPCR. Translocation of the ligand can be detected as discussed above. Populations of cells to be screened are discussed above, and can additionally include a tissue, an organ, or an organism.

The present invention thus provides a convenient method of identifying modulators for an orphan GPCR. Orphan GPCRs are novel receptors and are typically identified by the sequence comparison-based methods, but whose cognate ligands are not known. It is estimated that from 400 to as many as 5000 orphan GPCRs may be coded for in the human genome, representing a vast potential for developing new drugs.

The present invention provides a convenient and efficient method for identifying a natural or synthetic ligand that initiates orphan GPCR activation, and for identifying ligands that inhibit such activation, thereby characterizing the pharmacology of the orphan GPCR. The method of the invention can be used to detect the orphan GPCRs GPCR10, OX1R and OX2R, and GPCR 24 using the ligands prolactin-releasing peptide, orexin-A/orexin-B, and melanin concentrating hormone, respectively. Thus, the functions of orphan GPCRs can be identified as controlling feeding behavior.

Preparation of Cells that Express GPCRs

Methods for preparing cells that express GPCRs have been described. See, e.g., U.S. Pat. Nos. 6,051,386, 6,069,296, 6,111,076 and 6,280,934, the disclosures of which are incorporated herein by reference. Generally, complementary DNA encoding GPCRs can be obtained and can be expressed in an appropriate cell host using techniques well known in the art. Typically, once a full-length GPCR cDNA has been obtained, it can be expressed in a mammalian cell line, yeast cell, amphibian cell or insect cell for functional analysis. Preferably, the cell line is a mammalian cell line that has been characterized for GPCR expression and that optionally contains a wide repertoire of G-proteins to allow functional coupling to downstream effectors. Examples of such cell lines include Chinese Hamster Ovary (CHO) or Human Embryonic Kidney 293 (HEK293) lines. Cells in which the cDNA is expressed can be encoded using the methods disclosed herein, thus allowing the multiplex screening of ligands. The expressed receptor can then be screened in a variety of functional assays to identify an activating ligand as disclosed above and in U.S. Pat. Nos. 6,051,386, 6,069,296, 6,111,076 and 6,280,934. Preferably, the functional assay methods use SCNCs, although other functional responses can be monitored can also be used. Other functional responses include changes in intracellular calcium or cAMP levels, and metabolic activation, which can be measured using the Cytosensor microphysiometer. In another embodiment, the receptor is co-expressed with promiscuous G-proteins thereby aggregating signal transduction through a common pathway involving phospholipase C and calcium mobilization. Changes in calcium mobilization may be detected using SCNCs, as discussed above, or via standard fluorescence-based techniques using a high throughput imaging system such as FLIPR® (Fluorescent Imaging Plate Reader). Examples of high throughput microscopes include Discovery 1 from Universal Imaging Corporation, CeilPix from Axon Instruments, LeadSeeker from Amersham/Pharmacia, and Explorer from Acumen. The ability to screen in a high-throughput manner permits the screening of orphan receptors against a wide range of candidate ligands, such as those contained in a library. The library of candidate ligands may contain known or suspected GPCR ligands, as well as molecules for which the receptor is unknown. In addition, the methods of the invention permit screening against biological extracts of tissues, fluids, and cell supernatants, thereby identifying novel ligands for GPCRs. Additionally, the methods of the invention can be used to screen against peptide libraries or compound libraries. Once an activating ligand is obtained, high-throughput screens of the invention can be used to search for modulators of the receptor, such as agonists and antagonists. The invention thus allows for the identification of various agonists and antagonists of the known and orphan GPCRs that can be used to evaluate the physiological role of the receptor and its potential as a therapeutic target for drug discovery.

Kits

Kits comprising reagents useful for performing the methods of the invention are also provided. The components of the kit are retained by a housing. Instructions for using the kit to perform a method of the invention are provided with the housing, and may be located inside the housing or outside the housing, and may be printed on the interior or exterior of any surface forming the housing which renders the instructions legible. In one embodiment, a kit comprises an SCNC population, and a reagent useful for encoding a cell using the SCNC population. Exemplary reagents useful for encoding a cell are described above. These reagents may be used alone or in combination. Additionally, the kit may be designed for multiplex applications and contain a plurality of SCNC populations useful for simultaneously encoding a plurality of different cell populations.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Preparation of Polymer-Coated SCNCs

A. Synthesis of Hydrophobically Modified Hydrophilic Polymers: A modified polyacrylic acid was prepared by diluting 100 g [0.48 mol COONa] of poly(acrylic acid, sodium salt) (obtained from Aldrich, molecular weight 1200) was diluted two-fold in water and acidified in a 1.0 L round bottom flask with 150 ml (1.9 mol) of concentrated HCl. The acidified polymer solution was concentrated to dryness on a rotary evaporator (100 mbar, 80° C.). The dry polymer was evacuated for 12 hours at <10 mbar to ensure water removal. A stirbar and 47.0 g (0.24 mol) of 1-[3-(dimethylamino)-propyl]-ethylcarbodiimide hydrochloride (EDC-Aldrich 98%) were added to the flask, then the flask was sealed and purged with $N_2$, and fit with a balloon. 500 ml of anhydrous N-N, dimethylformamide (Aldrich) was transferred under positive pressure through a cannula to this mixture; and the flask was swirled gently to dissolve the solids. 32 ml (0.19 mol) of octylamine was transferred dropwise under positive pressure through a cannula from a sealed oven-dried graduated cylinder into the stirring polymer/EDC solution, and the stirring continued for 12 hours. This solution was concentrated to <100 ml on a rotary evaporator (30 mbar, 80° C.), and the polymer was precipitated by addition of 200 ml di-$H_2O$ to the cooled concentrate, which produced a gummy white material. This material was separated from the supernatant and triturated with 100 ml di-$H_2O$ three more times. The product was dissolved into 400 ml ethyl acetate (Aldrich) with gentle heating, and basified with 200 ml di-$H_2O$ and 100 g N-N-N-N-tetramethylammonium hydroxide pentahydrate (0.55 mo) for 12 hours. The aqueous layer was removed and precipitated to a gummy white product with 400 ml of 1.27 M HCl. The product was decanted and triturated with 100 ml of di-$H_2O$ twice more, after which the aqueous washings were back-extracted into 6×100 ml portions of ethyl acetate. These ethyl acetate solutions were added to the product flask, and concentrated to dryness (100 mbar, 60° C.). The crude polymer was dissolved in 300 ml of methanol and purified in two aliquots over LH-20 (Amersham-Pharmacia-5.5 cm×60 cm column) at a 3 ml/minute flow rate. Fractions were tested by NMR for purity, and the pure fractions were pooled, while the impure fractions were re-purified on the LH-20 column. After pooling all of the pure fractions, the polymer solution was concentrated by rotary evaporation to dryness, and evacuated for 12 hours at <10 mbar. The product was a white powder (25.5 g, 45% of theoretical yield), which showed broad NMR peaks in $CD_3OD$ [d=3.1 b (9.4), 2.3 b (9.7), 1.9 1.7 1.5 1.3 b (63.3) 0.9 bt (11.3)], and clear IR signal for both carboxylic acid (1712 $cm^{-1}$) and amide groups (1626 $cm^{-1}$, 1544 $cm^{-1}$).

B. Preparation of Surface-Modified Nanocrystals: Twenty milliliters of 3-5 mM 3-5 nmoles) of TOPO/TOP coated CdSe/ZnS nanocrystals (see, Murray et al. (1993) *J. Am. Chem. Soc.* 115:8706) were precipitated with 20 milliliters of methanol. The flocculate was centrifuged at 3000×g for 3 minutes to form a pellet of the nanocrystals. The supernatant was thereafter removed and 20 milliliters of methanol was again added to the particles. The particles were vortexed to loosely disperse the flocculate throughout the methanol. The flocculate was centrifuged an additional time to form a pellet of the nanocrystals. This precipitation/centrifugation step was repeated an additional time to remove any excess reactants remaining from the nanocrystal synthesis. Twenty milliliters of chloroform were added to the nanocrystal pellet to yield a freely dispersed sol.

300 milligrams of hydrophobically modified poly(acrylic acid) was dissolved in 20 ml of chloroform. Tetrabutylammonium hydroxide (1.0 M in methanol) was added to the polymer solution to raise the solution to pH 10 (pH was measured by spotting a small aliquot of the chloroform solution on pH paper, evaporating the solvent and thereafter wetting the pH paper with distilled water). Thereafter the polymer solution was added to 20 ml of chloroform in a 250 ml round bottom flask equipped with a stir bar. The solution was stirred for 1 minute to ensure complete admixture of the polymer solution. With continued stirring the washed nanocrystal dispersion described above was added dropwise to the polymer solution. The dispersion was then stirred for two minutes to ensure complete mixing of the components and thereafter the chloroform was removed in vacuo with low heat to yield a thin film of the particle-polymer complex on the wall of the flask. Twenty milliliters of distilled water were added to the flask and swirled along the walls of the flask to aid in dispersing the particles in the aqueous medium. The dispersion was then allowed to stir overnight at room temperature. At this point the nanocrystals are freely dispersed in the aqueous medium, possess pendant chemical functionalities and may therefore be linked to affinity molecules of interest using methods well known in the art for biolabeling experiments. In addition, the fact that the nanocrystals now have a highly charged surface means they can be readily utilized in polyelectrolyte layering experiments for the formation of thin films and composite materials.

C. Crosslinking of Polymer Stabilized Nanocrystals with a Diamino Crosslinker: Ten milliliters of nanocrystals at 3.5 µM, stabilized as described supra, were purified by tangential flow filtration using a 100 K polyethersulfone membrane against one liter of distilled water and one liter of 50 mM Morpholinoethanesulfonic acid buffer, pH 5.9. The nanocrystals were concentrated to 10 milliliters and the pH of the aqueous dispersion was decreased to pH 6.5 with 50 µl additions of 0.1M HCl. 67 milligrams (315 µmoles) EDC were added to the stirring nanocrystal dispersion. The reaction was allowed to proceed for 10 minutes before 1 milliliter of 0.5M borate buffer (pH 8.5) containing 3.94 µmoles of the crosslinking reagent lysine (a diamino carboxylic acid) were added to the reaction mixture. The reaction mixture was stirred for 2 hours at room temperature and then transferred to a 50,000 molecular weight cut-off polyethersulfone dialysis bag. Dialysis was performed for 24 hours against 2 changes of 4 liters of water.

Example 1

Peptide-Mediated Uptake of SCNCs

Chariot (Active Motif, Carlsbad, Calif.) is a peptide reagent based on the HIV-tat sequence (Schwarze et al.

(1999) *Science* 285:1569-1572), and has been used to deliver a variety of macromolecules into cells. Chariot forms a non-covalent complex with a molecule of interest (protein, peptide, antibody, or SCNC), and acts as a carrier to deliver molecules into cells.

To deliver SCNCs into cells using Chariot, tissue culture cells were seeded into six-well tissue culture plates (surface area of 962 mm$^2$ per well) at a cell density of 3×10$^5$ cells per well and incubated overnight at 37° C. in a 5% $CO_2$ atmosphere. The transfection efficiency was dependent on the percent confluency of cells; the optimal percent confluency for Chinese Hamster Ovary (CHO) cells was about 50-70%.

The transfection mixture was prepared by first diluting 616 nm emitting SCNCs into PBS in a final volume of 100 µl. The diluted SCNCs were combined with a mixture containing 94 µl sterile water and 6 µl Chariot reagent, and the 200 µl transfection mix was incubated at room temperature for 30 min.

To transfect, cells were rinsed with PBS, and the 200 µl transfection mix was added directly to the cell monolayer, followed by 400 µl of serum-free growth medium. The final SCNC concentration ranged from 10 to 120 nM, depending on the cell type and SCNC material. The cells were incubated at 37° C., 5% $CO_2$ for 1 hour, and 1 ml of serum containing growth medium was added to each well. The cells were allowed to incubate for an additional 2 hours. To visualize internalized SCNCs, the cells were analyzed by fluorescence microscopy (FIG. 10) or flow cytometry using the appropriate filter sets.

Example 2

Nonspecific Uptake of SCNCs

Figure 11:
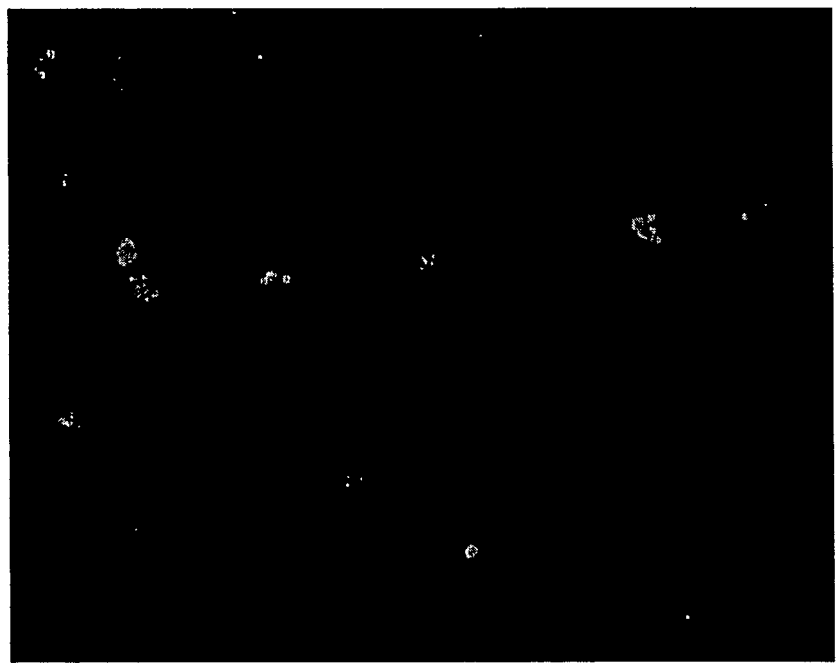
FIG. 11 is a fluorescence micrograph of CHO cells incubated with 40 nM noncrosslinked polymer SCNC as described in Example 2.

SCNCs can be internalized by cells in the absence of a specific carrier molecule. Non-crosslinked polymer-coated SCNCs prepared as described above are sufficiently hydrophobic that they bind to cells and are taken up by nonspecific endocytotic pathways. Cells encoded with SCNCs were prepared as described in Example 1, except the Chariot reagent was omitted from the transfection mix. An example of nonspecific uptake of SCNCs is shown in FIG. 11.

Example 3

Cationic Lipid-Mediated and Micelle-Mediated Uptake of SCNCs

BioPORTER (BioPORTER, Gene Therapy Systems, San Diego, Calif.) is a cationic lipid that is similar to other lipid-based reagents for DNA transfections. It forms ionic interactions with negatively charged groups of a molecule (protein, peptide, antibody, or SCNC), and delivers the molecule into cells via fusion with the cell membrane.

Figure 12:
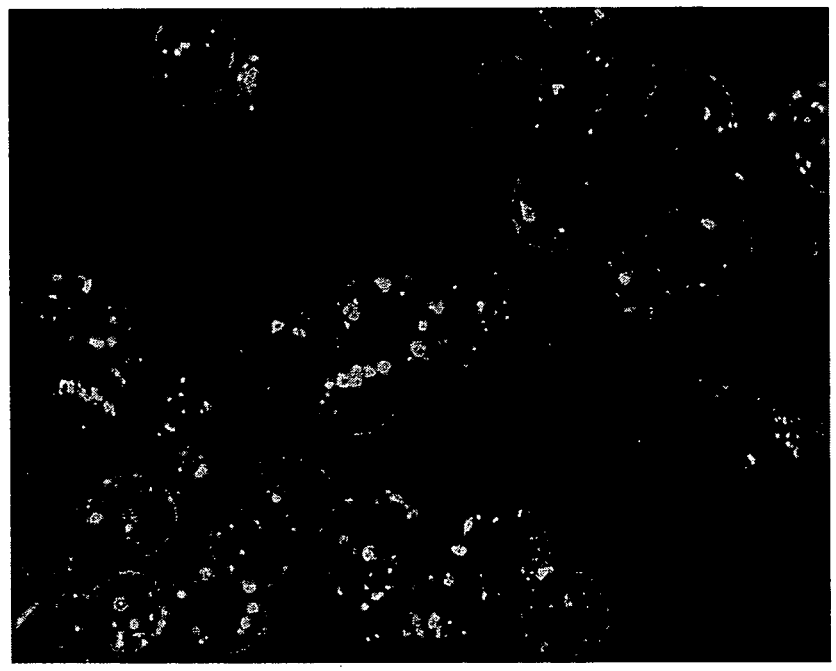
FIG. 12 is a fluorescence micrograph of SKBR3 breast cancer cells and green SCNCs transfected using BioPORTER reagent as described in Example 3. Cells were also stained with herceptin antibody.

Cells were seeded at the same density as described in Example 1. A transfection mix, comprised of carboxylated SCNCs and PBS in a final volume of 100 µl, was added to a tube containing 10 µl of dried BioPORTER reagent. The solution was mixed gently by pipetting, incubated at room temperature for 5 minutes, and diluted by adding 900 µl of serum free medium. Cells were washed with PBS, and the diluted SCNC solution (1 ml) was added to the cell monolayer. The final SCNC concentration was 2-60 nM, depending on the cell line and SCNC material being tested. The cells were incubated at 37° C., 5% $CO_2$ for 3 hr, and internalized SCNCs were visualized by fluorescence microscopy (FIG. 12). Alternatively, 3 ml of serum-containing medium was added to each well and the cells were incubated overnight for analysis the next day.

Micelle-Mediated Uptake of SCNCs

SCNCs were stabilized by entrapping phosphine/phosphine oxide ligands onto the surface of SCNCs with specific polymers through hydrophobic interaction. The most common ligands used in the synthesis of SCNCs are TOP and TOPO. TOP and TOPO bind to the surface Cd or Se through P-metal bond and their hydrophobic octyl chains are pointing toward solvent making the surface of SCNCs hydrophobic. Partially grafted poly(acrylic acid) (PAA), in which octylamines were attached to about 40% carboxyl groups of PAA through amide bond formation, were adsorbed onto the hydrophobic surface of SCNCs through hydrophobic interaction, leading water-soluble SCNCs. The remaining carboxyl groups can be used to conjugate to biological molecules or to be crosslinked with each other in order to make stable SCNCs.

In another method, the hydrophilic shell of micelles was chemically crosslinked, where the surface of the micelles is made up with carboxyl groups, which can then be used to form bioconjugates for biological applications. The amphiphilic block copolymer entraps or encapsulates SCNCs rendering the SCNCs water-soluble. The polymers can be diblock, triblock or multiblock copolymer, which contains at least one block of a hydrophobic segment and at least one block of hydrophilic segment. The surface of the micelles or functional groups in hydrophilic block of the block copolymer can be carboxyl, aldehyde, alcohol, amine or any reactive groups. The micelles encoded with one or more SCNCs were further stabilized through crosslinking of the hydrophilic shell.

For micelle-mediated uptake of SCNC, cells and aqueous solutions of SCNCs trapped in micelles were prepared as described above. To transfect, a mixture comprised of SCNCs/micelles and serum free medium was prepared at a final volume of 500 ul and incubated for 5 min at room temperature.

Cells were washed with PBS, and the transfection mixture was added to the cell monolayer such that the final SCNC/micelle concentration was approximately 20 nM. Cells were incubated at 37° C., 5% $CO_2$ for 1 hr, and 1 ml of serum containing growth medium was added to each well. The cells were incubated for an additional 2 hr and analyzed. To analyze cells the following day, 2 ml of serum containing medium was added and the cells were incubated overnight. The incorporation of SCNCs into the cells was detected by fluorescence microscopy using a 535 nm emission filter or a 625 nm emission filter.

Example 4

Co-Delivery of DNA and SCNCs

It is possible to co-deliver SCNCs and DNA using cationic lipids for encoded DNA transfection applications. A transfection solution comprised of 2 nM red (emitting at 630 nm) SCNC polymer cross-linked prepared as described above, and 3 µg of DNA carrying an EGFP (enhanced green fluorescent protein)/rac kinase fusion sequence was prepared and added to the BioPORTER reagent as described in Example 3. Cells were cultured 2 days for EFGP expression and analyzed by fluorescence microscopy and flow cytometry. The microscopy results show that it was possible to find cells that expressed EGFP and contained red SCNCs (FIG. 13). Control experiments using the EGFP fusion DNA or red SCNCs alone suggest that the DNA transfection efficiency decreased in the presence of SCNCs. This may be caused by SCNC competing with DNA for the BioPORTER reagent.

Example 5

Decoding of SCNC-Labeled Cells

Figures 14, 14A, 14B:
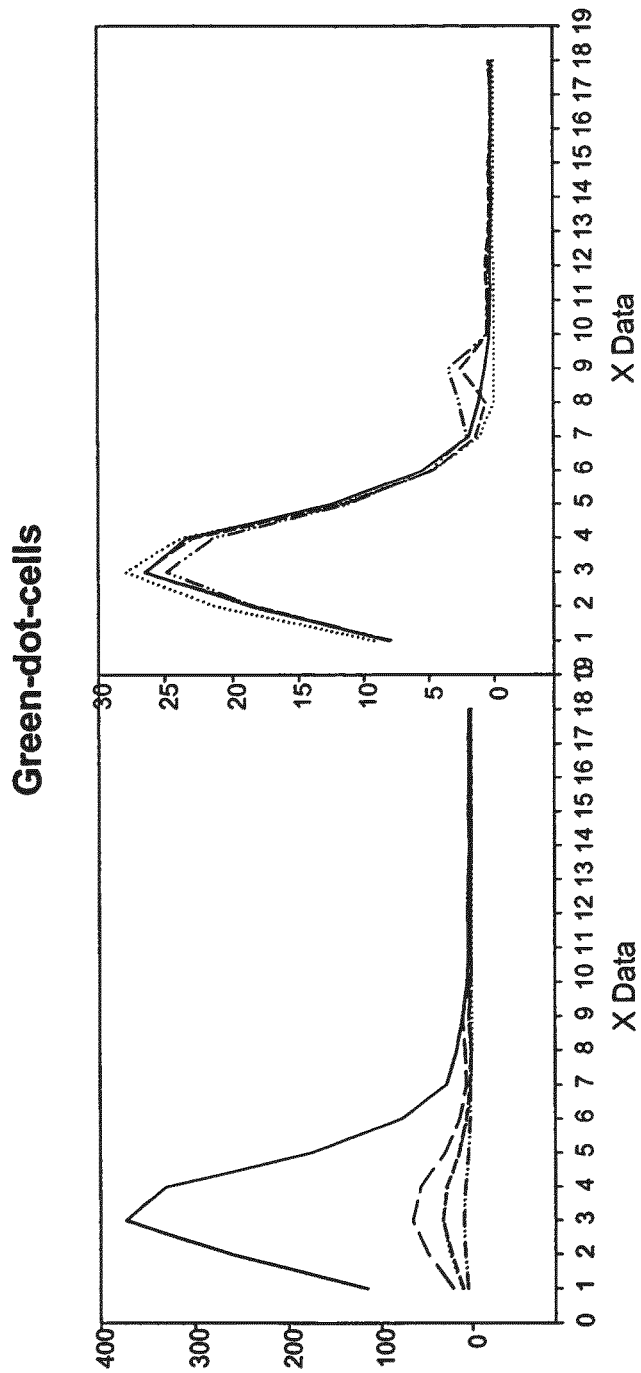
FIG. 14 is a graphical representation of spectra (raw, FIG. 14A; normalized, FIG. 14B) and of four individual CHO cells encoded with green SCNCs using Chariot reagent as described in Example 5.
Figures 15, 15A, 15B:
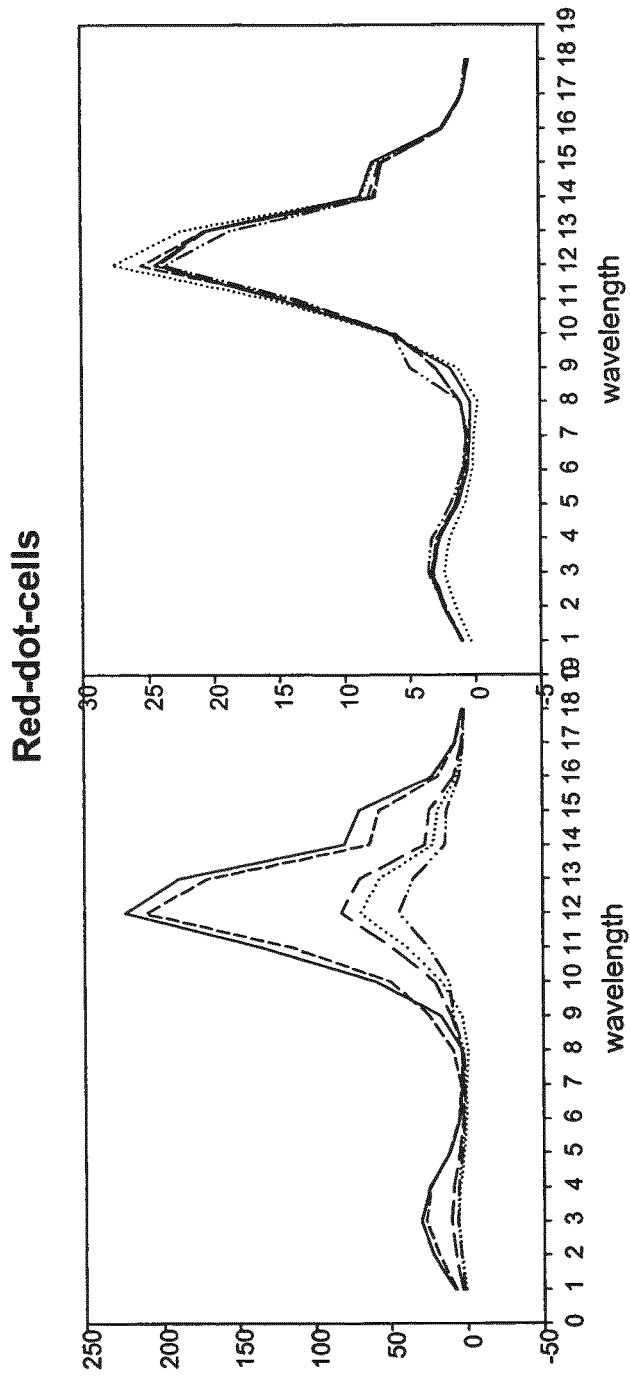
FIG. 15 is a graphical representation of spectra (raw, FIG. 15A; normalized, FIG. 15B) of five individual CHO cells encoded with red SCNCs using Chariot reagent as described in Example 5.

SCNC codes can be detected inside cells using the green (530 nm) or red (630 nm) crosslinked polymer-coated SCNCs prepared as described above were delivered into CHO cells as single colors or mixtures of two colors using the Chariot reagent. Individual cells were identified and analyzed over the range of 510 nm to 680 nm using an 18-filter set. The results show that for individual cells, absolute SCNC fluorescence intensity can vary more than 10-fold, but that normalized spectral patterns are very similar for green or red SCNCs (FIGS. 14 and 15). Mixing green and red SCNCs prior to adding them to the cell monolayer results in cells that also have very similar spectral patterns after fluorescence normalization (FIG. 16). Thus, these results suggest that pattern recognition can be used as an encoding strategy for cells.

Example 6

Encoding Multiple Cell Lines with SCNCs

A first cell line expressing a G-protein coupled receptor, e.g., a serotonin receptor, is taken into suspension and fixed in an appropriate fixative (e.g., 3% paraformaldehyde). A specific mixture of SCNCs having known fluorescence characteristics is used to encode this population of cells. A second cell line expressing a different G-protein coupled receptor, e.g., a beta adrenergic receptor, is encoded with a second spectral code in a similar manner. The first and second spectral codes have distinguishable fluorescence characteristics.

The separately encoded cells are then mixed together in the well of a microtiter plate and this mixed population is interrogated with a labeled ligand (labeled with either a fluorophore or a SCNC detectable different from the code) which may or may not bind to the G-protein coupled receptors on the cell lines. After an incubation period the encoded cells are allowed to settle to the bottom of the well and each encoded population of cells is measured to determine if label is associated with it using a scanning spectrometer based detection system.

Example 7

Incorporation of SCNC into Yeast Mutant Cells

Figure 17:
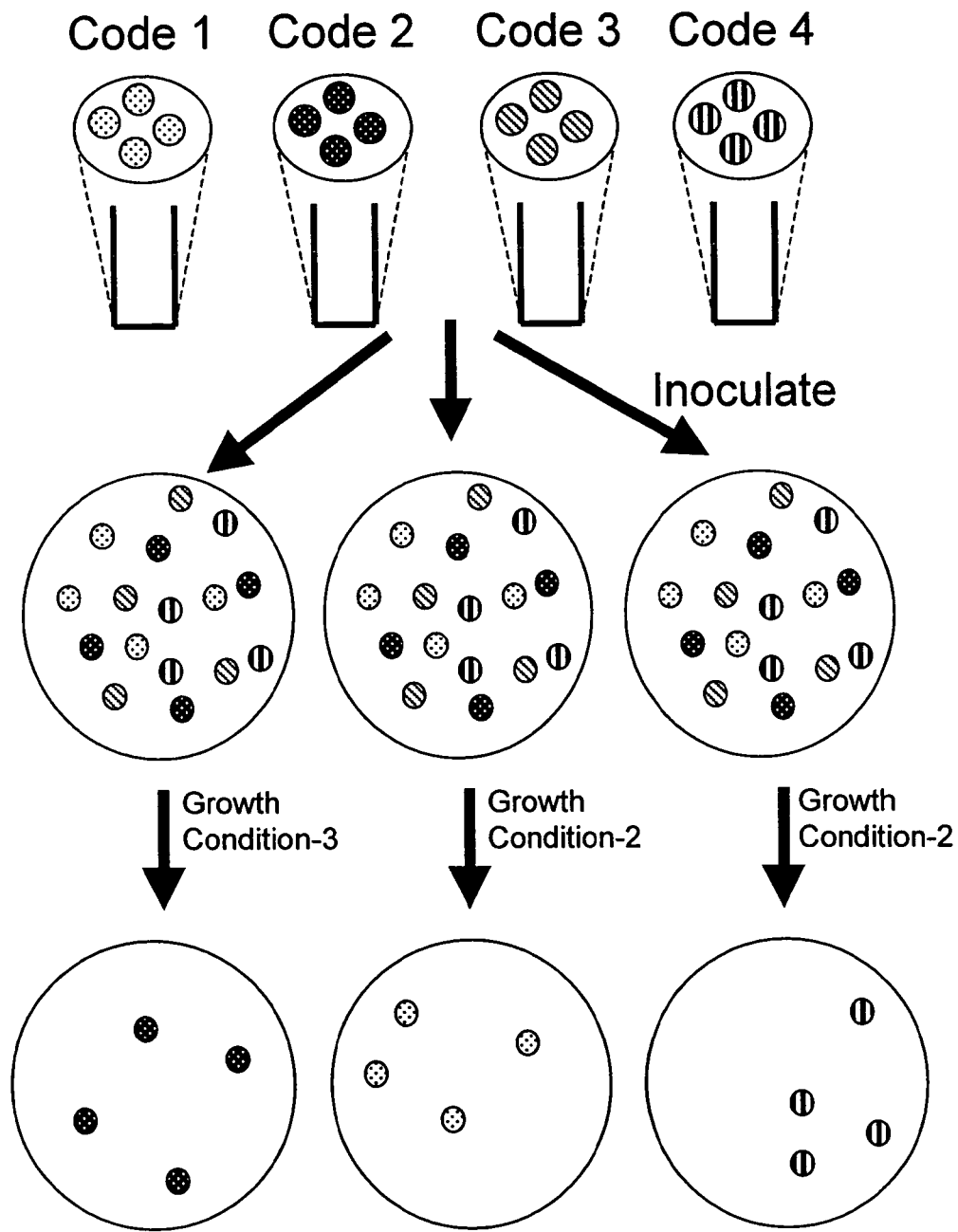
FIG. 17 is a pictorial representation illustrating the simultaneous single-plate screening of a plurality of different encoded cells for their ability to grow under selective conditions as described in Example 7.

Populations of specific and distinct yeast mutants are permeabilized to introduce a specific color set of SCNCs. Each of the populations of yeast mutants are prepared with an SCNC code that is distinguishable from the other of the populations of yeast mutants (see FIG. 17). The encoded mutants are then used to inoculate a common plate containing a suitable growth medium. Several plates containing such mixed inocula of yeast mutants can be prepared.

Sets of inoculated plates are incubated under a chosen condition having altered temperature, light source, humidity or nutrient availability as compared to standard growth conditions. After an appropriate growth period (1 hour to 1 week) colonies which have formed can be spectrally decoded to identify the original mutant from which it derived.

Example 8

Immunostaining of SCNC-Encoded Cells Herceptin Antibody Immunostaining of SKBR3 Cells SKBR3 cells were seeded into an 8-well chamber slide at a density of 80,000 cells per well and encoded with green (530 nm) SCNCs using the cationic lipid BioPorter as described in Example 3. Encoded or unencoded cells were incubated overnight at 37° C., 5% $CO_2$. Cells were washed three times with PBS, and fixed in the presence of 3.7% formaldehyde for 10 minutes. The cells were washed 3 times with PBS, and incubated in the presence of PBS/1% bovine serum albumin (BSA) at room temperature for 30 minutes to minimize non-specific binding.

The cells in each well were incubated with 5 g/ml herceptin antibody in PBS/1% BSA in a total volume of 150 1 for 30 min at room temperature. The cells were washed five times with PBS, and incubated with a 1:500 dilution of biotinylated goat anti-human IgG (Vector Laboratories, 1.5 mg/ml) for 30 minutes. The cells were washed again with PBS and incubated with a 1:400 dilution of streptavidin-conjugated Cy3 (Amersham, 1 mg/ml) for 30 minutes. The cells were washed again with PBS and the slide was mounted using 50% glycerol in PBS. The cells were imaged using a Nikon fluorescence microscope equipped with a Cy3 and green SCNC filter set. Control experiments indicate that binding of herceptin is unaffected by the SCNC code. The results indicate that the binding of herceptin is unaffected by the SCNC encoding process or by the presence of intracellular SCNC.

Example 9

Immunostaining of SCNC-Encoded Cells

Encoded Anti-Tubulin Immunostaining of CHO Cells

Chinese hamster ovary (CHO) cells were seeded into an 8-well chamber slide at a density of 15,000 cells per chamber. The cells were encoded with green (530 nm) SCNCs dots using Chariot reagent as described in Example 1. The cells were incubated overnight in complete medium (DMEM-F12, 10% fetal bovine serum (FBS), 2 mM L-glutamine). Cells were washed 3 times with PBS, and fixed with 3.7% formaldehyde in PBS at room temperature for 10 minutes. The cells were washed 4 times with PBS, and incubated for 30 minutes at room temperature in the presence of PBS/1% bovine serum albumin (BSA). Anti-tubulin antibody (rabbit IgG fraction, whole de-lipidized antsera, Sigma) was diluted 1:200 in PBS/1% BSA and incubated with cells at room temperature for 30 minutes. The cells were washed 5 times with PBS, and incubated with biotinylated goat anti rabbit IgG (Vector Laboratories, Burlingame, Calif. stock is 1.5 mg/ml) at a 1:500 dilution in PBS/1% BSA for 30 minutes. The cells were washed 5 times with PBS and incubated with streptavidin conjugated Cy3 (Amersham, 1 mg/ml stock solution) diluted 1:400 in PBS for 30 minutes. The cells were washed 5 times with PBS and the slide was mounted using 50% glycerol in PBS. Cells were imaged using a Nikon fluorescence microscope equipped with a Cy3 and green SCNC filter set. The results indicate that the binding of anti-tubulin is unaffected by the SCNC encoding process or by the presence of intracellular SCNC.

Example 10

A Reporter Gene Assay for the 2 Adrenergic Receptor Using SCNC-Encoded Cho Cells Chinese hamster ovary (CHO) cells expressing the 2 adrenergic receptor and renilla luciferase reporter gene were encoded with green (530 nm) SCNCs using the Chariot reagent as described in Example 1. Encoded cells or unencoded cells were seeded into the wells of a white, clear-bottom, 96-well plate at a seeding density of 100,000 cells per well. The cells were incubated overnight in complete medium (DMEM-F12, 10% fetal bovine serum (FBS), 2 mM L-glutamine, and 1 mg/ml G418 (Gibco BRL)).

Figure 18:
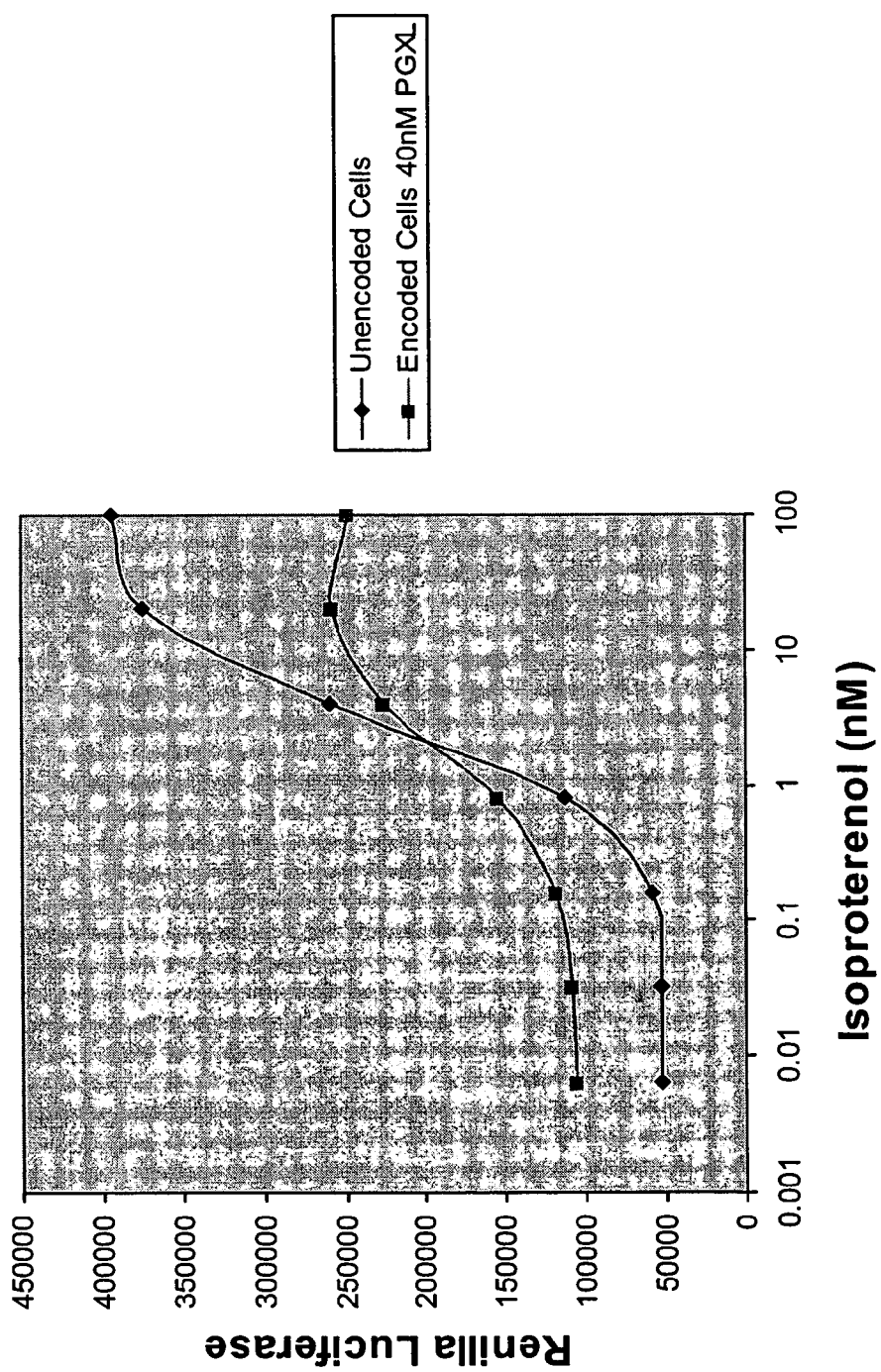
FIG. 18 is a graphical representation of isoproterenol dose responses of encoded or unencoded CHO cells expressing the MI muscarinic receptor.

The cells were washed and starved for 20-24 hrs by incubating them in DMEM-F12 medium lacking serum and phenol red. The beta receptor agonist isoproterenol (Sigma) was diluted at various concentrations in DMEM-F12 medium and incubated with cells for four hours. To measure expression of the reporter gene, cells were washed with PBS and assayed for renilla luciferase activity using the RenLuc kit (Promega). Luminescence was measured using a Tecan SpectraFluor Plus plate reader. The dose response curves shown in FIG. 18 indicate that the $EC_{50}$ values for encoded or unencoded cells are nearly identical, but that the encoded cells have a smaller signal dynamic range.

Example 11

An Fluorescence Competition Binding Assay for the β2 Adrenergic Receptor Using SCNC-Encoded Cho Cells CHO cells expressing the 2 adrenergic receptor were encoded with green (530 nm) SCNCs using Chariot reagent as described in Example 1. Encoded or unencoded cells were seeded into 8-well chamber slides at a density of 40,000 cells per chamber. The cells were incubated overnight in complete medium.

Figure 19B:
FIG. 19 illustrates the non-competed (19A) and competition binding of 1 FM CGP 12177 (19B) to encoded CHO cells expressing the b2 adrenergic receptor.
Figure 19A:
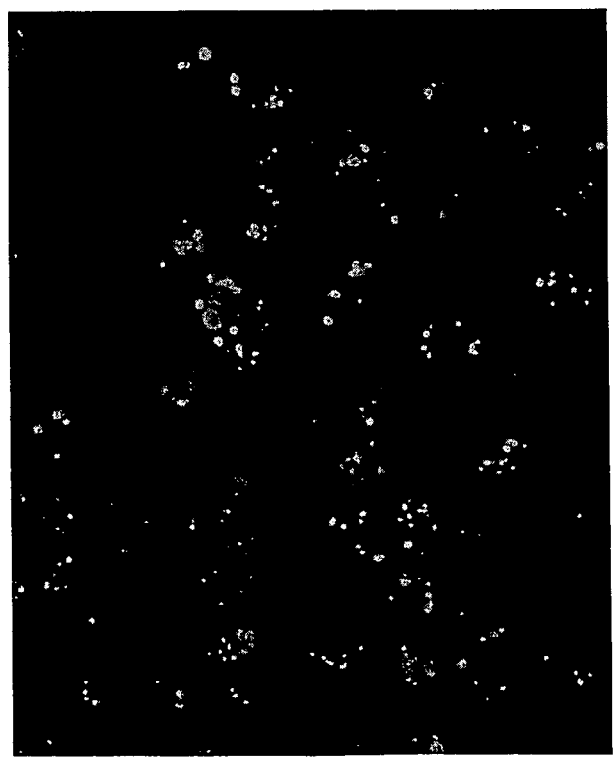

The chamber slides were chilled at 4° C. for approximately 20 minutes, and the cells were washed once with cold binding buffer (serum- and phenol red-free DMEM-F12 supplemented with 0.1% BSA). The cells were incubated in binding buffer in the presence or absence of 1 M unlabeled CGP12177 ligand (Sigma). The slides were incubated at 4° C. for 30 minutes. To bind the fluorescent ligand, BODIPY® TMR (±) CGP 12177 (Molecular Probes) was added to a final concentration of 250 nM in binding buffer, and the slides were wrapped in aluminum foil and incubated at 4° C. for 1 hour. Each well was washed 4 times with binding buffer and the slides were mounted with 50% glycerol in PBS. Cells were imaged using a Nikon fluorescence microscope equipped with a Cy3 and green SCNC filter set (FIG. 19). Control experiments indicate that competition binding of CGP12177 is essentially the same for either encoded or unencoded cells.

Example 12

A Calcium Assay for the M1 Muscarinic Receptor Using SCNC-Encoded CHO Cells

CHO cells expressing the M1 muscarinic receptor M1WT3 (American Type Culture Collection, catalog number CRL-1985) were encoded with green (530 nm) SCNCs using the Chariot reagent as described in Example 1. Encoded or unencoded cells were seeded into the wells of a 96-well assay plate at a density of 10,000 cells per well and grown overnight in complete medium (Ham's F12K, 10% fetal bovine serum (FBS), 2 mM L-glutamine). A calcium dye loading solution using the FLEXstation calcium assay kit (Molecular Devices) was prepared according the manufacturer's directions. The loading buffer was supplemented with 2.5 mM probenecid to inhibit anion-exchange proteins and prevent loss of internalized dye. To load cells with the calcium indicator dye, 100 1 of loading solution is added to 100 1 of medium per well, and the plate was incubated at 37° C., 5% $CO_2$ for 1 hr.

The plate was removed and placed on the microscope-based system for visualizing fluorescent images described above and in commonly owned U.S. application Ser. No. 09/827,076, entitled "Two-dimensional Spectral Imaging System" by Empedocles et al., filed Apr. 5, 2001, for imaging. Compounds were diluted in complete medium and added to the wells. The plate was incubated at room temperature for 5 minutes, and the cells were imaged as described in Example 5. The results indicate that the agonist carbachol can stimulate the calcium response of either unencoded or encoded cells.

Example 13

A GPCR Internalization Assay for Multiplex Screening Of Agonist or Antagonist Ligands Using SCNC-Encoded Cells A method is described for encoding and multiplexing a GPCR internalization assay. Many, if not all, GPCRs undergo agonist-dependent aggregation on the cell surface and subsequent internalization via clathrin coated pits. The internalized GPCR is contained within an endosome, which is either recycled back to the membrane or targeted to the lysosome for degradation. An assay, based on visualizing the movement of a fluorescent-tagged receptor from the cell surface to an endosomal compartment, has been shown for several GPCRs, including the parathyroid hormone receptor (Conway et al. (1999) *J. Biomol. Screening* 4(2):75-86), cholecystokinin receptor type A (Tarasova et al. (1997) *J. Biol. Chem.* 272 (23):14817-24) and 2 adrenergic receptor (Kallal et al. (1998) *J. Biol. Chem.* 273(1):322-8). A receptor chimera, comprised of green fluorescent protein (GFP) fused to the cytoplamic C-terminal tail of the GPCR, can be used to visualize receptor trafficking. It should also be possible, however, to tag the GPCR with a short epitope sequence displayed on one of its extracellular loops, and to label the receptor with an anti-epitope antibody conjugated to a fluorescent dye molecule or SCNC. Examples of such epitope sequences include the eight amino acid sequence FLAG peptide (Chubet et al. (1996) *Biotechniques* 20(1):136-41), or the nine amino acid sequence influenza virus hemagglutinin (HA) peptide (Koller et al. (1997) *Anal. Biochem.* 250(1):51-60).

To multiplex an internalization assay using epitope-tagged GPCRs, cell lines expressing various GPCRs are encoded as described in, e.g., Example 1, 2 or 3, and mixed. The mixed cells are added to the wells of a clear bottom assay plate. The fluorescent dye-labeled antibody is added, followed by the compound. The cells are incubated at 37° C. for 30-60 minutes, and the assay plate and cells are imaged using a fluorescence microscope. Alternatively, the cells can be fixed with paraformaldehyde or some other fixative agent, and the plates are stored at 4° C. for imaging at a later time. Binding of an agonist ligand to the GPCR will cause internalization of the GPCR and its bound antibody, which can be visualized under the microscope as a movement of fluorescence from the cell surface to an intracellular compartment. To screen for antagonists, the compounds are screened for their ability to block the agonist-dependent internalization of the receptor. This method can also be used to screen for agonist ligands of orphan GPCRs.

Example 14

A Method for Encoding and Assaying Cells Grown in a Macroporous Gelatin Microcarrier A method is described for encoding and screening cells grown on a microcarrier bead surface. An example of such a microcarrier is CultiSpher™ from HyClone Laboratories, Inc. CultiSpher™ is a macroporous gelatin microcarrier bead that provides a very large interior surface for cell attachment. The large surface-to-area ratio of the beads results in much higher cell yields compared to conventional liquid cell cultures.

Microcarrier beads can be encoded using chemical methods (see, e.g., U.S. Pat. No. 6,207,392, PCT Publication No. WO 00/17103, and Han et al. (2001) *Nature Biotech.* 19:632-635) and then used as a substrate on which to grow cells. An advantage of this method is that encoding is done on the bead scaffold used to grow the cells, and not on individual cells. Methods for encoding the beads include adsorbing a unique SCNC code to the bead surface, or encapsulating the code within the interior of the bead.

To perform a multiplex assay using this method, the microcarrier beads are encoded and stored until ready for use. Cells expressing a receptor target of interest are added to the encoded beads and incubated in culture medium to allow cell attachment. The beads on which each cell line have been grown are combined, and aliquots of the mixture are added to the wells of an assay plate.

There are a variety of assays that can be adapted for use with encoded microcarrier beads and cells. For example, binding of a fluorescent ligand to a cell surface receptor can be measured by flow cytometry of the microcarrier/cell complexes. Fluorescence microscopy can be used to image calcium flux or expression of a reporter gene using cells grown on microcarrier beads.

Example 15

A Method for Screening 600 GPCRs Using a 10-plex SCNC-Encoded Cell Assay

A method is described for screening 600 GPCRs against 96 compounds using a 10-plex encoded cell assay.

The compounds from a 96-well compound plate are replica plated to 60 96-well daughter plates. Alternatively, a 20-plex assay would require 30 compound daughter plates, and a 60-plex assay would only require 10 daughter plates. For a 10-plex assay, the 60 daughter plates are divided into 6 groups of 10 plates each.

The 600 GPCR cell lines are stored as frozen cells, and are thawed as needed. An important advantage of this method is that far fewer cells are used for screening compared to conventional screening methods. For example, fewer than 100 cells per GPCR are screened in a well using encoded cell technology, compared to 50,000 cells per GPCR using a conventional calcium assay such as the Fluorescent Imaging Plate Reader (FLIPR) from Molecular Devices. Therefore, all of the GPCR cell lines required for the encoded cell technology can be grown in 6-well culture plates compared to the large flasks or bioreactors that are required for conventional screening. Growing the cells in 6-well culture plates is also more amenable to automation compared to conventional screening.

To encode the 600 GPCR cell lines, the cells are transferred to 100 6-well culture plates and grown to a cell density of about $0.5-1.0\times10^6$ cells per well. The 600 wells are organized according to the multiplexing capability of the assay. For example, a 10-plex assay would require that 600 wells be organized into 60 groups, each group comprised of 10 wells, while a 60-plex assay would be organized as 10 groups of 60 wells each. The cell codes are stored as premixed color combinations of SCNCs, and are used as previously described. The number of SCNC colors necessary for a 10-plex, 20-plex, and 60-plex assays using single emission intensity levels are 4, 5, and 6, respectively.

For a 10-plex assay, the cell lines growing in 10 different wells are encoded with one of the 10 SCNC codes as described, for example, in Examples 1 and 3. The cells are encoded, lifted from each of the 10 wells, counted, and pooled such that the number of cells comprising each GPCR cell line is approximately equal. For example, pooling $0.5\times10^6$ cells from each well would result in a mixture containing a total of $5\times10^6$ cells. Cells from the mix are distributed to all the wells of a 96-well assay plate at a seeding density of 10,000 total cells per well (equivalent to 1000 cells per GPCR cell line). This process is repeated 60 times until all 600 GPCR cell lines are contained within the wells of 60 assay plates.

This screening method can be adapted to a variety of assay formats. One such assay is the GPCR internalization assay described above using epitope-tagged GPCRs. The anti-epitope fluorescent antibody is added to the wells of the 60 assay plates. Compounds from the 60 compound replica plates are transferred to the assay plates, and the plates are incubated at 37° C., 5% $CO_2$ for 30-60 minutes for receptor internalization to occur. The cells are fixed with paraformaldehyde and stored at 4° C. until ready for imaging.

The cells are imaged using an automated high-throughput fluorescence microscope. A nuclear stain such as Hoechst 33258 (350 nm excitation, 461 nm emission) is used to identify single cells within a field of view. To screen for agonist compounds, the cells are screened for the internalization of the fluorescent reporter bound to the antibody. Positive cells are then scanned using multiple filters to determine the SCNC code. This process is repeated at either single or multiple fields of view per well until a statistically significant number of data points are collected. Image and data processing are used to store and analyze the data.

Example 16

Peptide-Mediated Uptake of SCNCs Using Binding Pairs

Figure 20:
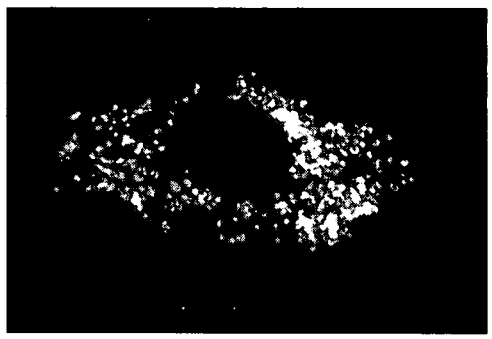
FIG. 20 shows the results of peptide mediated uptake of SCNCs using biotinylated D-Arg9 (nine contiguous D-Arg residues), and streptavidin conjugated quantum dots. HeLa Cells were labeled with Qtracker™ 655 Reagent (Quantum Dot Corporation, Hayward, Calif.) and a Leica SP-2 confocal microscope was used to observe the Qtracker™ reagent in cytoplasm at an excitation of 488 nm.

A labeling solution was made by pre-mixing 1 µL of 2 µM streptavidin conjugated quantum dots with an emission maximum of 655 nm (Quantum Dot Corporation, Hayward, Calif.) and 100 µM biotinylated D-Arg9 (nine contiguous D-Arg molecules) (CS Bio Co., Inc., San Carlos, Calif.) into a 1.5 mL microcentrifuge tube. 200 µL of fresh full growth medium with 10% serum (Invitrogen, Carlsbad, Calif.) was added and vortexed for 30 seconds. The medium used was the ATTC recommended medium for HeLa cells. This medium includes minimum essential medium (Eagle) with 2 mM L-glutamine and Earle's BSS adjusted to contain 1.5 g/L sodium bicarbonate, 0.1 mM non-essential amino acids, and 1.0 mM sodium pyruvate, 10% fetal bovine serum. The entire quantity of labeling solution was added to a monolayer of HeLa cells subcultured overnight in one well of an 8-well Lab-Tek chambered coverglass system (Nunc, Rochester, N.Y.). After incubation at 37° C. in a humidified atmosphere of 95% air, 5% $CO_2$ for 45-60 minutes, the cells were washed twice with fresh growth medium. The image shown in FIG. 20 was captured using Leica SP-2 confocal microscope with 488 nm excitation.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. A composition, comprising a micelle dispersed in aqueous solution, wherein the micelle comprises:
   (a) one or more semiconductor nanoparticles encapsulated with a negatively charged amphiphilic polymer, wherein the amphiphilic polymer is a block copolymer or grafted polymer that comprises at least one hydrophilic segment and at least one hydrophobic segment that encapsulates the one or more semiconductor nanoparticles through hydrophobic interaction, and
   (b) a cationic polypeptide comprising 5 to 25 contiguous lysine and/or arginine residues, wherein the cationic polypeptide is associated with the at least one hydrophilic segment of the amphiphilic polymer;
   wherein the micelle is capable of enhancing the transport of the one or more semiconductor nanoparticles across a biological membrane.

2. The composition of claim 1, wherein the semiconductor nanoparticle is a semiconductor nanocrystal.

3. The composition of claim 2, wherein the semiconductor nanocrystal comprises a core selected from the group consisting of ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, AlAs, AlP, AlSb, AlS, Ge, Si, Pb, PbS, PbSe, and a mixture thereof.

4. The composition of claim 3, wherein the semiconductor nanocrystal core is surrounded by a semiconductor shell.

5. The composition of claim 4, wherein the semiconductor shell comprises a semiconductor material selected from the group consisting of ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, AlAs, AlP, AlSb, AlS, Ge, Si, Pb, PbS, PbSe, and a mixture thereof.

6. The composition of claim 5, wherein the core comprises CdSe and the shell comprises ZnS.

7. The composition of claim 1, wherein the cationic polypeptide comprises 7 to 15 contiguous arginine residues.

8. The composition of claim 1, wherein the cationic polypeptide comprises 9 contiguous arginine residues.

9. The composition of claim 1, wherein the amphiphilic polymer comprises a reactive group selected from a carboxyl, aldehyde, alcohol, and amine group.

10. The composition of claim 1, wherein the micelle is crosslinked.

11. The composition of claim 1, wherein the semiconductor nanoparticle is associated with the cationic polypeptide using first and second members of a binding pair.

12. The composition of claim 11, wherein the first member of the binding pair is streptavidin, avidin, or neutravidin and the second member of the binding pair is biotin.

13. The composition of claim 11, wherein the first member of the binding pair is associated with the semiconductor nanoparticle and the second member of the binding pair is coupled to the cationic polypeptide.

14. The composition of claim 13, wherein the semiconductor nanoparticle is associated with streptavidin and the cationic polypeptide is coupled to biotin.

15. The composition of claim 1, wherein the biological membrane is a cell membrane.

16. A method of enhancing the transport of a semiconductor nanoparticle across a biological membrane comprising contacting a cell with the composition of claim 1, under conditions that provide for the transport of the semiconductor nanoparticle across the biological membrane.

17. A method of distinguishably identifying a cell, comprising: (a) providing a cell; and (b) contacting the cell with a composition according to claim 1 under conditions in which the semiconductor nanoparticle is transported across the cell membrane to provide a labeled cell, thereby identifying the cell.

18. A method of identifying a cell in a mixed population of cells, comprising: (a) providing a first cell; (b) contacting the cell with a composition according to claim 1 under conditions in which the semiconductor nanoparticle is transported across the cell membrane to provide an encoded first cell; (c) mixing the encoded first cell with a second cell distinct therefrom to form a mixed population of cells; (d) culturing the mixed population of cells; (e) exposing the cultured mixed population of cells to an excitation energy source; and (f) detecting a semiconductor nanoparticle code to identify the encoded cell.

19. A kit comprising a composition according to claim 1 and instructions for preparing encoded cells using the composition.

20. A live cell associated with the composition of claim 1.

21. The live cell of claim 20, wherein the composition resides in the cytoplasm of the cell.

* * * * *

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial
<220> FEATURE:
<223> OTHER INFORMATION: peptide fragment of HIV-TAT basic region

<400> SEQUENCE: 1

Arg Lys Lys Arg Arg Gln Arg Arg Arg
1               5

<210> SEQ ID NO 2
<211> LENGTH: 12
<212> TYPE: PRT
<213> ORGANISM: Artificial
<220> FEATURE:
<223> OTHER INFORMATION: peptide fragment from SV40 large T NLS

<400> SEQUENCE: 2

Cys Gly Gly Gly Pro Lys Lys Arg Lys Val Gly
1               5                   10

<210> SEQ ID NO 3
<211> LENGTH: 13
<212> TYPE: PRT
<213> ORGANISM: Artificial
<220> FEATURE:
<223> OTHER INFORMATION: peptide fragment from adenoviral NLS

<400> SEQUENCE: 3

Cys Gly Gly Phe Ser Thr Ser Leu Arg Ala Arg Lys Ala
1               5                   10

<210> SEQ ID NO 4
<211> LENGTH: 17
<212> TYPE: PRT
<213> ORGANISM: Artificial
<220> FEATURE:
<223> OTHER INFORMATION: peptide fragment from adenoviral RME

<400> SEQUENCE: 4

Cys Lys Lys Lys Lys Lys Lys Ser Glu Asp Glu Tyr Pro Tyr Val Pro
1               5                   10                  15

Asn

<210> SEQ ID NO 5
<211> LENGTH: 28
<212> TYPE: PRT
<213> ORGANISM: Artificial
<220> FEATURE:
<223> OTHER INFORMATION: peptide fragment from adenoviral fiber protein

<400> SEQUENCE: 5

Cys Lys Lys Lys Lys Lys Lys Lys Ser Glu Asp Glu Tyr Pro Tyr Val
1               5                   10                  15

Pro Asn Phe Ser Thr Ser Leu Arg Ala Arg Lys Ala
            20                  25
```